US009261505B2

(12) United States Patent
Pereira et al.

(10) Patent No.: US 9,261,505 B2
(45) Date of Patent: **\*Feb. 16, 2016**

(54) BIOMARKERS FOR PRENATAL DIAGNOSIS OF CONGENITAL CYTOMEGALOVIRUS

(71) Applicant: THE REGENTS OF THE UNIVERSITY OF CALIFORNIA, San Francisco, CA (US)

(72) Inventors: Lenore Pereira, San Francisco, CA (US); Ekaterina Maidji, San Francisco, CA (US); Takako Tabata, South San Francisco, CA (US); Susan Jane McDonagh, Inverness (GB)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,938

(22) Filed: Oct. 25, 2013

(65) Prior Publication Data

US 2014/0141406 A1     May 22, 2014

Related U.S. Application Data

(63) Continuation of application No. 12/739,400, filed as application No. PCT/US2008/080815 on Oct. 22, 2008, now Pat. No. 8,609,347.

(60) Provisional application No. 60/981,756, filed on Oct. 22, 2007.

(51) Int. Cl.
| | |
|---|---|
| *G01N 33/53* | (2006.01) |
| *C07K 16/00* | (2006.01) |
| *C12P 21/08* | (2006.01) |
| *C07K 16/08* | (2006.01) |
| *G01N 33/569* | (2006.01) |

(52) U.S. Cl.
CPC .... G01N 33/56994 (2013.01); *G01N 2333/045* (2013.01)

(58) Field of Classification Search
None
See application file for complete search history.

(56) References Cited

U.S. PATENT DOCUMENTS 6,828,113 B2 * 12/2004 Witkin ........................... 435/7.1
8,609,347 B2 * 12/2013 Pereira et al. ................. 435/7.1

FOREIGN PATENT DOCUMENTS

WO    WO 2009/055487 A1    4/2009

OTHER PUBLICATIONS

Asano et al., "Involvement of αvβ5 Integrin-Mediated Activation of Latent Transforming Growth Factor β1 in Autocrine Transforming Growth Factor β Signaling in Systemic Sclerosis Fibroblasts" *Arthritis & Rheumatism*, vol. 52, No. 9, pp. 2897-2905 (2005).
Barbara et al., "Endoglin Is an Accessory Protein That Interacts with the Signaling Receptor Complex of Multiple Members of the Transforming Growth Factor-β Superfamily" *The Journal of Biological Chemistry*, vol. 274, pp. 584-594 (1999).
Bartee et al., "Quantitative Membrane Proteomics Reveals New Cellular Targets of Viral Immune Modulators" *PLOS Pathogens*, vol. 2, No. 10, pp. 975-988 (2006).
Duff et al., "CD105 is important for angiogensis: evidence and potential applications" *FASEB*, vol. 17, pp. 984-992 (2003).
Enders et al., "Prenatal diagnosis of congenital cytomegalovirus infection in 189 pregnancies with known outcome" *Prenatal Diagnosis*, vol. 21, No. 5, pp. 362-377 (2001).
Fisher et al., "Human Cytomegalovirus Infection of Placental Cytotrophoblasts In Vitro and In Utero: Implications for Transmission and Pathogenesis" *Journal of Virology*, vol. 74, No. 15, pp. 6808-6820 (2000).
Fisher, "The placental problem: Linking abnormal cytotrophoblast differentiation to the maternal symptoms of preeclampsia" *Reproductive Biology and Endocrinology*, vol. 2:53 (2004).
Fonsatti et al., "Highlights on endoglin (CD 1 05): from basic findings towards clinical applications in human cancer" *Journal of Translational Medicine*, vol. 2, No. 18 (2004).
Garcia et al., "Placental Morphology in Cytomegalovirus Infection" *Planenta*, vol. 10, pp. 1-18 (1989).
Gougos and Letarte, "Primary Structure of Endoglin, an RDG-containing Glycoprotein of Human Endothelial Cells" *The Journal of Biological Chemistry*, vol. 265, No. 15, pp. 8361-8364 (1990).
Haagmans et al., "Transforming growth factor β production during rat cytomegalovirus infection" *Journal of General Virology*, vol. 78, pp. 205-213 (1997).
Hassan et al., "Immunological response to cytomegalovirus in congenially infected Neonates" *Clinical and Experimental Immunology*, vol. 147, No. 3, pp. 465-471 (2007).
Helanterä et al., "The Role of Cytomegalovirs Infection in Chronic Allograft Nephropathy" (Letters to the Editor), *Transplantation*, vol. 79, p. 379 (2005).
Ishida et al., "Intracellular TGF-β Receptor Blockade Abrogates Smad-Dependent Fibroblast Activation In Vitro and In Vivo", *Journal of Investigative Dermatology*, vol. 126, pp. 1733-1744 (2006).
Kossman et al., "Cytomegalovirus Production by Infected Astrocytes Correlates with Transforming Growth Factor-β Release" *Journal of Infectious Diseases*, vol. 187, pp. 534-541 (2003).
Lebrin et al., "Endoglin promotes endothelial cell proliferation and TGF-β/ALK1 signal transduction" *The EMBO Journal*, vol. 23, No. 20, pp. 4018-4028 (2004).
Levine et al., "Circulating Angiogenic Factors and the Risk of Preeclampsia" *The New England Journal of Medicine*, vol. 350, No. 7, pp. 672-683 (2004).
Levine et al., "Soluble endoglin and other circulating antiangioenic factors in preeclampsia", *New England Journal of Medicine*, Massachusetts Medical Society, Boston, MA, vol. 355, No. 10, pp. 992-1005 (2006).

(Continued)

*Primary Examiner* — James Martinelli
(74) *Attorney, Agent, or Firm* — Morgan, Lewis & Bockius LLP; Annette S. Parent

(57) ABSTRACT

The invention provides compositions and methods useful for early detection of congenital CMV infection, predicting the likelihood and severity of congenital CMV disease, and monitoring the efficacy of therapeutic approaches. Compositions of the present invention include biomarkers that are differentially expressed in CMV-infected mothers and fetuses compared to uninfected individuals.

6 Claims, 45 Drawing Sheets

(56) References Cited

OTHER PUBLICATIONS

Lu, et al., "Integrin α8β1 mediates adhesion to LAP-TGFβ1" *Journal of Cell Science*, vol. 115, pp. 4641-4648 (2002).

Ludbrook et al., "The integrinα,β$_3$ is a receptor for the latency-associated peptides of transforming growth factors β$_1$ and β$_3$" *Biochem. J.*, vol. 369, pp. 311-318 (2003).

Maidji et al., "Maternal Antibodies Enhance or Prevent Cytomegalovirus Infection in the Placenta by Neonatal Fc Receptor-Mediated Transcytosis" *American Journal of Pathology*, vol. 168, No. 4, pp. 1210-1226 (2006).

Maidji et al., "Developmental Regulation of Human Cytomegalovirus Receptors in Cytotrophoblasts Correlates with Distinct Replication Sites in the Placenta" *Journal of Virology*, vol. 81, No. 9, pp. 4701-4712 (2007).

Malek et al., "Evolution of Maternofetal Transport of Immunoglobulins During Human Pregnancy" *American Journal of Reproductive Immunology*, vol. 36, pp. 248-255 (1996).

Markel et al., "Pivotal role of CEACAM1 protein in the inhibition of activated decidual lymphocyte functions" *Journal Clinical Invest.*, vol. 110, No. 7, pp. 943-953 (2002).

Maynard et al., "Excess placental soluble fms-like tyrosine kinase 1 (Sflt1) may contribute to endothelial dysfunction, hypertension, and proteinuria in preeclampsia" *The Journal of Clinical Investigation*, vol. 111, No. 5, pp. 649-658 (2003).

Maynard et al., "Soluble Fms-like Tyrosine Kinase 1 and Endothelial Dysfunction in the Pathogenesis of Preeclaimpsia" *Pediatric Research*, vol. 57, No. 5, pp. 1R-7R (2005).

McDonagh et al., "Viral and Bacterial Pathogens at the Maternal-Fetal Interface" *The Journal of Infectious Diseases*, vol. 190, pp. 826-834 (2004).

McDonagh et al., "Patterns of human cytomegalovirus infection in term placentas: A preliminary analysis" *Journal of Clinical Virology*, vol. 35, pp. 210-215 (2006).

Michelson et al., "Human Cytomegalovirus Infection Induces Transcription and Secretion of Transforming Growth Factor Beta-1" *Journal Virol.* vol. 68, No. 9, pp. 5730-5737 (1994).

Mu et al., "The integrin αvβ8 mediates epithelial homeostasis through MT1-MMP-dependent activation of TGF-β1" *The Journal of Cell Biology*, vol. 157, No. 3, pp. 493-507 (2002).

Munger et al., "Interactions between Growth Factors and Integrins: Latent Forms of Transforming Growth Factor-β Are Ligands for the Integrin αvβ1" *Molecular Biology of the Cell*, vol. 9, pp. 2627-2638 (1998).

Munger et al., "The Integrin αvβ6 Binds and Activates Latent TGFβ1: A Mechanism for Regulating Pulmonary Inflammation and Fibrosis" *Cell*, vol. 96, pp. 319-328 (1999).

Nakao et al., "TFG-beta receptor-mediated signaling through Smad3 and Smad4" *EMBO Journal*, vol. 16, No. 17, pp. 5353-5362 (1997).

Nigro et al., "Passive Immunization during Pregnancy for Congenital Cytomegalovirus Infection" *The New England Journal of Medicine*, vol. 353, No. 13, pp. 1350-1362 (2005).

Oh, et al., "Activin receptor-like kinase 1 modulates transforming growth factor-β1 signaling in the regulation of angiogenesis" *PNAS*, vol. 97, No. 6, pp. 2626-2631 (2000).

Ota, et al., "Targets of Transcriptional Regulation by Two Distinct Type 1 Receptors for Transforming Growth Factor-β in Human Umbilical Vein Endothelial Cells" *Journal of Cellular Physiology*, vol. 193, pp. 299-318 (2002).

Park et al., "An elevated maternal plasma, but not amniotic fluid, soluble fms-like tyrosine kinase-1 (sFlt-1) at the time of mid-trimester genetic amniocentesis is a risk factor for preeclampsia" *American Journal of Obstetrics & Gynecology*, vol. 193, pp. 984-989 (2005).

Pepper, "Transforming Growth Factor-beta: Vasculogenesis, Angiogenesis, and Vessel Wall Integrity" *Cytokine & Growth Factor Reviews*, vol. 8, No. 1, pp. 21-43 (1997).

Pereira et al., "Human Cytomegalovirus Transmission from the Uterus to the Placenta Correlates with the Presence of Pathogenic Bacteria and Maternal Immunity" *Journal of Virology*, vol. 77, No. 24, pp. 13301-13314 (2003).

Rana et al., "Cytomegalovirus-induced mirror syndrome associated with elevated levels of circulating antiangiogenic factors" *Obstetrics and Gynecology*, Lipincott Williams & Wilkins, vol. 109, No. 2, pp. 549-552 (2007).

Sánchez-Elsner et al., "Endoglin Expression Is Regulated by Transcriptional Cooperation between the Hypoxia and Transforming Growth Factor-β Pathways" *The Journal of Biological Chemistry*, vol. 277, No. 46, pp. 43799-43808 (2002).

Simister et al., "An IgG-transporting Fc receptor expressed in the syncytiotrophoblast of human placenta" *Eur. J Immunol.*, vol. 26, pp. 1527-1531 (1996).

Staff et al., "Circulating concentrations of Sflt1 (soluble fms-like tyrosine kinase 1) in fetal and maternal serum during pre-eclampsia" *Eur J. Obstet. Gynecol. Reprod. Biol.*, vol. 122, No. 1, pp. 33-39 (2005).

Tabata et al., "Human Cytomegalovirus Interleukin-10 Downregulates Metalloproteinase Activity and Impairs Endothelial Cell Migration and Placental Cytotrophoblast Invasiveness" *J. Virol.*, vol. 78, No. 6, pp. 2831-2840 (2004).

Tabata et al., "Cytotrophoblasts Infected with a Pathogenic Human Cytomegalovirus Strain Dysregulate Cell-Matrix and Cell-Cell Adhesion Molecules: A Quantitative Analysis" *Placenta*, vol. 28, pp. 527-537 (2007).

Tabata et al., "Induction of an Epithelial Integrin αvβ6 in Human Cytomegalovirus-Infected Endothelial Cells Leads to Activation of Transforming Growth Factor-β1 and Increased Collagen Production" *The American Journal of Pathology*, vol. 172, No. 4, pp. 1127-1140 (2008).

Ten Dijke and Hill, "New insights into TGF-β-Smad signaling" *Trends in Biochemical Sciences*, vol. 29, pp. 265-273 (2004).

Wang et al., "Differential Regulation of Airway Epithelial Integrins by Growth Factors" *Am. J. Respir, Cell Mol. Biol.*, vol. 15, pp. 664-672 (1996).

Yamamoto-Tabata et al., "Human Cytomegalovirus Interleukin-10 Downregulates Metalloproteinase Activity and Impairs Endothelial Cell Migration and Placental Cytotrophoblast Invasiveness In Vitro" *Journal of Virology*, vol. 78, No. 6, pp. 2831-2840 (2004).

Yoo et al., "The IE2 Regulatory Protein of Human Cytomegalovirus Induces Expression of the Human Transforming Growth Factor β1 Gene through an Egr-1 Binding Site" *Journal of Virology*, vol. 70, pp. 7062-7070 (1996).

Zambruno et al., "Transforming Growth Factor-β1 Modulates β1 and β5 Integrin Receptors and Induces the de novo Expression of the αvβ6 Heterodimer in Normal Human Keratinocytes: Implications for Wound Healing" *The Journal of Cell Biology*, vol. 129, No. 3, pp. 853-865 (1995).

* cited by examiner

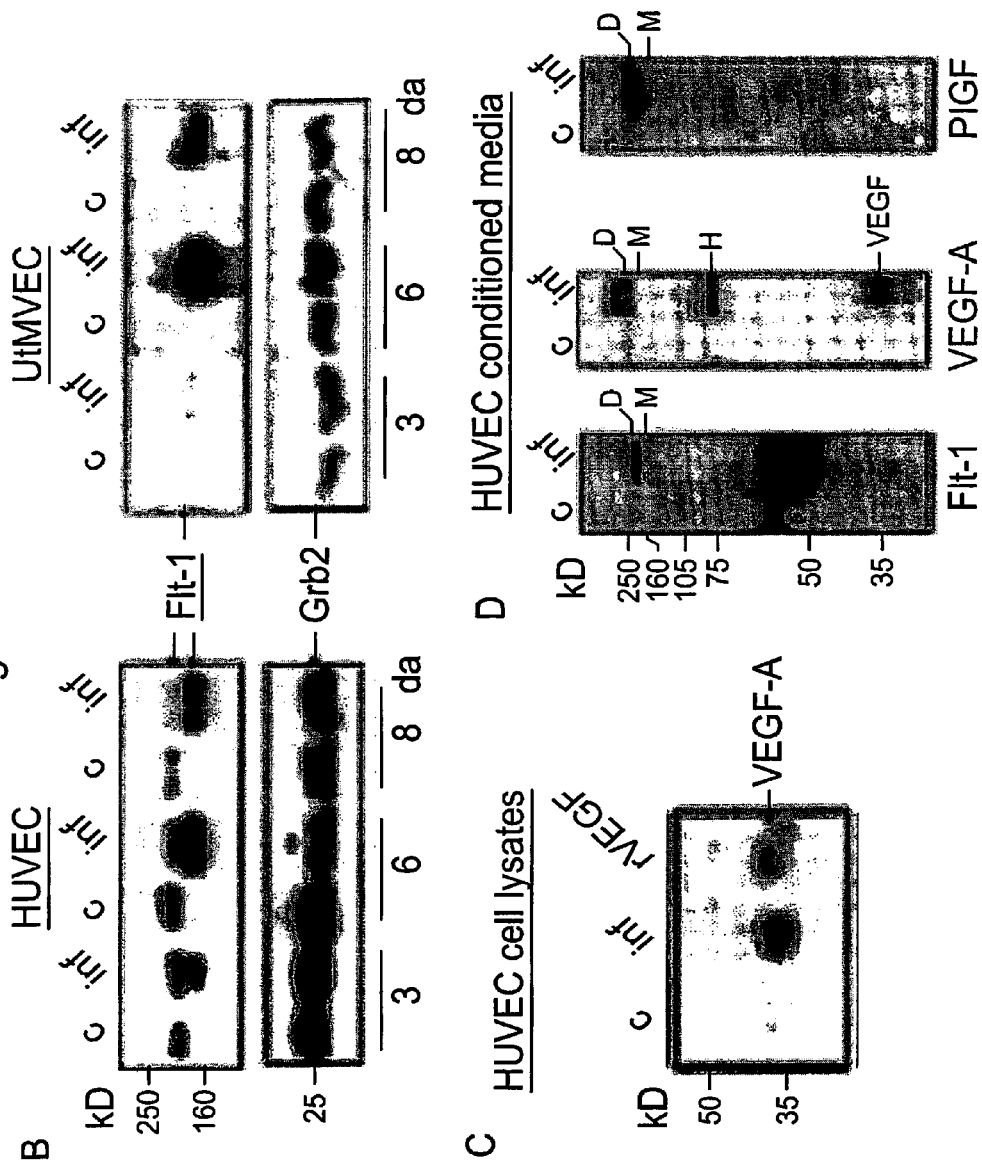

*Fig. 3*
A. CMV-infected HUVEC increased levels of sFlt1 in conditioned media.
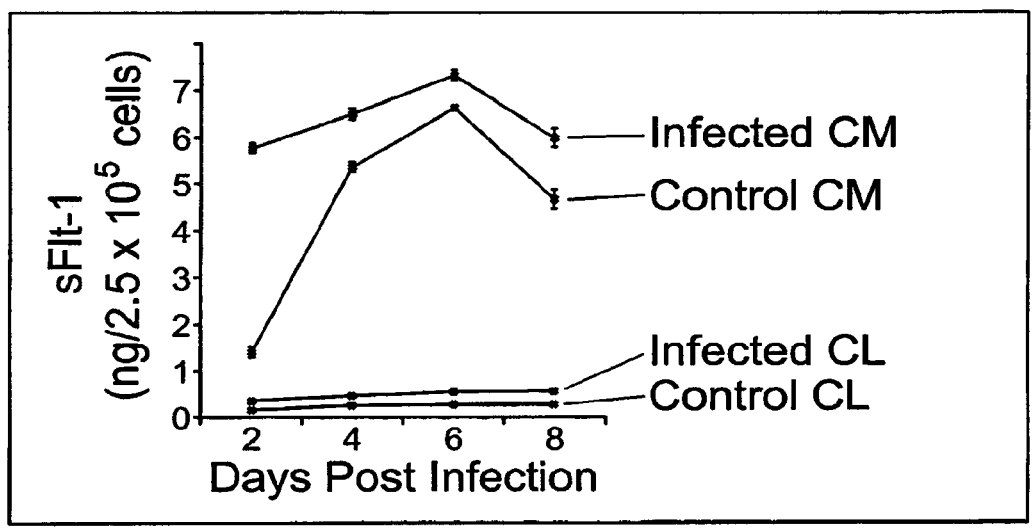
B. CMV infection increased levels of VEGF complexes in conditioned media.
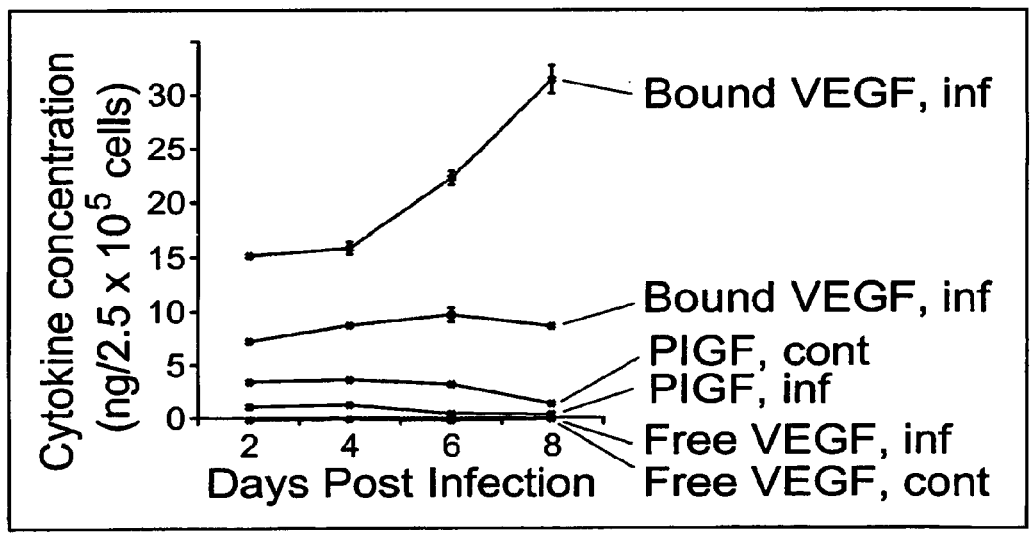

Increased CEACAM1 expression in VR1814-infected HUVEC

Fig. 6
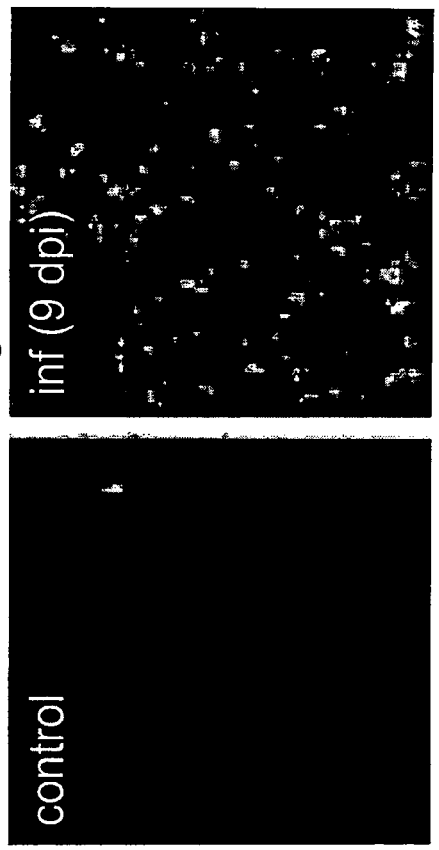
B
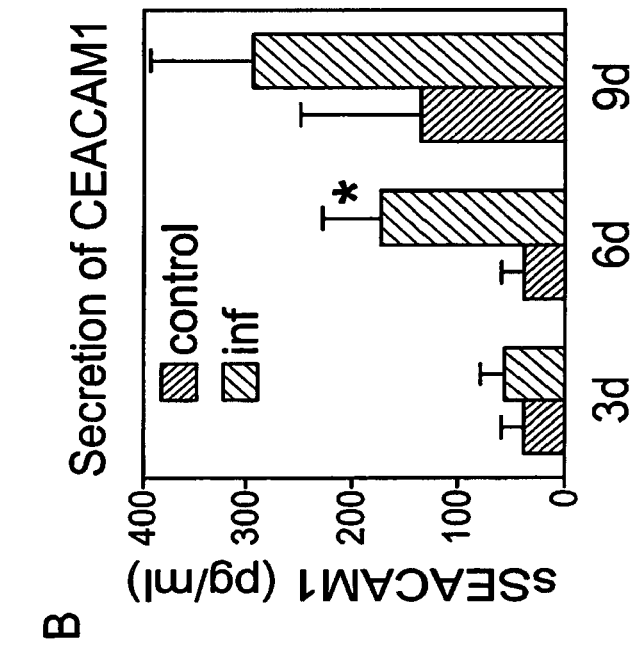
C Paracrine expression of CEACAM1
CEACAM1/CMVgB/nuclei

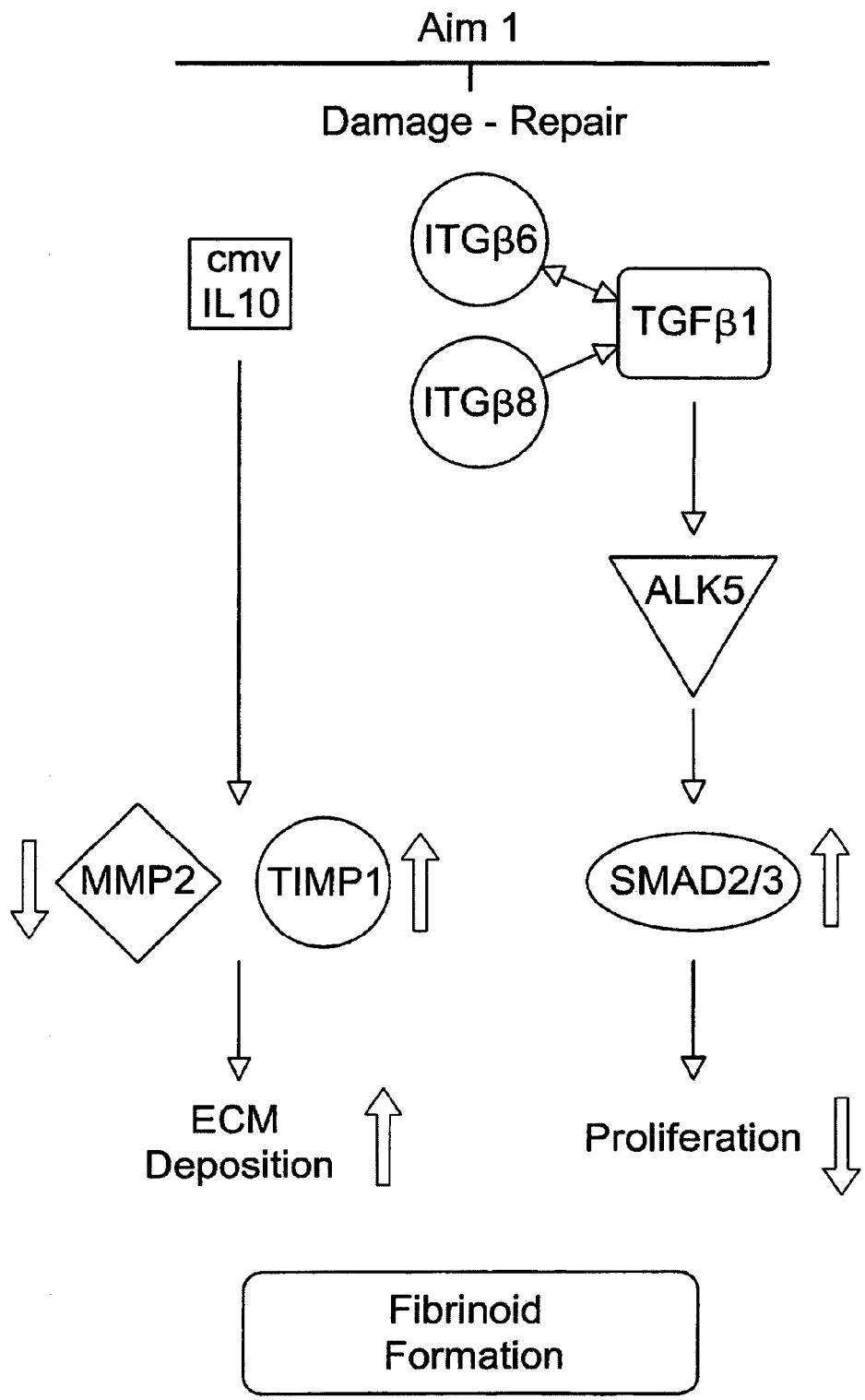

Fig. 18
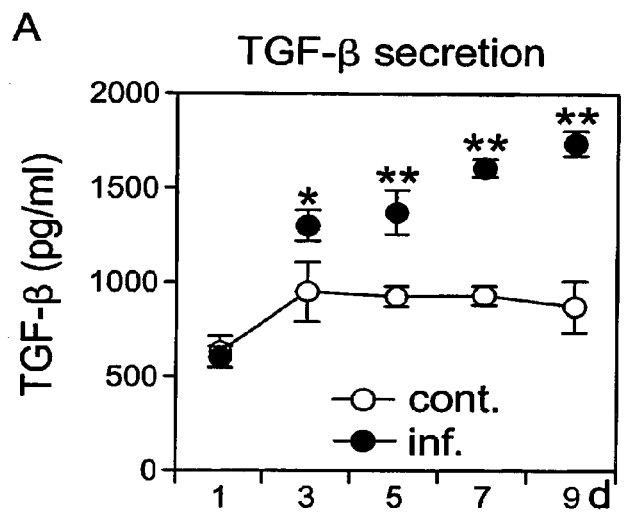
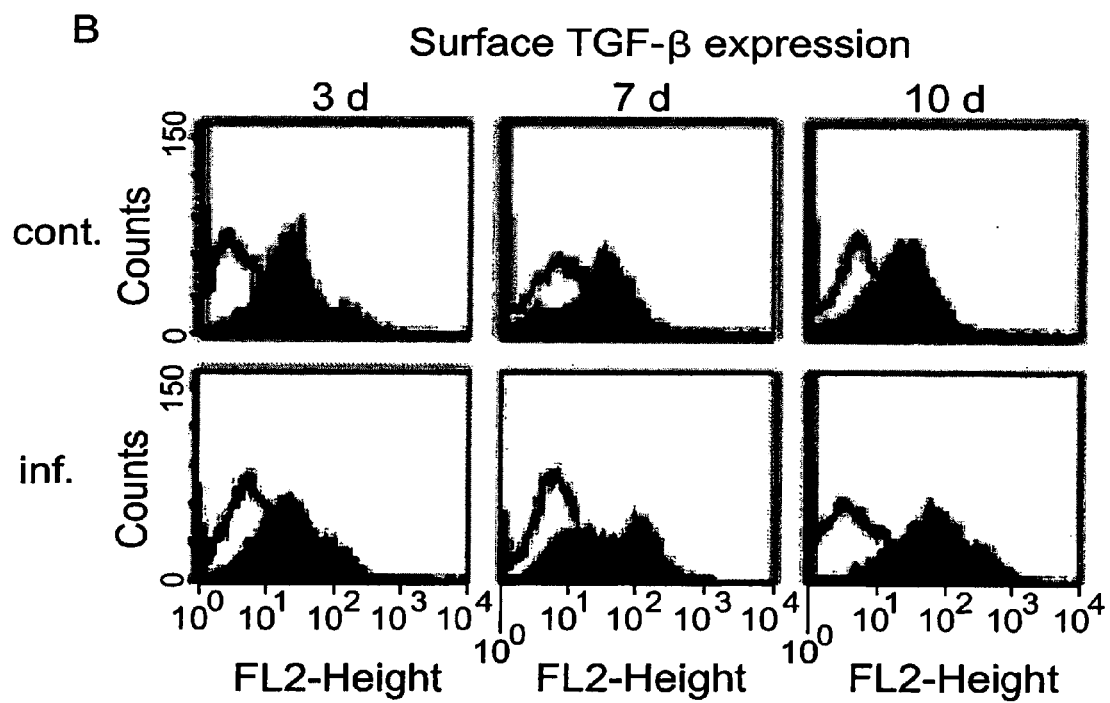

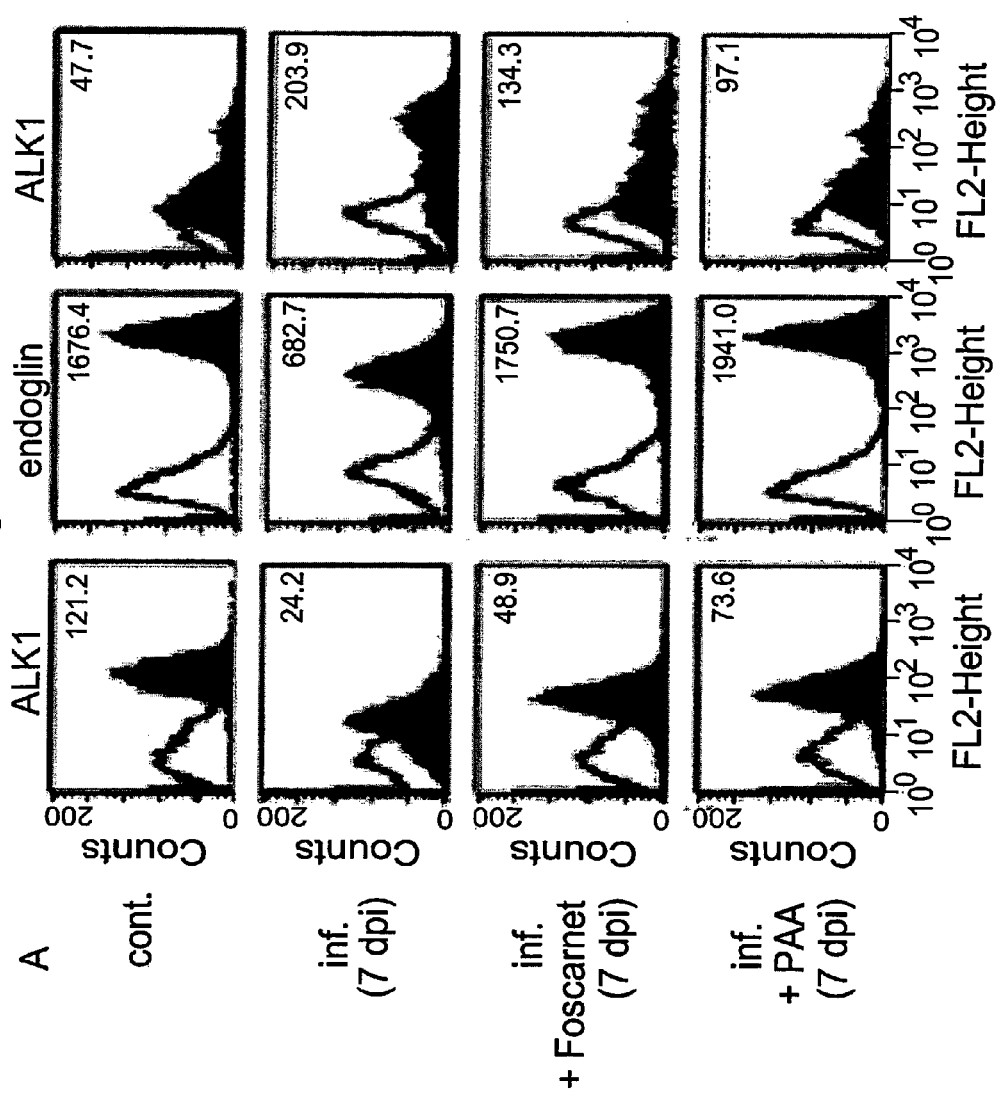

* End. cell = Endothelial cell

BIOMARKERS FOR PRENATAL DIAGNOSIS OF CONGENITAL CYTOMEGALOVIRUS

CROSS-REFERENCES TO RELATED APPLICATIONS

This application is a continuation of U.S. application Ser. No. 12/739,400 filed Aug. 20, 2010, which is a U.S. National Stage under 35 USC 371 of PCT/US2008/080815 filed Oct. 22, 2008, which claims priority to U.S. Provisional Patent Application No. 60/981,756 filed Oct. 22, 2007, the contents of each of which are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant Nos. AI46657 and AI53782 awarded by the National Institutes of Health. The Government has certain rights in this invention.

BACKGROUND OF THE INVENTION

Cytomegalovirus (CMV) is the leading viral cause of congenital birth defects in 1%-3% of live births in the United States. Half the mothers developing first-time infection during pregnancy will transmit virus to the fetus; 25% of newborns will have congenital disease and permanent birth defects.

Maternal low-avidity antibodies to CMV are a key indicator of possible fetal infection. ELISA assays to identify women at risk for primary maternal CMV infection are marketed by Radim (Italy) and BioMerieux (France) and other companies. These assays quantify maternal CMV IgG avidity for diagnosis of primary infection acquired during or shortly before gestation. Low-avidity antibodies indicate primary infection with 50% chance of fetal infection. However, women with moderate IgG avidity are not necessarily protected against congenital infection in the fetus, although damage is milder.

Transforming growth factor-β1 (TGF-β1), a multifunctional cytokine, plays a central role in cell proliferation, migration, and synthesis of extracellular matrix (ECM) in the endothelium (Lebrin et al., *Cardiovasc Res*, 65:599-608 (2005)). In most cell types, TGF-β1 signals through the type I receptor activin receptor-like kinase 5 (ALK5). In addition to expressing ALK5, endothelial cells express a second TGF-β1 receptor, the type I receptor ALK1. When activated, ALK1 induces phosphorylation of the nuclear effectors Smad 1 and Smad5, which promote endothelial cell proliferation and migration (Chen, Y. G. and Massague, J., *J Biol Chem*, 274:3672-3677 (1999)). In contrast, activated ALK5 induces Smad2 and Smad3 phosphorylation, leading to the inhibition of endothelial cell proliferation. TGF-β1 is secreted as an inactive, noncovalent complex with latency-associated peptide and requires activation before it can bind to its receptors. Reported mechanisms of TGF-β1 activation include cleavage by metalloproteinases or plasmin and binding to thrombospondin 1 or either of the integrins αvβ6 and αvβ8 (Lebrin et al., *Cardiovasc Res*, 65:599-608 (2005); Rifkin, D. B., *J Biol Chem*, 280:7409-7412 (2005); Munger et al., *Cell*, 96:319-328 (1999); Mu et al., *J Cell Biol*, 157:493-507 (2002); Crawford et al., *Cell*, 93:1159-11170 (1998); Annes et al., *J Cell Sci*, 116:217-224 (2003)). One of the in vivo activators of TGF-β1 is integrin αvβ6 (Rifkin, D. B., *J Biol Chem*, 280:7409-7412 (2005); Munger et al., *Cell*, 96:319-328 (1999)).

This activation model is particularly interesting because integrin αvβ6 is expressed principally on epithelial cells, which are very sensitive to TGF-β1-mediated growth inhibition. Integrin αvβ6 is strongly up-regulated at sites of epithelial repair and inflammation in lung and kidney (Breuss et al., *J Cell Sci*, 108:2241-2251 (1995)), and also because of the overlap of the phenotypes of TGF-β1 and integrin β6 subunit-deficient mice. Mice lacking the β6 subunit show increased inflammation and decreased fibrosis, both of which processes are strongly regulated by TGF-β1 (Munger et al., *Cell*, 96:319-328 (1999); Huang et al., *J Cell Biol*, 133:921-928 (1996); Hahm et al., *Am J Pathol*, 170:110-125 (2007)).

Recent work has provided evidence for the induction of TGF-β1 in a variety of cells and tissues on CMV infection. TGF-β1 was released in increasing amounts from splenocytes infected with rat CMV in vitro (Haagmans et al., *J Gen Virol*, 78:205-213 (1997)). TGF-β1 protein was increased in alveoli and stromal cells in rat lungs, spleen, and liver after radiation-induced immune suppression of CMV-infected rats (Haagmans et al., *J Gen Virol*, 78:205-213 (1997)). Furthermore, CMV infected murine astrocytes increased TGF-β1 transcription and protein levels (Kossmann et al., *J Infect Dis*, 187:534-541 (2003)). In human kidney allografts, CMV proteins and DNA were associated with locally increased TGF-β1 in tubuli and arterial endothelium long after viral clearance from the blood (Helantera et al., *Transplantation*, 79:379 (2005)). Brain biopsy specimens from AIDS patients with CMV encephalitis were found to contain viral inclusions that co-localized with TGF-β1 protein in cells with astrocyte-specific glial filaments (Kossmann et al., *J Infect Dis*, 187:534-541 (2003)). In addition, TGF-β1 induction in human fibroblasts has been shown to involve the transactivation of its promoter by immediate-early 2 protein through an Egr-1 consensus site by binding the zinc finger domain of Egr-1 (Michelson et al., *J Virol*, 68:5730-5737 (1994); Yoo et al., *J Viral*, 70:7062-7070 (1996)). Although the evidence suggests that TGF-β1 may be directly involved in CMV pathogenesis, little is known about the cellular proteins involved in virus-mediated TGF-β1 activation, or what specific functional role it plays in vivo. In recent experiments, it was found that a subpopulation of freshly isolated human cytotrophoblasts from term placentas expressed integrin αvβ6, which activates TGF-β1 in vitro (Tabata et al., *Placenta*, 28:527-537 (2007)).

Currently, there are no commercial assays to detect fetal infection early in gestation or to predict symptomatic disease. In women with primary CMV infection in first trimester, ultrasound at midgestation may identify fetuses with intrauterine growth restriction (IUGR) and other disease anomalies. But these may not be apparent unless severe (e.g. microcephaly and calcification in the brain). Detection of viral DNA by PCR following amniocentesis at 20-22 weeks gestation indicates fetal infection; very high levels may be associated with symptomatic fetal disease (Pereira et al., *J. Virol.* 77:13301-13314 (2003)). At birth, congenitally infected babies secrete infectious virus in urine, viral DNA can be quantified, and infectivity evaluated in plaque assays. Blood from infants with symptomatic disease contains many genome copies of CMV DNA (>10,000/ml).

Until recently, there was no therapy to prevent symptomatic congenital disease. Nigro et al. reported that CMV hyperimmune globulin (HIG) (Biotest, Germany) was an effective treatment that reduced congenital disease from 50% to 3% in infants of women with primary infection treated with intravenous HIG (*N Engl J Med* 353:1350-62 (2005)). Echodensities, anomalies associated with placental insufficiently and IUGR can resolve following HIG treatment. Moreover, when administered soon after maternal seroconversion, fetal infection is prevented. Clinical trials for congenital. CMV infection are ongoing and proposed. Thus, diagnostic tests for early detection of fetal infection and to indicate treatment efficacy are desperately needed. Quantitative assays for biomarkers of viral replication in amniotic fluid could identify candidates for treatment and reduced levels could be objective indicators of efficacy.

Accordingly, the invention provides biomarkers of CMV replication that are detectable in amniotic fluid and that permit early detection of congenital infection before symptomatic disease.

BRIEF SUMMARY OF THE INVENTION

The present invention demonstrates that elevated levels of sFlt1 can be detected in amniotic fluid of CMV-infected fetuses and in maternal sera. Additionally, a viral cytokine cmvIL-10, other viral cytokines and altered cellular proteins altered during CMV replication can be detected in the placental/fetal compartment. The discovery allows for early detection, prediction of fetal disease and determination of therapeutic efficacy.

In one aspect, the invention provides a method of diagnosing congenital cytomegalovirus (CMV) infection, the method comprising the steps of: (a) obtaining a biological sample from a subject; (b) contacting the biological sample with reagents that specifically bind to at least one CMV-associated marker selected from the group consisting of: Fms-like tyrosine kinase-1 (Flt-1; VEGFR-1), soluble Flt-1 (sFlt-1), vascular endothelial growth factor A (VEGF-A), placental growth factor (PlGF), CXC ligand-12 (CXCL-12; SDF-1), suppressor of cytokine signaling 3 (SOCS3), erythropoietin; transferrin, transforming growth factor (TGF) beta 3, TGF beta 1, endoglin, soluble endoglin (sEng), carcinoembryonic antigen-related cell adhesion molecule 1 (CEACAM1), IL-1 beta, IL-6, IL-8, IL-10, cmvIL-10, CMV ORF UL146 (v-CXC-1), integrin αvβ6, integrin β6 (ITGB6), integrin αv (ITGAV), transforming growth factor, beta receptor (TGFBR1/ALK5), activin receptor type II-like 1 (ACVRL1/ALK1), and pUS22; and (c) determining whether the marker is differentially expressed in the biological sample compared to a biological sample from a non-infected subject; thereby providing a diagnosis for congenital CMV infection.

In another aspect, the invention provides a method of predicting congenital cytomegalovirus (CMV) disease, the method comprising the steps of: (a) obtaining a biological sample from a subject; (b) contacting the biological sample with reagents that specifically bind to at least one CMV-associated marker selected from the group consisting of: Fms-like tyrosine kinase-1 (Flt-1; VEGFR-1), sFlt-1, vascular endothelial growth factor A (VEGF-A), placental growth factor (PlGF), CXC ligand-12 (CXCL-12, SDF-1), suppressor of cytokine signaling 3 (SOCS3), erythropoietin; transferrin, TGF beta 3, TGF beta 1, endoglin, soluble endoglin (sEng), CEACAM1, IL-1 beta, IL-6, IL-8, IL-10, cmvIL-10, CMV ORF UL146 (v-CXC-1), integrin αvβ6, integrin β6 (ITGB6), integrin αv (ITGAV), transforming growth factor, beta receptor (TGFBR1/ALK5), activin receptor type II-like 1 (ACVRL1/ALK1), and pUS22; and (c) determining whether the marker is differentially expressed in the biological sample compared to a biological sample from a non-infected subject; thereby predicting congenital CMV disease.

In another aspect, the invention provides a kit comprising reagents that specifically bind to a panel of CMV-associated markers, wherein the kit comprises one or more reagents that bind to one or more markers selected from the group consisting of Fms-like tyrosine kinase-1 (Flt-1; VEGFR-1), sFlt-1, vascular endothelial growth factor A (VEGF-A), placental growth factor (PlGF), CXC ligand-12 (CXCL-12, SDF-1), suppressor of cytokine signaling 3 (SOCS3), erythropoietin; transferrin, TGF beta 3, TGF beta 1, endoglin, soluble endoglin (sEng), CEACAM1, IL-1 beta, IL-6, IL-8, IL-10, cmvIL-10, CMV ORF UL146 (v-CXC-1), integrin αvβ6, ITGB6, ITGAV, TGFBR1/ALK5, ACVRL1/ALK1, and pUS22.

In another aspect, the invention provides a method of determining the efficacy of therapy for congenital cytomegalovirus (CMV) infection, the method comprising the steps of: (a) obtaining a biological sample from a subject; (b) contacting the biological sample with reagents that specifically bind to at least one CMV-associated marker selected from the group consisting of: Fms-like tyrosine kinase-1 (Flt-1; VEGFR-1), sFlt-1, vascular endothelial growth factor A (VEGF-A), placental growth factor (PlGF), CXC ligand-12 (CXCL-12, SDF-1), suppressor of cytokine signaling 3 (SOCS3), erythropoietin; transferrin, TGF beta 3, TGF beta 1, endoglin, soluble endoglin (sEng), CEACAM1, IL-1 beta, IL-6, IL-8, IL-10, cmvIL-10, CMV ORF UL146 (v-CXC-1), integrin αvβ6, integrin β6 (ITGB6), integrin αv (ITGAV), transforming growth factor, beta receptor (TGFBR1/ALK5), activin receptor type II-like 1 (ACVRL1/ALK1), and pUS22; (c) determining whether the marker is differentially expressed in the biological sample compared to a biological sample obtained from the subject at an earlier time; thereby determining the efficacy of therapy.

In one embodiment, the method is repeated at least once. In another embodiment, the method further comprises adjusting the therapy based on the determination of efficacy.

In one embodiment, the reagent is an antibody. In another embodiment, the antibody is monoclonal. In another embodiment, the determining step comprises an enzyme-linked immunosorbant assay (ELISA). In another embodiment, the determining step comprises an mass spectroscopy.

In one embodiment, the reagent is a nucleic acid. In another embodiment, the reagent is a PCR primer.

In one embodiment, the determining step comprises PCR. In one embodiment, the reagent is detectably labeled.

In one embodiment, the invention provides a method of determining the efficacy of therapy for congenital cytomegalovirus (CMV) infection, the method comprising the steps of: (a) obtaining a biological sample from a subject; (b) subjecting the biological sample to a therapy for congenital cytomegalovirus (CMV) infection, and (c) determining if a CMV-associated marker is differentially expressed in said sample subjected to therapy, as compared to a sample from the same individual that is not subjected to therapy, thereby determining the efficacy of therapy.

In one embodiment, the determining step comprises detecting increased expression of a marker selected from the group consisting of: Flt-1, sFlt-1, sEng, and cmvIL-10, integrin αvβ6, ITGB6, ITGAV, and TGFBR1/ALK5. In another embodiment, the determining step comprises detecting reduced expression of a marker selected from the group consisting of: VEGF, PlGF, ACVRL1/ALK1, and SDF-1.

In one embodiment, the biological sample is amniotic fluid. In another embodiment the biological sample is selected from the group consisting of: breast milk, maternal blood, maternal urine, maternal saliva, fetal blood, fetal blood from the umbilical cord, postnatal infant urine, blood, saliva, a uterine biopsy sample, and a placental biopsy.

In one embodiment, the step of determining whether markers are differentially expressed in the biological sample compared to a biological sample from a non-infected subject comprises detecting VEGF-A, sFlt-1, PlGF, and cmvIL-10.

In another embodiment, the step of determining whether markers are differentially expressed in the biological sample compared to a biological sample from a non-infected subject comprises detecting SOCS3, IL-10, cmvIL-10 and SDF-1. In another embodiment, the step of determining whether markers are differentially expressed in the biological sample compared to a biological sample from a non-infected subject comprises detecting CEACAM-1, IL-8, erythropoietin, transferrin, TGF beta, and endoglin. In another embodiment, the step of determining whether markers are differentially expressed in the biological sample compared to a biological sample from a non-infected subject comprises detecting IL-1 beta, IL-6, IL-8, vCXC-1, and pUS22. In yet another embodiment, the step of determining whether markers are differentially expressed in the biological sample compared to a biological sample from a non-infected subject comprises detecting integrin $\alpha v \beta 6$.

In one embodiment, the step of determining whether markers are differentially expressed in the biological sample compared to a biological sample from a non-infected subject comprises detecting sFlt-1 and PlGF, calculating a ratio of sFlt-1 expression to PlGF expression (sFlt-1/PlGF ratio) for the biological sample and for the biological sample from the non-infected subject, and comparing the sFlt-1/PlGF ratio for the biological sample to the sFlt-1/PlGF ratio for the biological sample from the non-infected subject.

In another embodiment, the step of determining whether markers are differentially expressed in the biological sample compared to a biological sample from a non-infected subject comprises detecting TGFBR1/ALK5 and ACVRL1/ALK1, calculating a ratio of TGFBR1/ALK5 expression to ACVRL1/ALK1 expression (ALK5/ALK1 ratio) for the biological sample and for the biological sample from the non-infected subject, and comparing the ALK5/ALK1 ratio for the biological sample to the ALK5/ALK1 ratio for the biological sample from the non-infected subject.

In another embodiment, the present invention provides a method of diagnosing congenital cytomegalovirus (CMV) infection or disease, the method comprising the steps of: (a) obtaining a biological sample from a subject; (b) determining the level of phosphorylation of at least one CMV-associated marker selected from Smad3, Smad1, and Smad5; and (c) determining whether the marker is differentially phosphorylated in the biological sample compared to a biological sample from a non-infected or non-diseased subject; thereby providing a diagnosis for congenital CMV infection or disease. In a particular embodiment, the CMV-associated marker is Smad3. In another embodiment, the invention provides a method of determining the efficacy of therapy for congenital cytomegalovirus (CMV) infection, comprising determining the level of phosphorylation of at least one CMV-associated marker selected from Smad3, Smad1, and Smad5 in a sample subjected to therapy, as compared to the level of phosphorylation in a sample not subjected to therapy.

BRIEF DESCRIPTION OF THE DRAWINGS

FIG. 3 demonstrates quantification of sFlt1, VEGF and PlGF levels in conditioned media and lysates of CMV VR1814-infected HUVEC using ELISA. Secreted sFlt1 increased rapidly and remained high during infection (Panel A). Levels of bound VEGF in complexes with sFlt1 also increased in conditioned medium (Panel B). Trace amounts of PlGF were found (Panel B) but free VEGF was not detected. ELISA purchased from R&D systems (sFlt1, PlGF) and Chemicon International (VEGF).

DETAILED DESCRIPTION OF THE INVENTION

Figure 1:
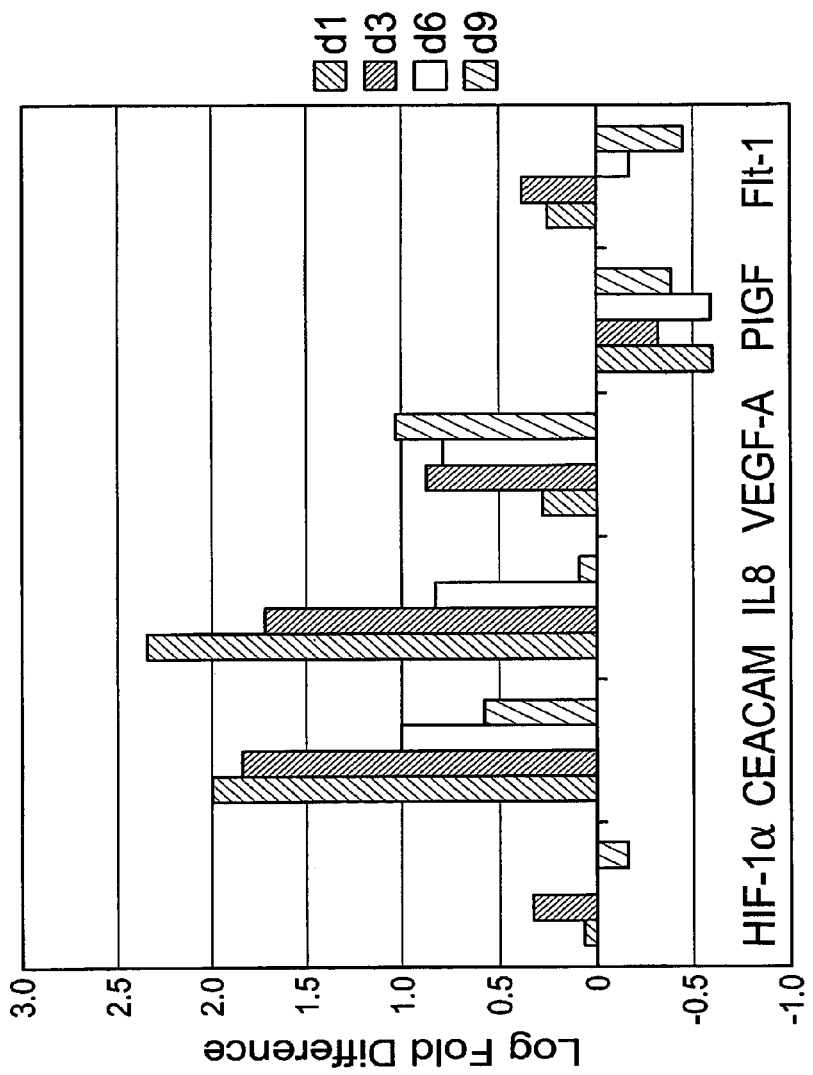
FIG. 1 shows that the expression of hypoxia induced genes is altered in Human Umbilical Vein Endothelial. Cells (HUVEC) infected with a pathogenic clinical strain of CMV, called VR1814.

Biomarkers of congenital CMV infection include Fms-like tyrosine kinase-1 (Flt-1; VEGFR-1), soluble Flt-1 (sFlt-1), vascular endothelial growth factor A (VEGF-A), placental growth factor (PlGF), CXC ligand-12 (CXCL-12; SDF-1), suppressor of cytokine signaling 3 (SOCS3), erythropoietin; transferrin, transforming growth factor (TGF) beta 3, TGF beta 1, endoglin, soluble endoglin (sEng), carcinoembryonic antigen-related cell adhesion molecule 1 (CEACAM1), IL-1 beta, IL-6, IL-8, IL-10, v-CXC-1, cmvIL-10, CMV ORF UL146, integrin αvβ6, integrin β6 (ITGB6), integrin αv (ITGAV), transforming growth factor, beta receptor (TGFBR1/ALK5), activin receptor type II-like 1 (ACVRL1/ALK1), Smad3, Smad1, Smad5, and pUS22. These markers can be used alone or in various combinations, depending on the sample used. Quantification of cellular and viral factors can be achieved in a variety of biological fluids derived from either the mother or the fetus, including amniotic fluid, cord blood, fetal blood, fetal urine, fetal saliva, maternal blood, maternal urine, maternal saliva, and breast milk. These markers therefore constitute novel tests for diagnosis of congenital infection in early gestation (and persistent intrauterine infection). The markers are also useful as prognostic indicators and as assays for drug efficacy (e.g., hyperimmune globulin, valaciclovir). For example, both drug dose and choice of therapeutic agent can be monitored using these assays. Vaccine efficacy can also be tested, e.g., a subunit vaccine. The prognositic assay would also provide additional, earlier information in the case that the pregnancy may be terminated. Useful assay formats include ELISA, PCR, and mass spectroscopy. These markers can also be used in combination with other tests such as viral DNA, IgG/IgM avidity, ultrasound, chorionic villus sampling, amniocentesis, and cordocentisis.

Biomarkers thus have, but are not limited to, the following uses: CMV biomarkers can be measured in serum of seropositive mothers to identify fetuses with congenital infection and potential for symptomatic disease. Biomarkers can be used to evaluate efficacy of CMV vaccines to prevent maternal and fetal infection. Biomarkers can be used to determine the efficacy of hyperimmune globulin treatment to prevent fetal infection after maternal seroconversion. Biomarkers could be used to identify mothers who seroconvert between pregnancies as a means of counseling women about a safe interval for conception. There is evidence that virus continues to replicate in the uterine wall of women who deliver healthy babies without maternal symptoms. It may be unsafe to conceive for several years after CMV seroconversion between pregnancies. Biomarkers can be used to identify women shedding CMV in breast milk who could transmit virus to seronegative babies causing primary infection and disease. Biomarkers can be used to identify women with congenital CMV infection (3% of population) as distinct from women with the pregnancy disorder preeclampsia (5-7% of population) based on viral cytokines, cmvIL-10, chemokines, and endoglin levels. Biomarkers could be used to identify women with ultrasound abnormalities from congenital CMV infection after routine screening. Biomarkers could be used for prenatal genetic testing of women for inherited disorders in conjunction with chorionic villus sampling. Biomarkers could be used to exclude or identify intrauterine infection as a complication of infertility for treatment of women prior to the fertility treatment. (Could be used to select surrogate mothers). Biomarkers could be used to identify congenital CMV infection as a cause of spontaneous abortions, premature deliveries and fetal demise. Biomarkers can be used to identify women with Mirror syndrome, preeclampsia and fetal hydrops caused by congenital CMV infection.

Definitions

Cytomegalovirus (CMV) refers to a herpes virus that, like other members of the family, has the ability to remain latent in the body for many years. CMV infection is the leading cause of birth defects in the U.S.

As used herein, "congenital CMV disease," "symptomatic congenital CMV disease," "birth defects," and like terms refer to symptoms and syndromes associated with congenital CMV infection. Congenital CMV infection refers to the in utero transmission of CMV infection from mother to fetus. Symptoms may be observed in the mother or the fetus. Maternal symptoms include fever and flu-like symptoms. Fetal symptoms include, but are not limited to: intrauterine growth restriction (IUGR), calcification of the brain, microcephaly, enlargement of the liver and spleen, hearing loss, vision impairment, varying degrees of mental retardation and coordination problems. In extreme cases, maternal preeclampsia including symptoms of edema and proteinuria that mirror fetal hydrops.

The terms "marker" and "biomarker" refer to a molecule (typically protein, nucleic acid, carbohydrate, or lipid) that is differentially expressed in the cell, differentially expressed on the surface of an infected cell, differentially phosphorylated, or differentially secreted by a infected cell in comparison to a normal cell or in a paracrine fashion by neighboring uninfected cells, and which is useful for the diagnosis of congenital CMV infection, for providing a prognosis for birth defects, and for preferential targeting of a pharmacological agent to an infected fetus or individual. Oftentimes, such markers are molecules that are overexpressed in an infected cell in comparison to a normal cell, for instance, 1-fold overexpression, 2-fold overexpression, 3-fold overexpression or more in comparison to a normal cell. Alternatively, such biomarkers are molecules that are underexpressed in a infected cell in comparison to a normal cell, for instance, 1-fold underexpression, 2-fold underexpression, 3-fold underexpression, or more. Alternately, such biomarkers are produced by uninfected cells or tissues, resulting from local infection or damage and protein fragments are secreted from cells or released by proteolytic processing from the plasma membrane. Further, a marker can be a molecule that is inappropriately synthesized in the infected cell, for instance, a molecule that contains deletions, additions or mutations in comparison to the molecule expressed on a normal cell. A marker can also be a molecule that is inappropriately processed in infected cells, for instance, a molecule that is secreted, proteolytically processed or subject to post-translational modification (e.g., phosphorylation, glycosylation) in comparison to the molecule expressed on a normal cell. Likewise, biomarkers could be released by hypoxic cells in the uterus, placenta and fetus. Probes to detect the biomarkers detect naturally occurring human and CMV alleles and variants. The alleles and variants typically have at least about 85%, or at least about 90%, 95%, 96%, 97%, 98%, 99%, or more identity to the reference sequence for the marker provided below.

Biomarkers of the invention include: Fms-like tyrosine kinase-1 (Flt-1; VEGFR-1, Genebank Accession No. AAH39007), soluble Flt-1 (sFlt-1), vascular endothelial growth factor A (VEGF-A, Genebank Accession No. AAH65522), placental growth factor (PlGF, Genebank Accession No. P49763), CXC ligand-12 (CXCL-12; SDF-1, Genebank Accession No. AAV49999), suppressor of cytokine signaling 3 (SOCS3, Genebank Accession No. CAG46495), erythropoictin (Genebank Accession No. NP_000790); transferrin (Genebank Accession No. P02787), transforming growth factor (TGF) beta 3 (Genebank Accession No. ABQ59024), TGF beta 1 (Genebank Accession No. NP_000651), endoglin (Genebank Accession No. FLJ41744), soluble endoglin (sEng), carcinoembryonic antigen-related cell adhesion molecule 1 (CEACAM1, Genebank Accession No. AAH24164), IL-1 beta (Genebank Accession No. NP_000567), IL-6 (Genebank Accession No. NP_000591), IL-8 (Genebank Accession No. AAH13615), IL-10 (Genebank Accession No. NP_000563), cmvIL-10 (Genebank Accession No. P17150), CMV ORF UL146 (v-CXC-1) (Genebank Accession No. AAA85885), integrin αvβ6, integrin β6 (ITGB6) (Genebank Accession No. NP_000879), integrin αv (ITGAV) (Genebank Accession No. NP_002201), transforming growth factor, beta receptor (TGFBR1/ALK5) (Genebank Accession No. NP_004603), activin receptor type II-like 1 (ACVRL1/ALK1) (Genebank Accession No. NP_000011), Smad3 (Genebank Accession No. NP_005893), Smad1 (Genebank Accession No. AAC50790), Smad5 (Genebank Accession No. AAB92396), and pUS22 (Genebank Accession No. AAS49020).

It will be understood by the skilled artisan that markers may be used in combination with other markers or tests for any of the uses, e.g., prediction, diagnosis, or prognosis of CMV infection or birth defects, as disclosed herein.

As used herein, a "biological sample" may be either cellular or acellular. Biological samples include: amniotic fluid, sections of tissues (e.g., biopsies, autopsy samples, and frozen sections taken for histologic purposes), blood and blood fractions or products (e.g., serum, plasma, platelets, red blood cells, and the like), saliva, tears, semen, breast milk, sputum, cervical tissue, placental tissue, uterine tissue, fetal cells, cultured cells (e.g., primary cultures, explants, and transformed cells), stool, or urine.

A biological sample is typically obtained from a eukaryotic organism, most preferably a mammal such as a primate e.g., chimpanzee or human; cow; dog; cat; a rodent (e.g., guinea pig, rat, mouse); rabbit; bird; reptile; or fish. It will be understood that, in the context of the present invention, the biological sample will be obtained from a subject, wherein the subject can be a pregnant woman, a woman suspected of being pregnant, a postpartum mother, a fetus, or a control individual.

As used herein, "amniocentesis" refers to removal of a small amount of amniotic fluid from the amniotic sac surrounding a fetus. The amniotic fluid is a source of fetal cells that can be subjected to testing, e.g., for genetic abnormalities or aberrant gene expression or CMV DNA. Generally the procedure is performed using a long syringe and guided by ultrasound.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., placental or fetal tissue). Representative biopsy techniques include, but are not limited to, excisional biopsy, incisional biopsy, needle biopsy, surgical biopsy, and bone marrow biopsy. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "overexpress," "overexpression," "overexpressed" (or induced) interchangeably refer to a protein or nucleic acid (RNA) that is transcribed or translated at a detectably greater level, usually in an infected cell, in comparison to a normal cell or in a paracrine mechanism by normal cells. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "underexpress," "underexpression" or "underexpressed" or "downregulated" interchangeably refer to a protein or nucleic acid that is transcribed or translated at a detectably lower level in an infected cell, in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques, and immunoblot techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated, induced) or underexpressed (downregulated, degraded) in one sample compared to at least one other sample, generally in an infected patient, in comparison to an uninfected individual, in the context of the present invention.

The term "differentially phosphorylated" refers generally to a protein that is phosphorylated at a higher level (hyperphosphorylated) or phosphorylated at a lower level (hypophosphorylated) in one sample, for example in biological sample from an individual or infected with CMV, as compared to a second or reference sample, for example in a biological sample or cell from an individual who is not infected with CMV. A hypophosphorylated protein may be, for example, at least about 1-fold less phosphorylated, or at least about 2-fold, 3-fold, 4-fold, or more fold less phosphorylated in a first sample, for example, in an individual infected with CMV, as compared to a second sample, for example, in an individual that is not infected with CMV. In other embodiments, a hypophosphorylated protein may be at least about 10-fold, at least about 100-fold, or at least about 1,000-fold less phosphorylated in a first sample as compared to a second sample. A hyperphosphorylated protein may be, for example, at least about 1-fold more phosphorylated, or at least about 2-fold, 3-fold, 4-fold, or more phosphorylated in a first sample, for example, in an individual infected with CMV, as compared to a second sample, for example, in an individual that is not infected with CMV. In other embodiments, a hyperphosphorylated protein may be at least about 10-fold, at least about 100-fold, or at least about 1,000-fold more phosphorylated in a first sample as compared to a second sample.

"Therapeutic treatment" and "antiviral therapies" refers to treatment with CMV hyperimmune globulin (HIG), passive administration of immunoglobin, IVIG, immunotherapy, biologic (targeted) therapy, and the like.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. The biomarkers described herein can be detected with probes that have, e.g., more than 70% identity over a specified region, or more than 80% identity, or more than 90% identity to the reference sequence provided by the accession number, up to 100% identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Set. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 60° C., or about 60 C to 70 C, depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)$'_2$, a dimer of Fab which itself is a light chain joined to $V_H$-$C_H$1 by a disulfide bond. The F(ab)$'_2$ may be reduced under mild conditions to break the disulfide linkage in the hinge region, thereby converting the F(ab)$'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

A phospho-specific antibody generally refers to an antibody that preferentially binds to a phosphorylated polypeptide as compared to an unphosphorylated polypeptide. Phospho-specific antibodies can be used to determine the phosphorylation level of a protein in a biological sample. Phospho-specific antibodies may be specific for a particular phosphorylated polypeptide sequence, a particular phosphorylated protein, or a particular phosphorylated residue or motif of residues that comprises at least one phosphorylated residues.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster, cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical reaction, change in expression, or particular phenotype. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker, measuring changes in enzymatic activity; the ability to increase or decrease cellular proliferation and migration (e.g., neovascularization), apoptosis, hypoxia, or cell cycle arrest; measuring changes in cell surface markers and extracellular matrix deposition/fibrosis. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of congenital CMV infection biomarkers. Inhibitors are compounds that, e.g., bind to, partially or totally block activity, decrease, prevent, delay activation, inactivate, desensitize, or down regulate the activity or expression of congenital CMV infection biomarkers. "Activators" are compounds that increase, open, activate, facilitate, enhance activation, sensitize, agonize, or up regulate activity of congenital CMV infection biomarkers, e.g., agonists. Inhibitors, activators, or modulators also include genetically modified versions of congenital CMV infection biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing congenital CMV infection biomarkers in vitro, in cells, or cell extracts, applying putative modulator compounds, and then determining the functional effects on activity, as described above.

Samples or assays comprising congenital CMV infection biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of congenital CMV infection biomarkers is achieved when the activity value relative to the control is about 80%, preferably 50%, more preferably 25-0%. Activation of congenital CMV infection biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate congenital CMV infection biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Predictive, Diagnostic, and Prognostic Methods

The present invention provides methods of predicting, diagnosing or providing prognosis of congenital CMV infection by detecting the expression of markers differentially expressed, or the level of phosphorylation of markers differentially phosphorylated in congenital CMV infection. Prediction and diagnosis involve determining the level of a panel of congenital CMV infection biomarker polynucleotide or the corresponding polypeptides in a patient or patient sample and then comparing the level to a baseline or range. Similarly, prediction and diagnosis may additionally or alternatively involve the detection of the level of phosphorylation of a of one or more marker proteins in a patient or patient sample and then comparing the level to a baseline or range. Typically, the baseline value is representative of levels of the polynucleotide or nucleic acid, or the level of phosphorylation, in a healthy person not suffering from, or destined to develop, congenital CMV infection, as measured using a biological sample such as amniotic fluid or blood serum. Variation of levels of a polynucleotide or corresponding polypeptides, or of the level of phosphorylation, of the invention from the baseline range (either up or down) indicates that the patient has an increased risk of developing congenital CMV disease. One or more biomarkers is used to detect congenital CMV infection, including without limitation, Fms-like tyrosine kinase-1 (Flt-1; VEGFR-1), soluble Flt-1 (sFlt-1), vascular endothelial growth factor A (VEGF-A), placental growth factor (PlGF), CXC ligand-12 (CXCL-12; SDF-1), suppressor of cytokine signaling 3 (SOCS3), erythropoietin; transferrin, transforming growth factor (TGF) beta 3, TGF beta 1, endoglin, soluble endoglin (sEng), carcinoembryonic antigen-related cell adhesion molecule 1 (CEACAM1), IL-1 beta, IL-6, IL-8, IL-10, v-CXC-1, cmvIL-10, integrin $\alpha v \beta 6$, ITGB6, ITGAV, TGFBR1/ALK5, ACVRL1/ALK1, Smad3, Smad1, Smad5, and pUS22.

As used herein, the term "diagnosis" refers to detecting congenital CMV infection and/or distinguishing between congenital CMV infection and symptomatic congenital CMV disease. As used herein, the term "providing a prognosis" refers to providing a prediction of the probable course and outcome of the diagnosis.

Antibody reagents can be used in assays to detect expression levels of the biomarkers of the invention, or the level of phosphorylation of a biomarker of the invention, in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to nucleic acids can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), $\beta$-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, $\beta$-galactosidase detection system can be used with the chromogenic substrate o-nitrophenyl-$\beta$-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper, nitrocellulose), and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression in patient samples (e.g., reverse-transcriptase prolymerase chain reaction). In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected biomarkers can be prepared according to methods known to those of skill in the art or purchased commercially.

Analysis of nucleic acids can be achieved using routine techniques such as Southern blot analysis, PCR, Northern blot analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, case of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

Many correlation methodologies may be employed for the comparison of both individual biomarker levels and multi-biomarker profiles in the present invention. Non-limiting examples of these correlation methods include parametric and non-parametric methods as well as methodologies based on mutual information and non-linear approaches. Examples of parametric approaches include without limitation, Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the levels of individual biomarkers in the data set. The correlation of the level of all biomarkers with all other biomarkers is most readily considered as a matrix.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by congenital CMV infection biomarkers, such as antibodies, may be labeled using an appropriate marker, such as a fluorescent marker.

Compositions, Kits, and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Methods of Identifying Compounds

A variety of methods may be used to identify compounds that prevent or treat congenital CMV infection and/or onset of disease. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of a biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds is possible using the integrated systems of the invention.

Methods to Inhibit Marker Protein Expression

A variety of nucleic acids, such as antisense nucleic acids, siRNAs or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

Fisher et al. reported that infected cytotrophoblasts in human placenta were impaired in differentiation molecules that resembled the pregnancy disorder preeclampsia (PE) with reduced integrin expression and impaired cell invasiveness (*J. Virol.* 74:6808-6820 (2000)). These defects are associated with poor vascular remodeling, reduced placental perfusion in utero. Ultimately a hypoxic environment results as fetal demands for oxygen increase at midgestation and the maternal vasculature is affected by anti-angiogenic factors from the placental/fetal unit. Preterm delivery is required in severe cases after which maternal symptoms usually disappear. CMV could play a role in PE since the disorder is also associated with sexually transmitted disease, which includes CMV.

Biopsy specimens from placentas with PE were examined for CMV proteins (unpublished). Viral replication proteins were found in nuclei of fetal macrophages in the villous core and endothelial cells in the placental/fetal vasculature, suggesting active replication. Sera analysis (Virolab) from mothers with PE revealed that some had high CMV antibody titers but the numbers were not significantly different from healthy controls. This was expected because PE is a multifactorial disorder with a genetic component (Fisher 2004, *Reprod Biol Endocrinol*). Subsequently, we found CMV virion proteins and DNA in more than half the placentas from uncomplicated pregnancies we studied (McDonagh et al. (2004) *J. Infect. Dis.* 190:826-834; Pereira et al. (2003) *J. Virol.* 77:13301-13314). Although we could not directly connect intrauterine CMV infection with PE, other groups identified dysregulated vascular growth factors in PE (Zhou et al. (2002) *Am J Pathol* 160:1405-23). A soluble factor, vascular endothelial growth factor (VEGF) receptor sFlt1 was identified and provided a clue to vascular dysregulation (Maynard et al. (2003) *J Clin Invest* 111:649-58). sFlt1 was also quantified in human sera (Maynard et al. (2005) *Pediatr Res* 57:1R-7R). We investigated whether endothelial cells infected with a pathogenic clinical CMV strain altered expression of growth factors VEGF, PlGF and their receptors (Flt1, KDR) in vitro.

We found that CMV-infected cytotrophoblasts and uterine microvascular endothelial cells infected with a pathogenic clinical CMV strain (VR1814) upregulate transcription of VEGF and the receptor Flt1. We confirmed that human umbilical vein endothelial cells (HUVEC) induce Flt1 transcription. See FIG. 1.

Figure 2:
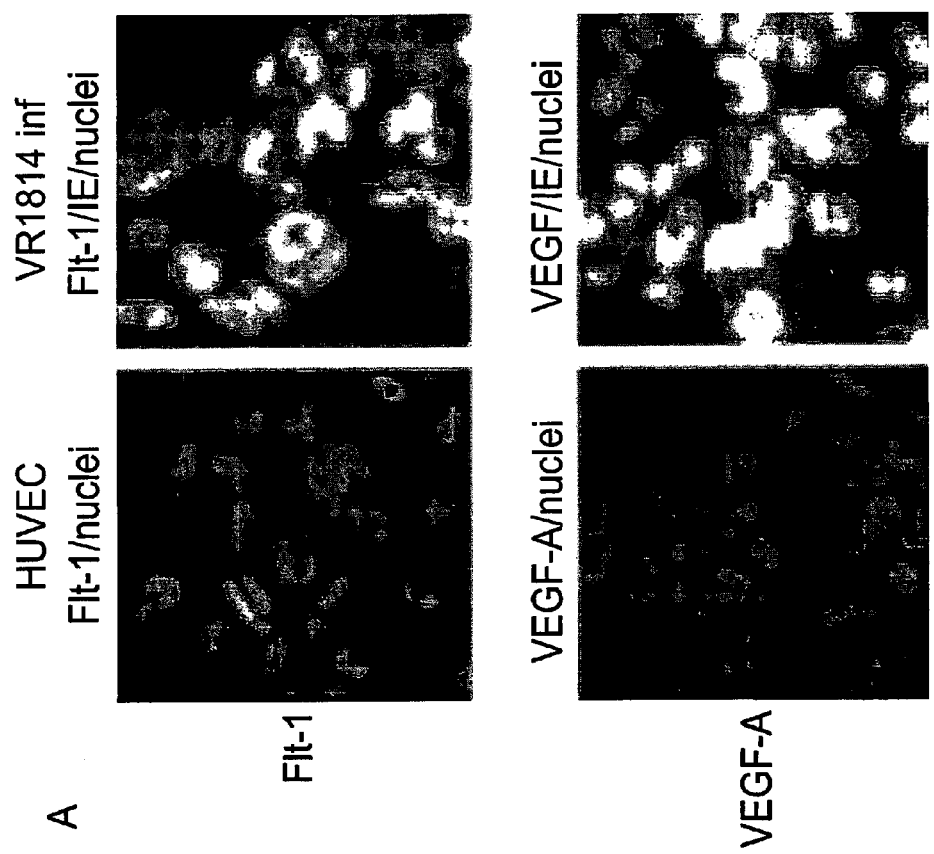
FIG. 2 demonstrates upregulated Flt-1, VEGF-A and PlGF proteins in infected endothelial cells. (A) Immunofluorescence staining of control and VR1814 infected (7 dpi) HUVEC for Flt-1 (green), VEGF-A (green), CMV IE1/2 (red), and TO-PRO-3 iodide for nuclei (blue). Infected cells express Flt-1 and VEGF-A. (B) immunoblot of control and infected (7 dpi) HUVEC incubated with anti-Flt-1 antibody and Grb2 (loading control). (C) Lysates from control and infected HUVEC (10 dpi) and recombinant VEGF-A (rVEGF) were immunoblotted with anti-VEGF-A antibody. (D) Immunoblot of conditioned media from serum-starved control and infected HUVEC (9 dpi). Concentrated media were electrophoresed in non-reducing gels and immunoblotted with antibodies to Flt-1, VEGF-A, and PlGF. Labeled bands indicate: D, receptor dimer and ligand complex; M, receptor monomer-ligand complex; H, ligand-homodimer complex; VEGF alone.

The kinetics of Flt1 expression in infected HUVEC indicated that Flt1 protein increased after infection. Flt1 increased as infection proceeded and a protein antigenically related to the membrane-bound form of Flt1 protein, likely sFlt1, accumulated in media of CMV-infected HUVEC. These studies, shown in FIG. 2, were carried out using immunoblot analysis.

We then studied protein expression of growth factors and their inhibitors to examine the underlying molecular changes in placentas from congenital CMV infection that was reversed by HIG treatment of mothers with primary CMV infection. We found considerable damage from large fibrinoids and many infected villi lacked cell structure and fetal blood vessels. A high level of syncytial knotting, often associated with fetal IUGR, hypoxia and PE was detected. Placentas from HIG-treated women developed small villi over the placenta surface. Immunohistochemical analysis showed infected placentas strongly expressed vascular endothelial growth factor (VEGF-A) a key regulator of angiogenesis in contrast to healthy term placentas. These results indicate that placental CMV infection could induce inhibitors of placental development.

Example 1

Growth Factors and Inhibitors Induced in CMV-infected Human Umbilical Vein Endothelial Cells (HUVEC) In Vitro We quantified levels of vasculogenic factors—VEGF, PlGF and sFlt1, a secreted form of the receptor—that regulate vascular development in conditioned media in vitro. We found these factors were induced in HUVEC infected with a pathogenic CMV strain VR1814 (FIG. 3A). In addition, secreted VEGF and PlGF were sequestered in complexes with sFlt1 that reduced free levels, especially VEGF (FIG. 3B).

Example 2

Quantitative Analysis of sFlt1 Concentration in Maternal Sera and Amniotic Fluids Obtained from Fetuses Diagnosed with Congenital CMV Infection, Before Treatment, and after HIG Prevention Infected placental/fetal vasculature induces sFlt1 detected in the fetal compartment. CMV transmission and congenital infection correlate with increased sFlt-1 in amniotic fluids in ELISA assays to quantify vasculogenic factors in the fetal compartment and maternal circulation in pregnancies with congenital CMV infection. Specifically, we measured the concentration of sFlt1, an inhibitor of angiogenesis that inactivates VEGF and PlGF. Although the numbers of amniotic fluids tested were not equally distributed among the groups, the data were immediately convincing. Dramatic increases in sFlt1 levels were found in amniotic fluids (Table 1). These samples had been used by Dr. Nigro to confirm congenital infection by detection of CMV DNA. Even samples from infected fetuses that were negative for viral DNA by PCR contained very high sFlt1 concentrations, far exceeding amounts in maternal sera (not shown). Remarkably, after HIG-prevention, sFlt1 in amniotic fluid decreased to levels in healthy control pregnancies (Table 1; healthy pregnancies also see Park et al, *J Obstet Gynecol* 193:984-9 (2005)). High sFlt1 concentrations could reflect the extent of placental involvement and severity of fetal infection and serve to identify early gestation pregnancies in need of treatment.

Figure 4:
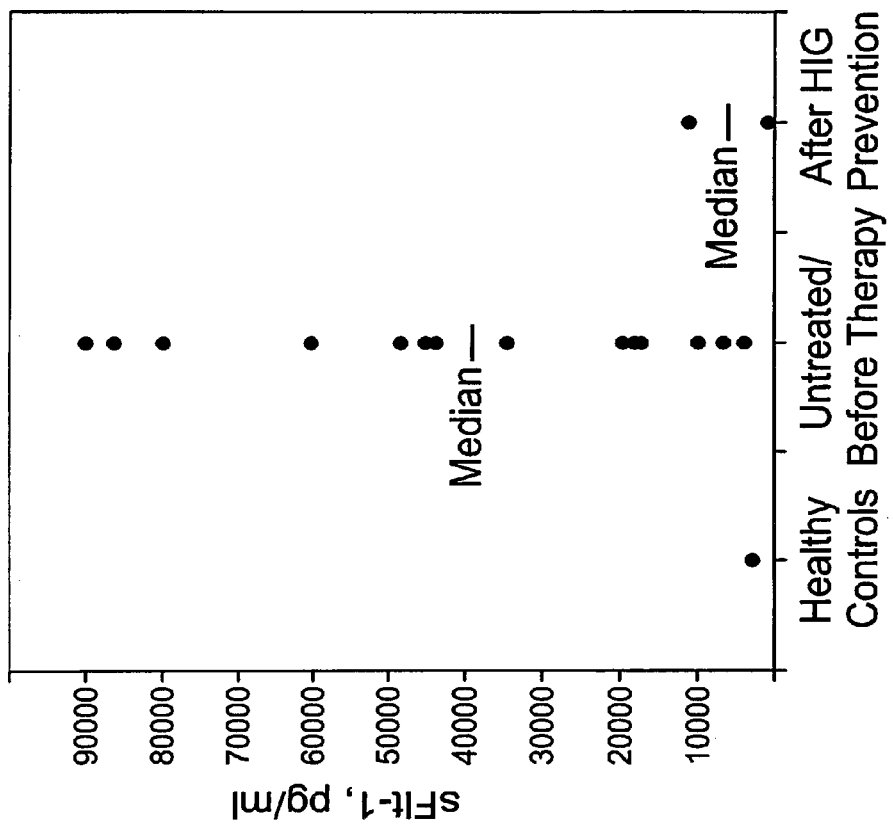
FIG. 4 summarizes sFlt1 levels and median values from amniotic fluid samples of healthy controls, untreated, and HIG-treated individuals. Amniotic fluids from pregnancies with untreated congenital CMV infection contain high sFlt1 levels, which are reduced after HIG prevention.
Figure 5:
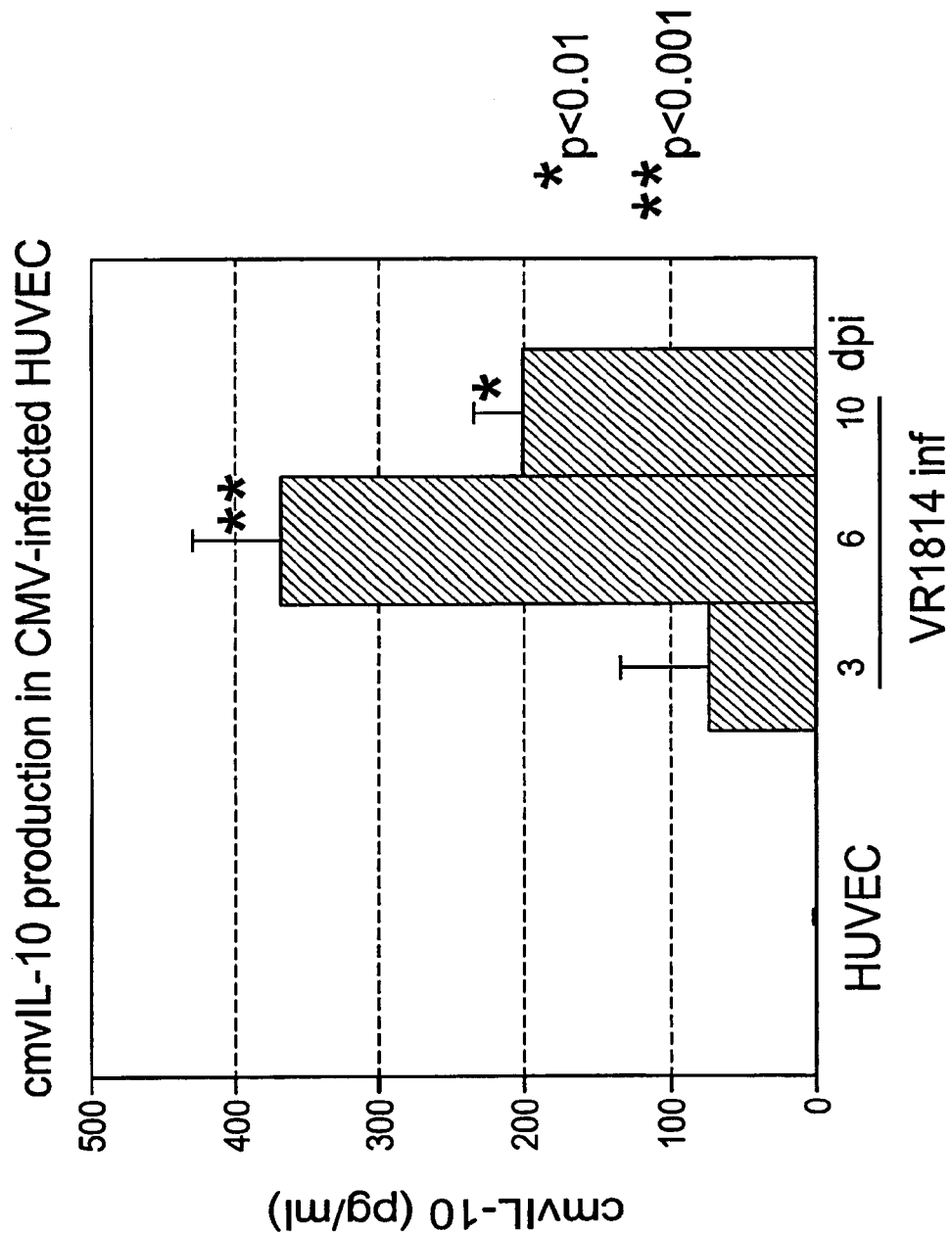
FIG. 5 is a bar graph illustrating that cmvIL10 is increased in CMV-infected HUVEC.
Figure 6:
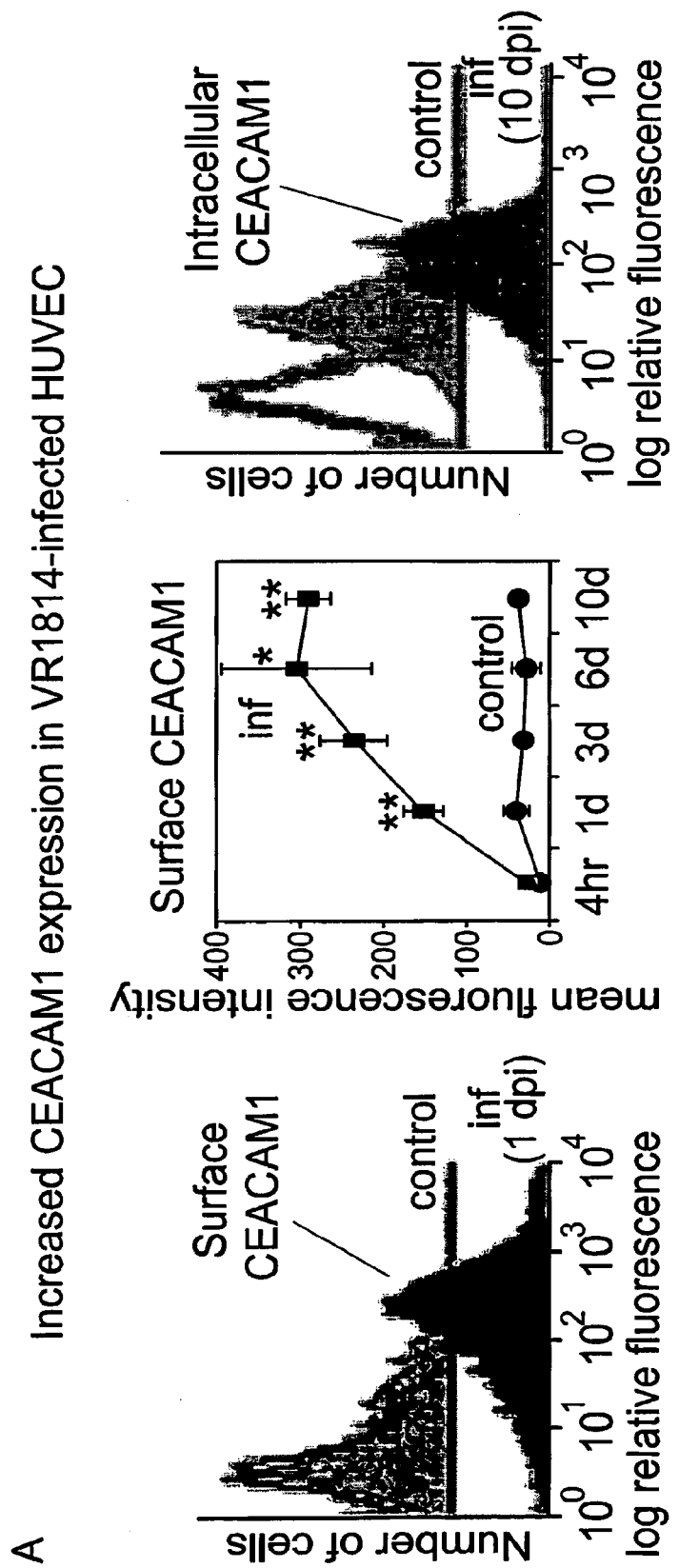
FIG. 6A-D: CEACAM protein increases in CMV-infected HUVEC. (A) (Left panel) Flow cytometric analysis of CEACAM1 surface expression. Typical histograms from control and infected human umbilical vein endothelial cells (HUVEC) are shown. Shaded areas represent expression of specific proteins, and lines represent isotype control. (Middle panel) Graphs represent mean fluorescence intensity (mean±SE). Statistically significant differences are indicated (*$p<0.05$, **$p<0.001$). (Right panel) VR1814-infected HUVEC increase intracellular CEACAM1 protein. Permeabilized cells were analyzed by flow cytometry. Shaded areas represent expression of specific proteins; lines represent isotype control. (B) CEACAM1 levels in conditioned medium measured by ELISA. Polyclonal and biotinylated CEACAM1-specific IgG (R&D Systems) were used for coating and detection, respectively. CEACAM1 was quantified with peroxidase-conjugated streptavidin. CEACAM1 concentration increased in conditioned medium from infected HUVEC (1 PFU/cell). Graphs represent mean value ±SE (n=4). Statistically significant differences are indicated (*$p<0.05$). (C) Infected RUVEC and controls were immunostained for CEACAM1 and CMV gB. Please Note: cells without viral proteins express CEACAM1 (D) Treatment with antioxidants DMSO, DTT (dithiothreitol), and β-mercaptoethanol reduce CEACAM1 expression. Ratios of the mean fluorescence intensity were obtained with control cells.
Figure 6:
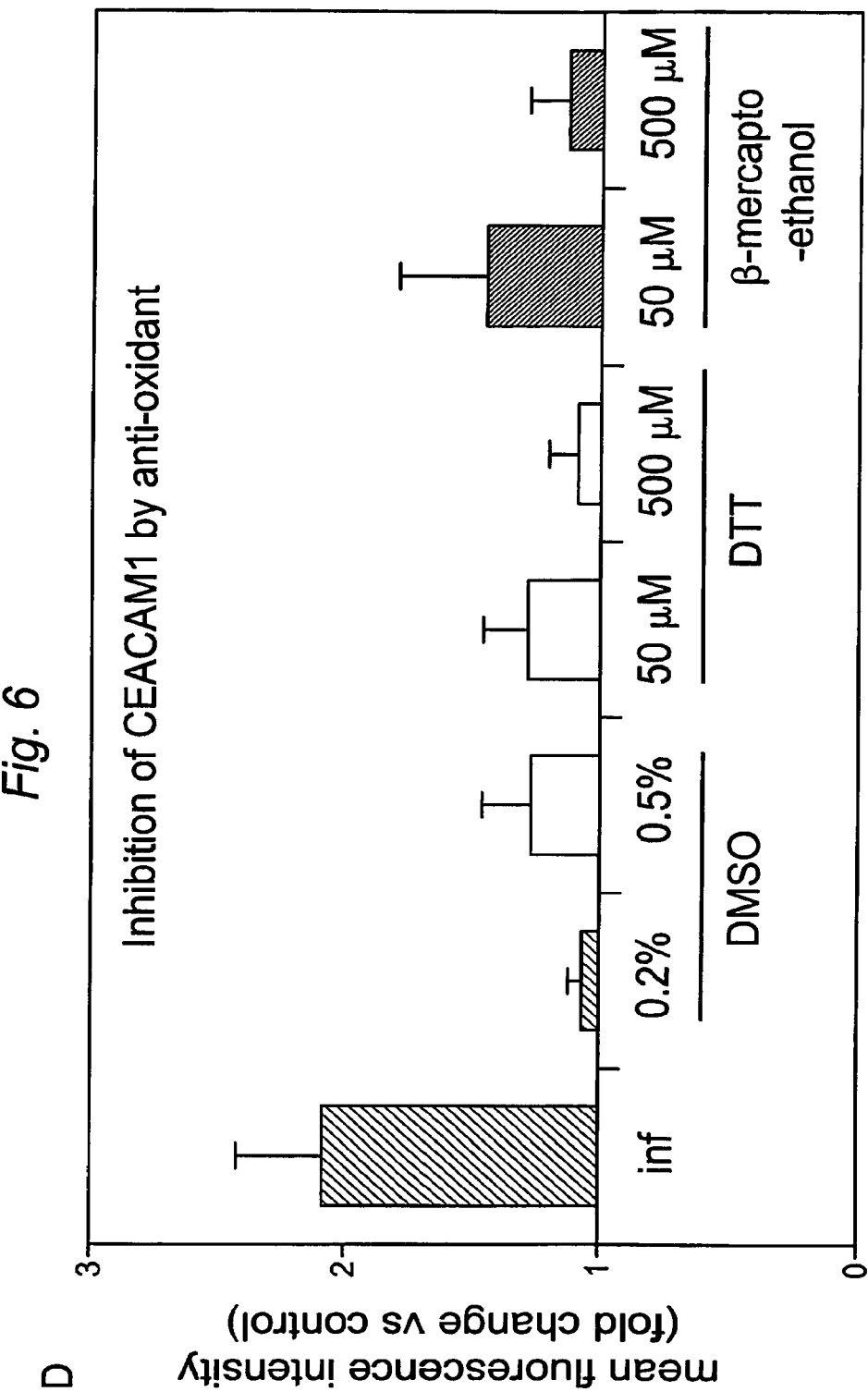

FIG. 4 summarizes sFlt1 levels and median values for each group in a graph. The finding that amniotic fluids from pregnancies with untreated congenital CMV infection contain high sFlt1 levels, reduced after HIG prevention, suggested suppressed viral replication in the placental vasculature and reduced sFlt1. Our results describe a molecular mechanism for CMV-induced inhibition of hypoxic responses in the untreated group (high sFlt1) and villus development, an adaptive response, after HIG treatment (low sFlt1). The results agree with strong VEGF expression in placental biopsy specimens after primary maternal infection and transmission to compensate for sFlt1 binding and inactivation (FIG. 3).

Statistical comparison between controls and untreated individuals showed the following: First, the hypothesis that the median sFlt1 value in the untreated group was greater than 10,000 (the assumed median value among controls as published by Park et al., 2005) was tested. Because there is only one control individual in our study, an exact one-sample Wilcoxon test was applied and yielded a p-value of 0.0006. In addition, with 95% confidence, the median in the untreated group would be above 24,595.

We also performed an exact, two-sample Wilcoxon test of the hypothesis that the median sFlt1 level in the prevention group was lower than that in the untreated group. This test yielded a p-value of 0.032. The 95% confidence interval for the difference of medians between the groups was 2,940-78,599.

Our results indicate elevated sFlt1 in amniotic fluid could serve as an early biomarker for fetuses at risk for disease and improve diagnosis of congenital CMV infection, perhaps more sensitive and reliable than detection of viral DNA by PCR (Table 1). Importantly, we anticipate that reduced sFlt1 levels could be used to measure efficacy of HIG treatment in pregnancies at high risk for congenital CMV disease.

TABLE 1

Quantification of sFlt-1, cmvIL-10 and detection of CMV DNA in amniotic fluid from fetuses diagnosed with prenatal congenital infection.

| Code | sFLT-1 (pg/ml)** | DNA | cmvIL-10 (pg/ml)* | Group |
|------|------------------|-----|-------------------|-------|
| A    | 3,091            | −   |                   | Healthy control |
|      |                  |     | Untreated         |       |
| B    | 43,701           | +   |                   |       |
| C    | 89,985           | −   | 600               |       |
| D    | 86,251           | +   |                   |       |
| E    | 10,103           | +   |                   |       |
| F    | 17,407           | −   |                   |       |
| G    | 34,637           | +   |                   |       |
| H    | 19,834           | −   |                   |       |
|      |                  |     | Before HIG Therapy |      |
| I    | 79,884           | +   | 313               |       |
| J    | 18,397           | +   | 146               |       |
| K    | 6,789            | +   |                   |       |
| L    | 4,058            | +   |                   |       |
| M    | 60,207           | −   |                   |       |
| N    | 45,132           | +   | 0                 |       |
| O    | 48,399           | +   | 0                 |       |

TABLE 1-continued

Quantification of sFlt-1, cmvIL-10 and detection of CMV DNA in amniotic fluid from fetuses diagnosed with prenatal congenital infection.

| Code | sFLT-1 (pg/ml)** | DNA | cmvIL-10 (pg/ml)* | Group |
|------|------------------|-----|-------------------|-------|
| After HIG Prevention | | | | |
| P | 1,118 | – | | |
| R | 6,765 | – | | |
| S | 11,386 | – | 0 | |

**R&D sFlt1 quantification assay
*cmvIL-10 detection limit <100 pg/ml (Tabata)

Example 3

CMV Interleukin 10 (cmvIL-10) Detected in Amniotic Fluids with sFlt1 Levels Our previous studies showed that CMV-infected HUVEC and cytotrophoblasts upregulate CMV IL-10 that impairs cell migration/invasion (Yamamoto-Tabata et al. (2004) *J. Virol.* 78:2831-2840). cmvIL-10 secreted from HUVEC could impair cellular responses at different levels.

Figure 7B:
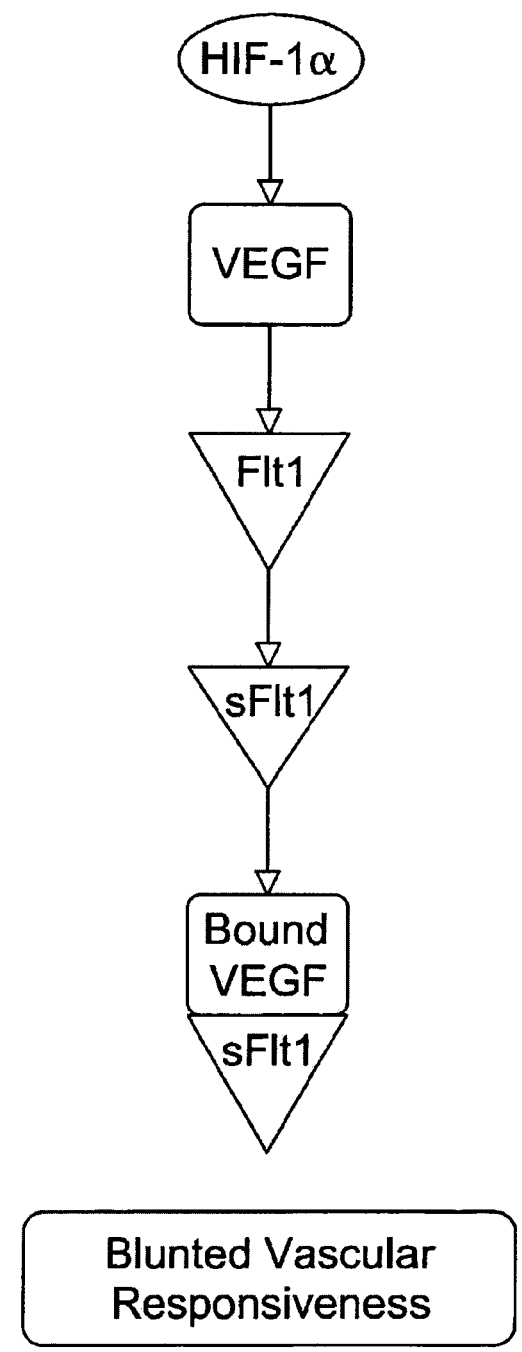
FIG. 7 illustrates the gene expression pathways affected by CMV in vitro and the pregnancy complications predicted to result from congenital infection. (A) Fibrinoid formation is predicted to result from congenital CMV infection. (B) Blunted Vascular Responsiveness is predicted to result from congenital CMV infection. (C) Reduced cell migration/invasion is predicted to result from congenital CMV infection.
Figure 7C:
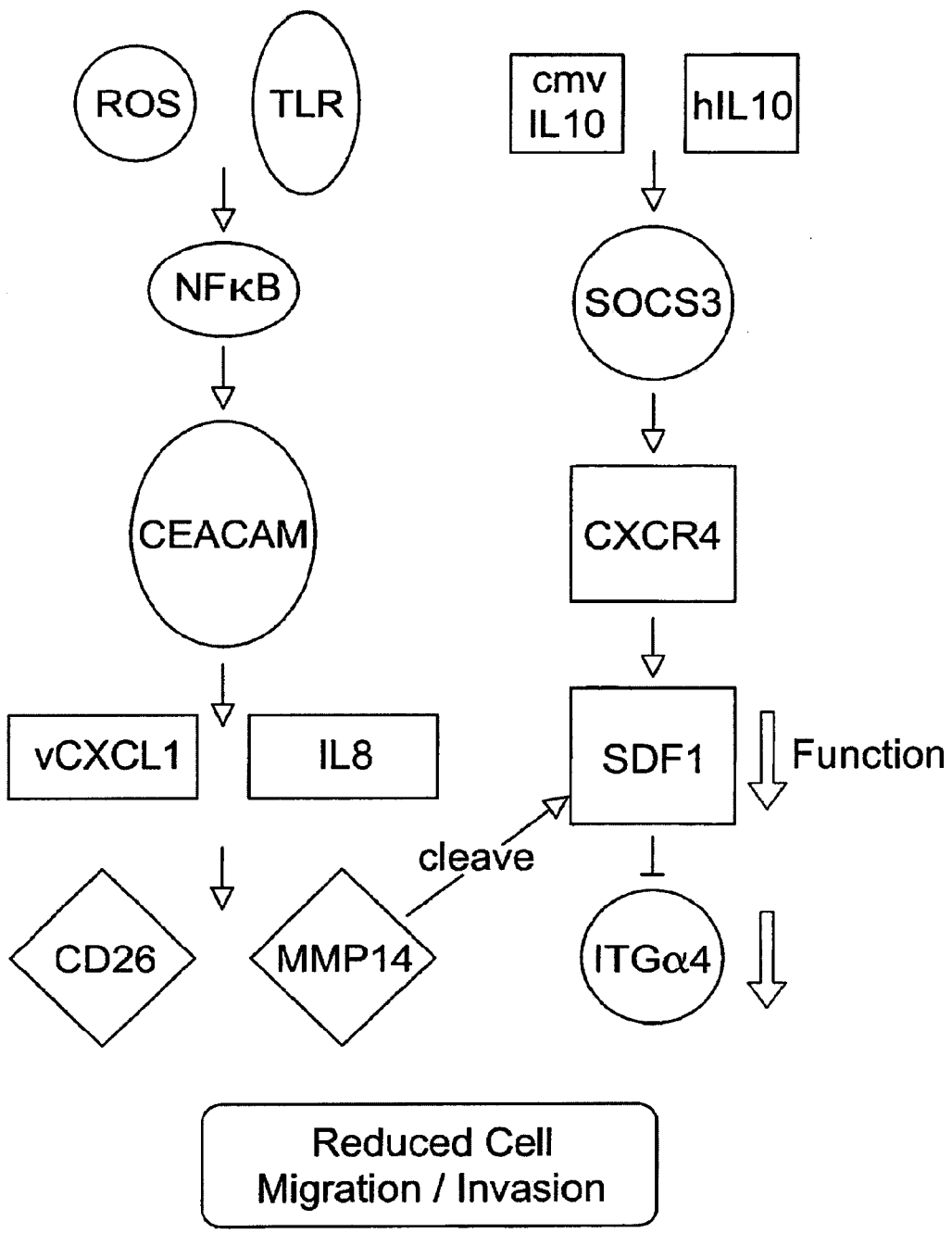

We continued to identify altered cellular proteins caused in CMV-infected HUVEC including SOCS3, metalloproteinases and others. FIG. 7 illustrates the gene expression pathways affected by CMV in vitro and the pregnancy complications predicted to result from congenital infection. These include responses to hypoxia and inflammation—HIF-1α, VEGF, TGF-β, reactive oxygen species (ROS), Toll-like receptors (TLR)—and immunosuppressive factors that mediate SOCS3 suppression of cytokine signaling. With regard to inflammation, NF-κB induces CEACAM1 expression and increases IL-8. vCXC-1 functions similarly to IL-8, inducing MT1-MMP. CMV-induced cytokines could alter the signaling cascade at critical points in CTB differentiation and impair downstream effectors. Pivotal to dysregulation, MT1-MMP alters cytokines in other pathways, e.g., by reducing TGF-β interactions with endoglin and/or SDF-1 binding to CXCR4, decreasing integrins α4 and α9 that mediate cell-cell adhesion in differentiating CTBs.

Example 4

Quantification of Soluble Flt1, Bound VEGF and PlGF in Maternal Sera from Pregnancies Complicated by Congenital CMV Infection Levels of angiogenic factors and antagonists were measured in sera from women with primary CMV infection in the untreated, therapy and prevention groups at seroconversion (SC) and late gestation (LG). Duplicate samples were tested twice by sandwich ELISA for sFlt1 and PlGF (R&D System) and by ELISA for bound VEGF (bVEGF, Chemicon International).

Figure 8:
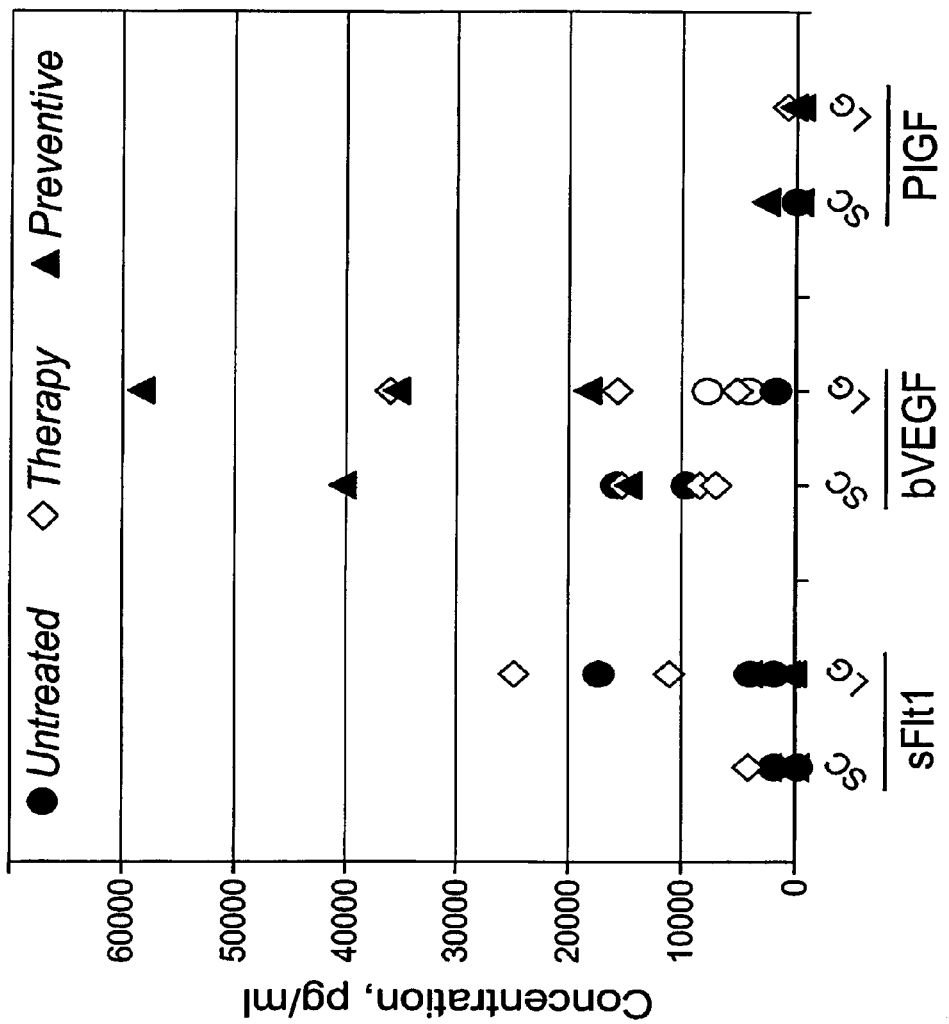
FIG. 8 shows quantification of sFlt-1, bound VEGF and PlGF in maternal sera from pregnancies complicated by congenital CMV infection. Levels of angiogenic factors and antagonists were measured in sera from women with primary CMV infection in the untreated (blue circle), therapy (green square) and prevention (red triangle) groups at seroconversion (SC) and late gestation (LG). Duplicate samples were tested twice by sandwich ELISA for sFlt1 and PlGF (R&D System) and by ELISA for bound VEGF (bVEGF, Chemicon International).

At seroconversion, sFlt1 levels were low in all groups. By late gestation, levels were elevated in some sera from untreated and therapy groups. Most prevention group sera maintained low sFlt1 levels. At seroconversion and late gestation, untreated and therapy groups contained less bound VEGF than prevention group sera. PlGF levels were unchanged (low) at both timepoints for all groups. Approximate levels are shown in FIG. 8 and as follows: healthy control sera sFlt1 941 pg/ml; bound VEGF 6173 pg/ml; PlGF 312 pg/ml.

Our preliminary analysis suggests sFlt1 and bound VEGF levels are elevated in sera from mothers carrying infected fetuses with substantially high levels of dysregulated angiogenic proteins in amniotic fluid (FIG. 1). Together with our observation that villus development continues after HIG treatment (E. Maidji and L. Pereira, unpublished), the results suggest free VEGF protein, after CMV replication was suppressed and SFlt-1 reduced, could enable placental adaptation to intrauterine hypoxia caused by early damage to chorionic villi and placental vasculature. Since small quantities of amniotic fluid reach the maternal blood space in late gestation and hypoxic placentas release anti-angiogenic factors, highly concentrated factors from the fetal compartment could increase levels from maternal circulation.

Recently published case report of placental and fetal hydrops with preeclampsia-like symptoms associated with congenital CMV disease and fetal demise associated with elevated sFlt1 levels in maternal blood. Together with our preliminary analysis of sera (FIG. 8), the results suggest that antiangiogenic proteins in maternal sera from pregnancies complicated by congenital CMV infection could parallel levels of elevated factors in samples of amniotic fluid from the fetal compartment. Accordingly, circulating factors in maternal sera, like those in amniotic fluid, should decrease after HIG treatment suppressed intrauterine CMV replication (Nigro et al, 2007). We continue to evaluate several hundred sera and corresponding amniotic fluid from congenital CMV infection and controls to measure levels of angiogenic factors and inhibitors. Ideally, we hope to determine whether levels of these factors could also be used as biomarkers to predict status of the developing fetus and disease outcome.

Example 5

Congenital CMV-Induced Mirror Syndrome and Preeclampsia Correlate with Increased Anti-Angiogenic Factors CMV-induced Mirror syndrome is a rare pregnancy complication characterized by maternal edema and preeclampsia that "mirrors" fetal and placental hydrops (Rana et al, ACOG, v109, 2007). Rana et al. suggest that placental edema from ischemia mediates production of sFlt1 and endoglin that reach maternal circulation. The fetus died shortly after birth with subcutaneous edema, pleural effusion, erythroblastosis and extensive extramedullary hematopoiesis. The placenta was markedly enlarged for gestational age in agreement with other reports of placentomegaly in congenital CMV infection (La Torre et al., CID, 2006). Elevated circulating sFlt1 returned to normal after delivery and preeclampsia resolved. Several cases of congenital CMV-induced fetal hydrops have been reported, but this is the first to describe Mirror syndrome with preeclampsia and elevated antiangiogenic factors. It was noted that sFlt1 levels in maternal serum with profound congenital infection resemble the most severe form of preeclampsia. Thus, antiangiogenic factors released from the fetal-placental unit increase the risk of this life-threatening pregnancy complication.

Figure 9:
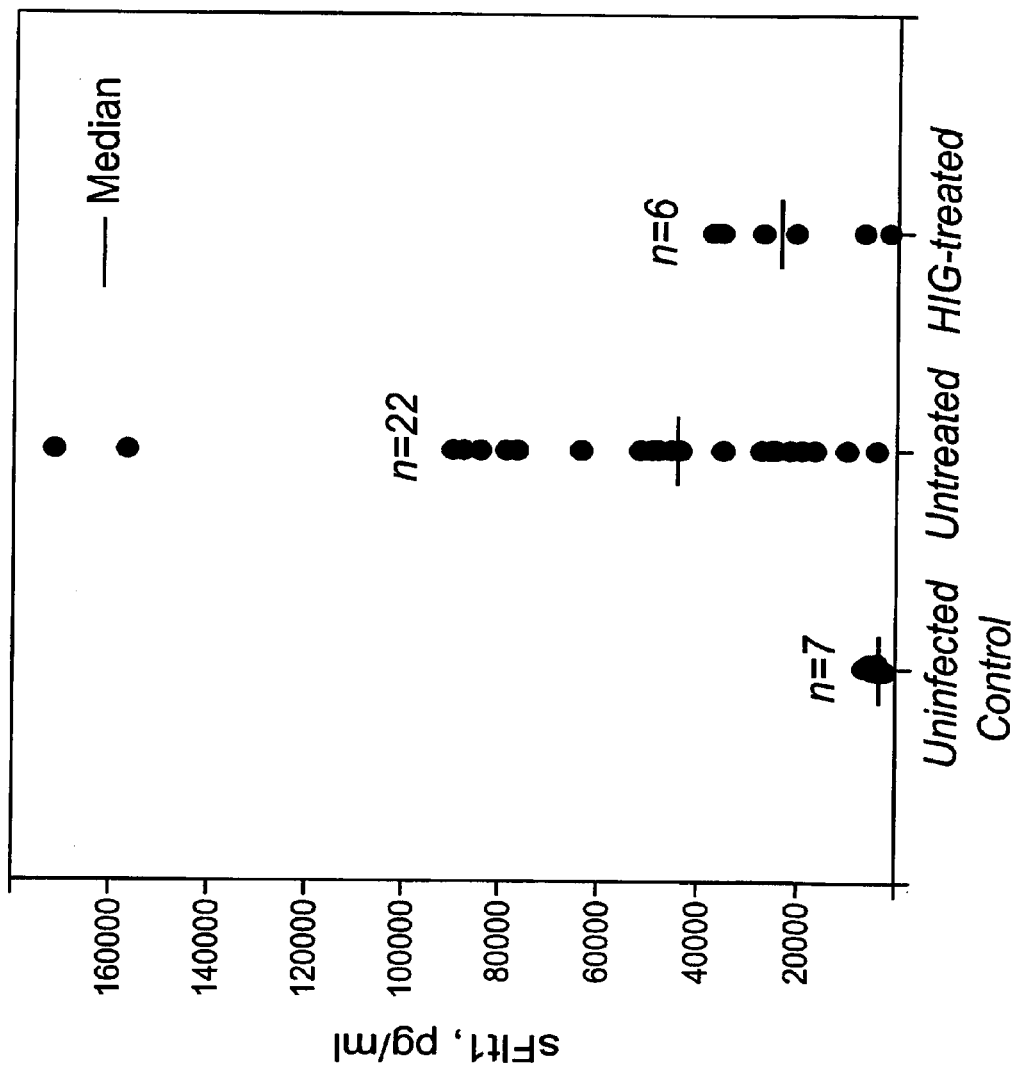
FIG. 9 shows elevated sFlt1 in amniotic fluid (AF) from congenital CMV infection (Untreated), as compared with RIG-treated (Prevention) and uninfected control groups. Measured by ELISA (R&D Systems).

FIG. 9 shows elevated sFlt1 in amniotic fluid (AF) from congenital CMV infection (Untreated), as compared with HIG-treated (Prevention) and uninfected control groups. The importance of elevated sFlt1 for development of edema in the placental-fetal compartment that could predispose to preeclampsia prompted us to compare sFlt1 levels in untreated congenital infection (n=22), HIG prevention (n=6), and seronegative controls (n=7) (Nigro et al, 2005). We confirmed that sFlt1 was highly elevated in untreated infection, as compared with HIG-treated and uninfected controls (FIG. 9).

Figure 10:
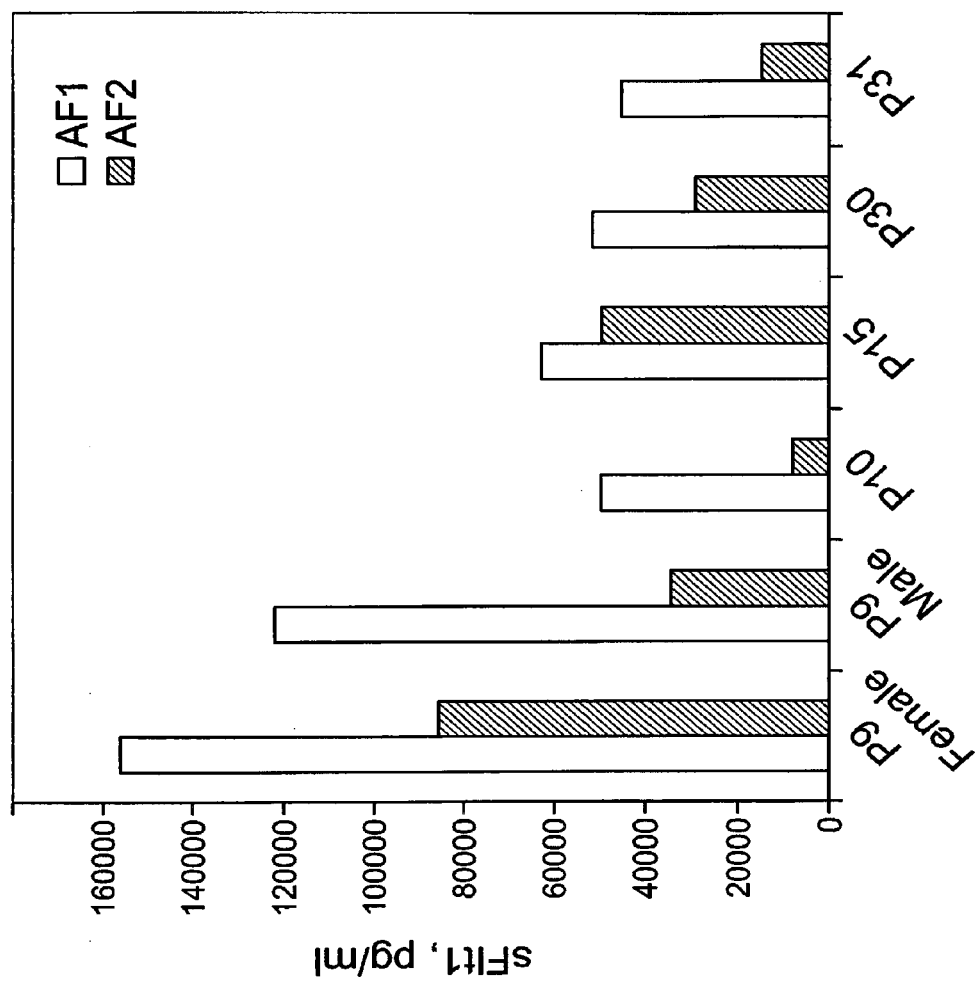
FIG. 10 shows elevated sFlt1 in first amniotic fluid (AF1) from congenital infection was reduced in a subsequent sample (AF2) 6 to 12 weeks after therapy.

To determine whether sFlt1 levels correlate with fetal recovery, we compared concentrations of the factor in the first AF1 (blue) at diagnosis of fetal transmission with the second AF2 (red) after HIG therapy (FIG. 10). Elevated sFlt1 in AF1 of a twin pregnancy P9 was reduced in both fetuses after therapy. Likewise, considerably lower sFlt1 was found in AF from P10 after HIG therapy. sFlt1 levels from P15, P30 and P31 were also reduced after therapy. Although only a small number of AF2 samples were available, the results suggest sFlt1 levels are reduced after HIG therapy. We believe that the many small villi and blood vessels developed during adaptation to placental hypoxia further reduce sFlt1 levels and edema, improve blood circulation, and restore normoxia in the fetus.

Example 6

Placentomegaly and Elevated sFlt1 Correlate in Congenital CMV Infection

CMV-induced Mirror syndrome suggested high sFlt1 could induce endothelial swelling and increase vascular permeability leading to placental-fetal edema and maternal preeclampsia. To determine whether increased size (vertical thickness) of placentas from congenital infection correlates with the increased sFlt1 levels and would decline with HIG treatment as placentomegaly decreased, we compared sFt1 values and placental size from untreated, HIG-therapy, HIG-prevention and uninfected controls using the original data on placental thickness. Our results are as follows. (i) At the time of diagnosis of fetal infection and IUGR, placentas had high sFlt1 levels and placentomegaly (11/11) suggesting an association. (ii) In untreated cases, high sFlt1 levels correlated with enlarged placentas (6/6). (iii) After HIG therapy, sFlt1 levels decreased and placental thickness reduced (3/3). (iv) HIG prevention (early treatment) reduced placental size and sFlt1 levels also declined (3/3). (v) Uninfected controls with low sFlt1 levels had normal size placentas (5/5). Notably, the few instances of leukocytic infiltration, cytomegalic cells and focal infection were only detected in tissues from the untreated group. The results indicate that increased sFlt1 levels in congenital CMV infection correlate with placentomegaly and both are reduced by HIG treatment. Together the results suggest that inflammation and edema subside as new vascularized villi develop that compensate for hypoxia, increasing blood flow to the fetus, and enabling recovery from placental insufficiency in utero.

Example 7

Histomorphological and Quantitative Analysis of Placental Biopsy Specimens

Figure 11:
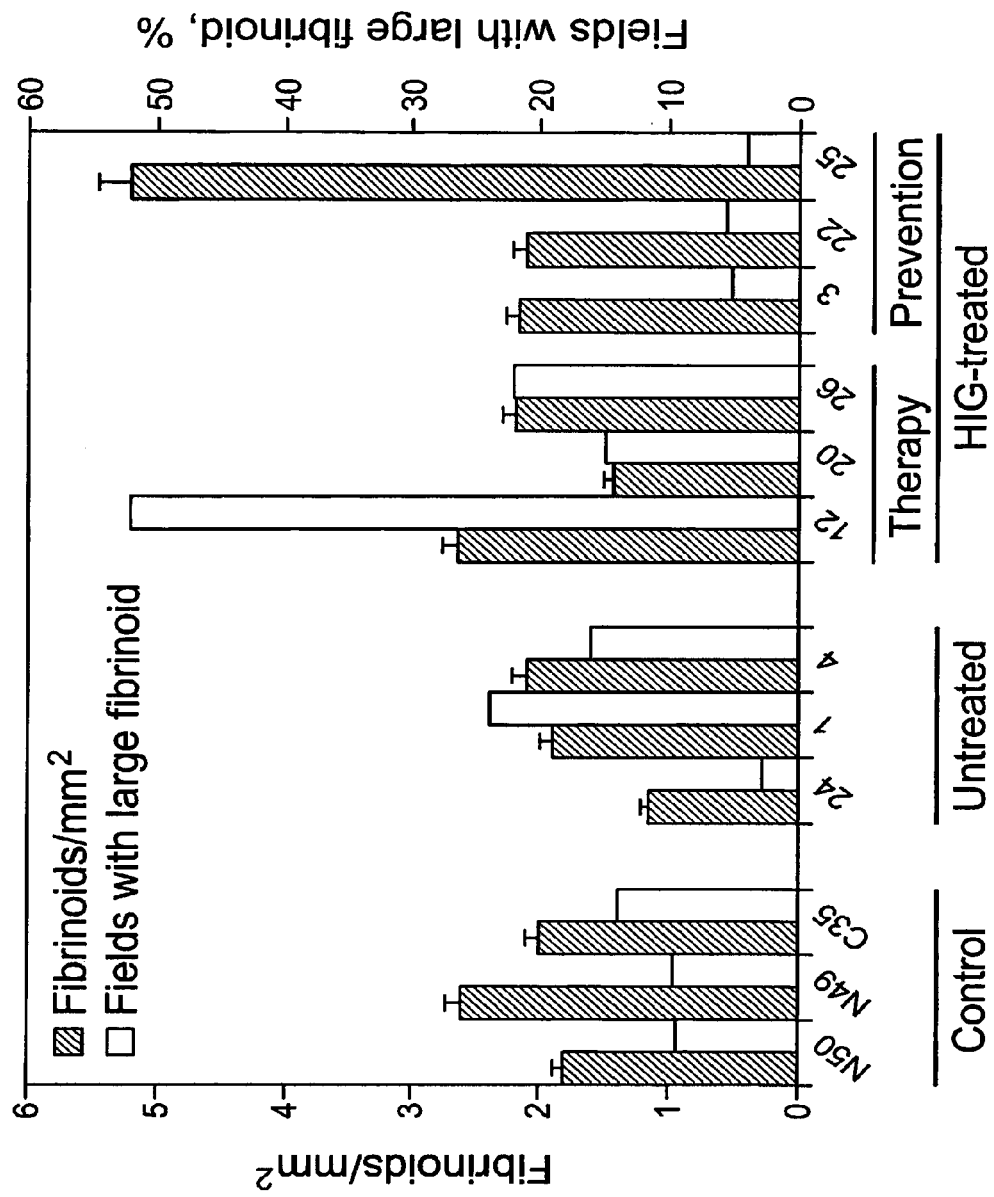
FIG. 11: Presence of large fibrinoids suggests early damage and repair following HIG therapy. Fibrinoids were counted in R&E-stained sections from placentas (100 to 200 fields) in control, untreated, therapy and prevention groups. Results expressed on the double y axis bar graph. Lefty axis represents total number of fibrinoids/mm$^2$ (mean±SEM). Right y axis represents percentage of fields with large fibrinoids.
Figure 12:
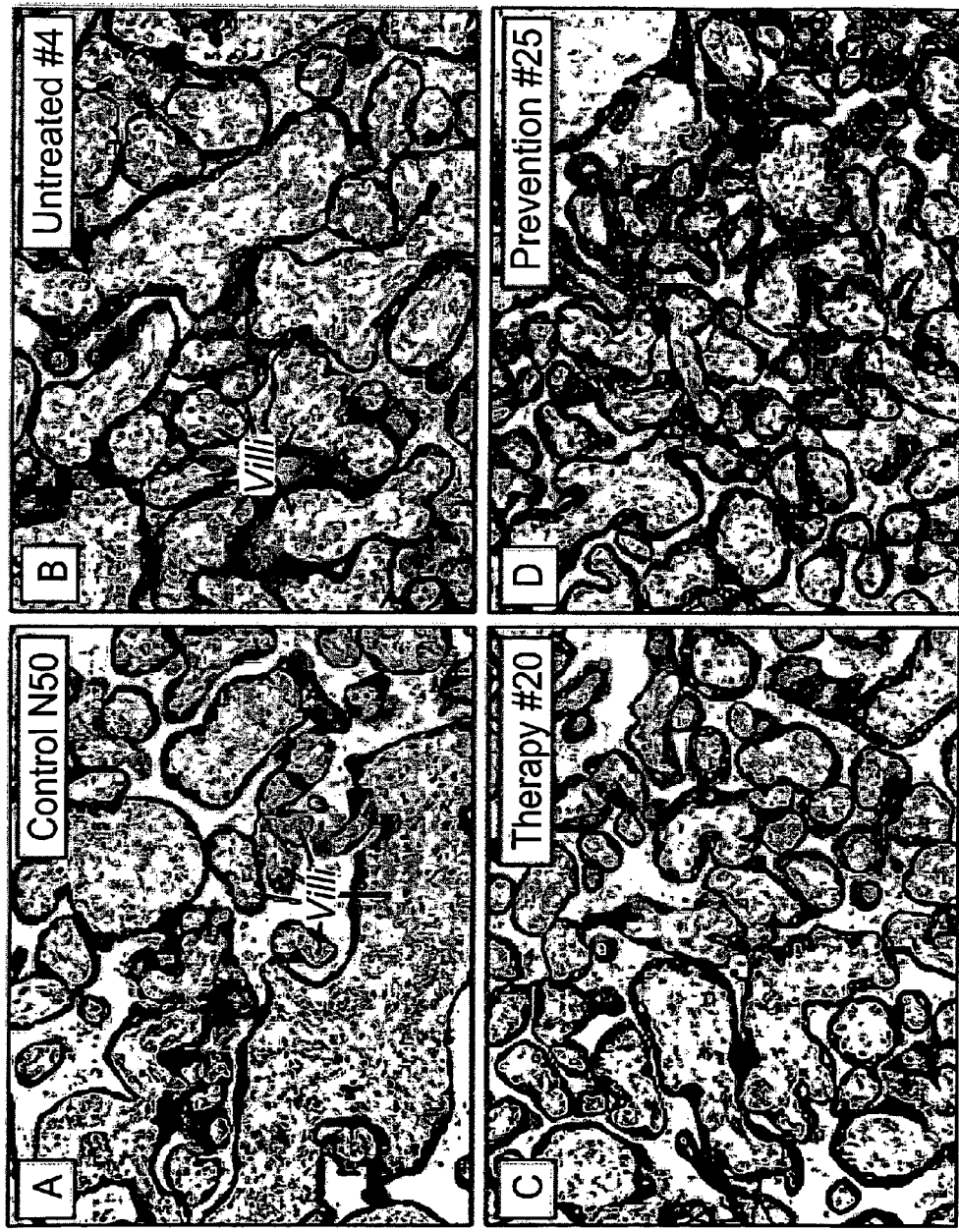
FIG. 12: Increase in number of small chorionic villi after HIG treatment of infected placentas. Cross-sections of chorionic villi immunostained with anti-cytokeratin. The number of villi/mm$^2$ was quantified (100-200 fields) in (A) healthy placentas (control) (B) untreated, (C) therapy, and (D) prevention groups. Center graph (E) shows a comparison of the ratios of average counts relative to controls, using Poisson regression.
Figure 12:
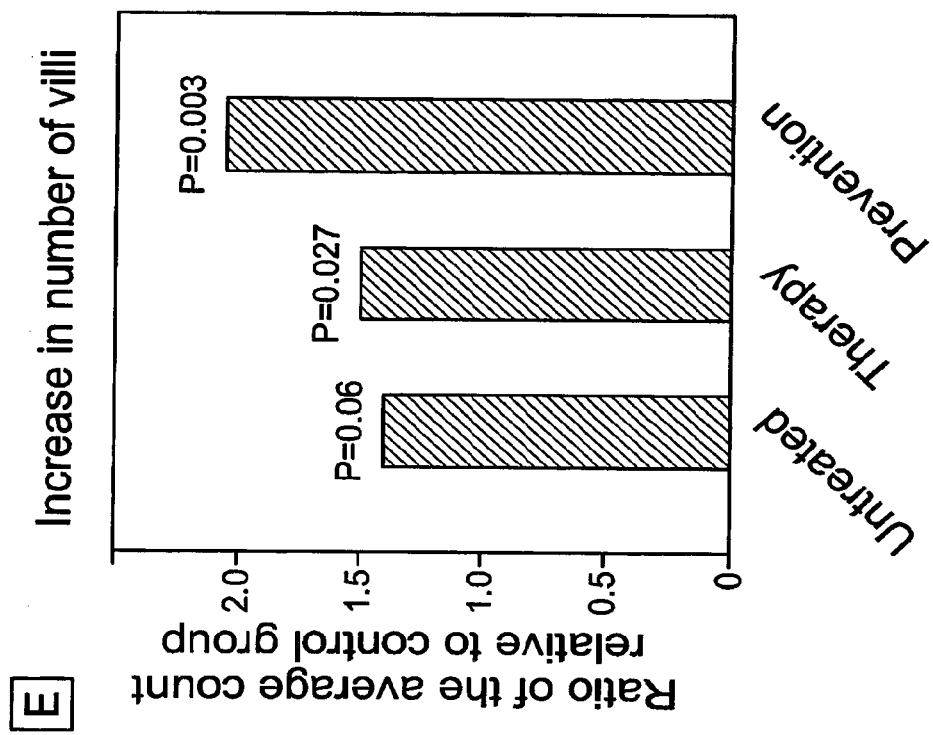
Figure 14A:
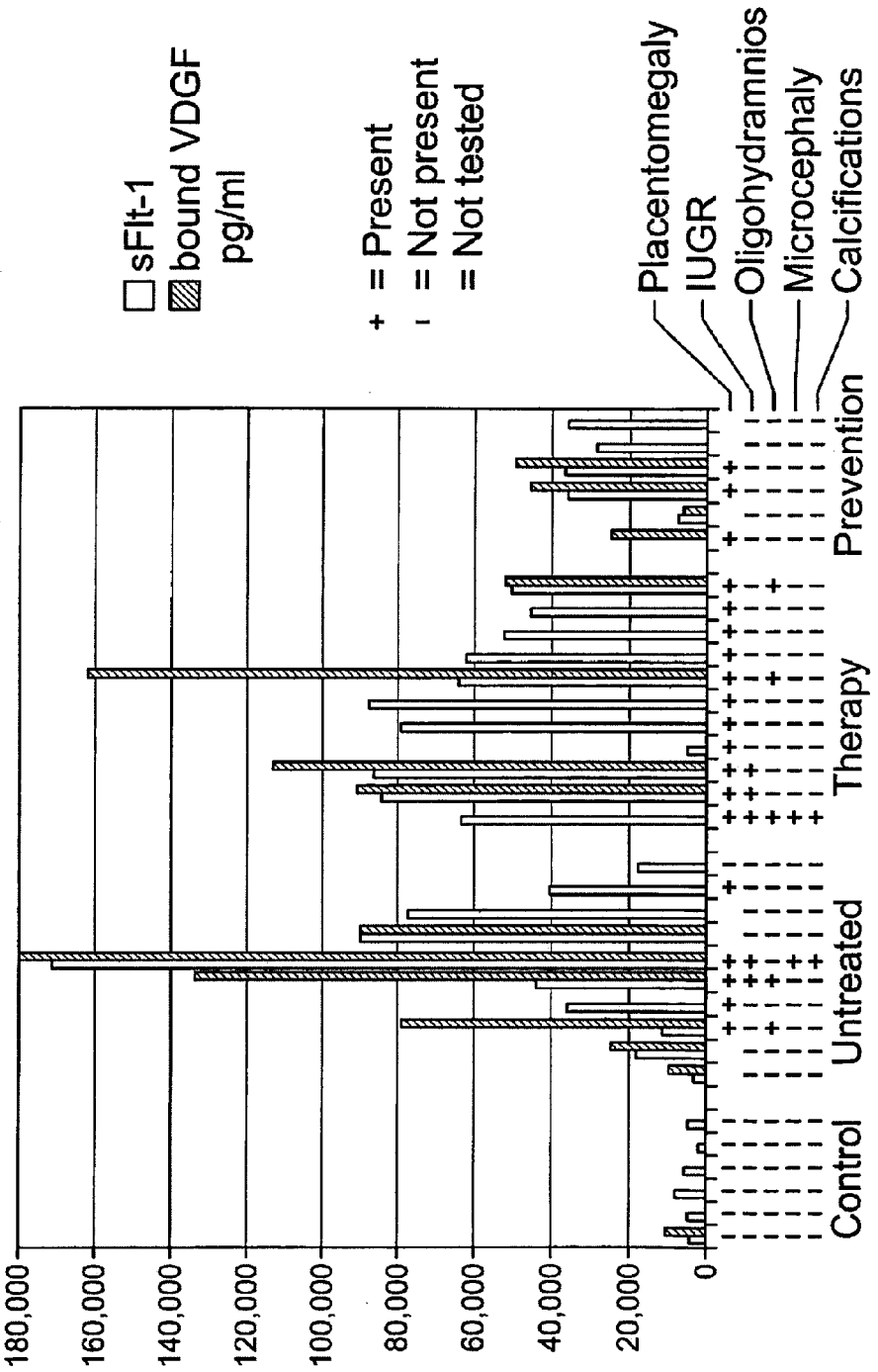
FIG. 14A-B. Levels of biomarker levels in amniotic fluid of congenital. CMV infection correlate with placental dysfunction, fetal anomalies and patterns of symptomatic disease. Placental enlargement (placentomegaly) and oligohydramnios, fetal anomalies (IUGR resolves after birth), fetal infection (CMV genome equivalents/ml), microcephaly and brain calcification (permanent birth defects) found by ultrasound at midgestation. Panel A: Quantification of biomarkers in seronegative controls, untreated and therapy groups (before HIG treatment) (1, 2). Panel B. Biomarker levels in prevention group after early hyperimmune globulin treatment. Left: soluble VEGFR1 (sFlt-1) and bound VEGF (bVEGF) (pg/ml). Right: cmvIL-10 pg/ml in amniotic fluid (panel A only).
Figure 14B:
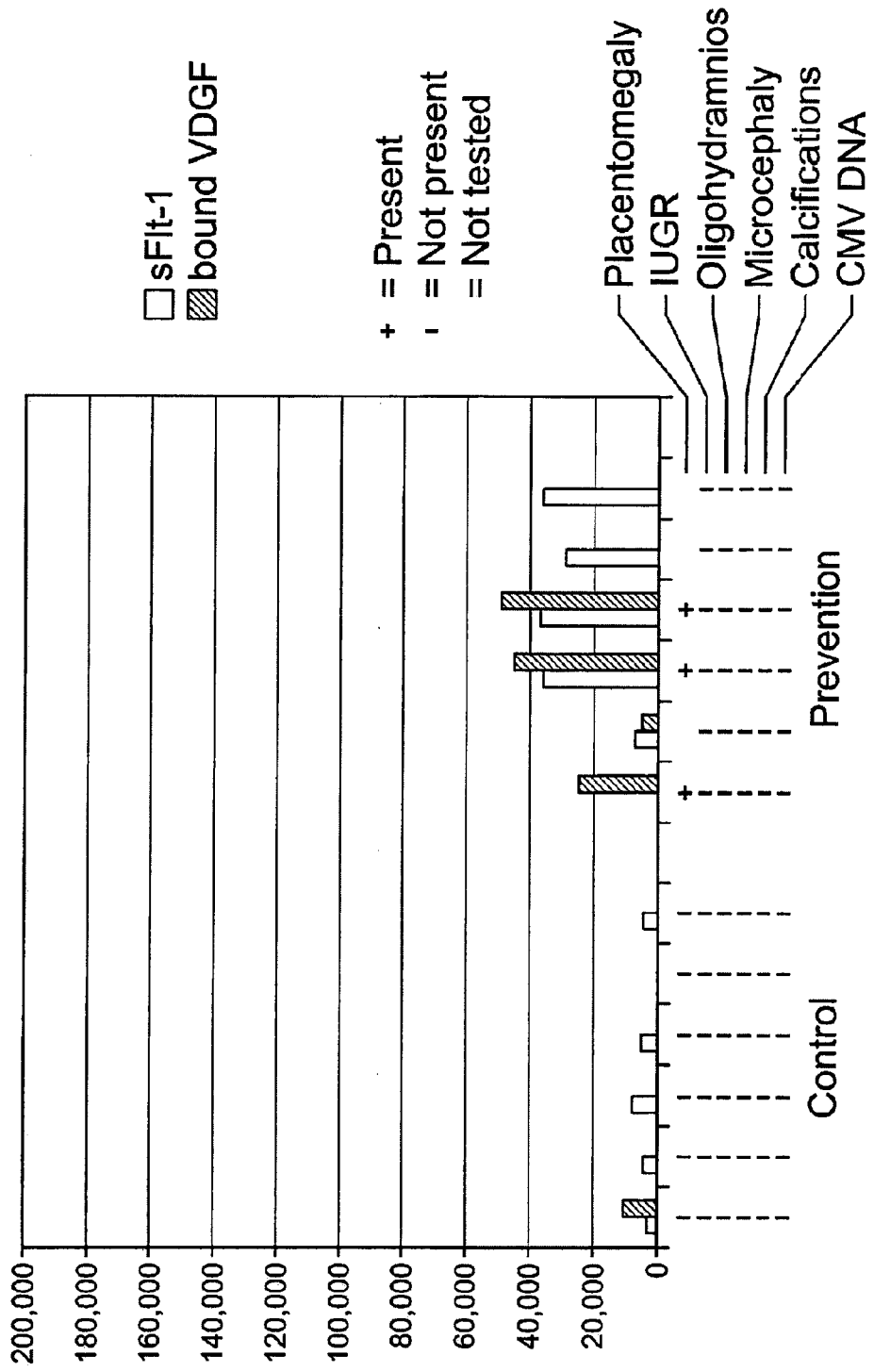

Our studies indicate that placental infection and damage can result in insufficient functions, accounting for early signs of congenital infection observed by ultrasound. FIGS. 11, 12, and 3 summarize results from histomorphological and quantitative analysis of placental biopsy specimens at delivery from controls, untreated, therapy and prevention groups (Nigro, 2005). Information on fetal-neonatal outcome and placentomegaly (La Torre, 2006) from patient histories is also included (Table 2). CMV-infected cytotrophoblasts are impaired in differentiation and invasion comparable to the pregnancy complication preeclampsia (PE) (Lim et al., 1997) (Fisher et al., 2000) (Yamamoto-Tabata et al., 2004). In placentas and maternal sera from severe PE, expression of growth factor ligands and receptors is altered (Zhou et al., 2002) (Maynard et al., 2003) (Levine et al., 2004) (Venkatesha et al., 2006). Our in vitro studies showed that CMV-infected endothelial cells secrete appreciable amounts of soluble Flt-1 (sFlt-1), an angiogenesis antagonist, and a non-functional form of vascular endothelial growth factor, bound VEGF, quantified by ELISA (FIG. 14). In addition, immunostained placentas from congenital infection indicated growth factors and receptors were upregulated. To quantify dysregulated factors, levels of sFlt-1, free and bound VEGF, placental growth factor (PlGF) and soluble endoglin-1 (sEng) were measured in 33 amniotic fluid (AF) and 14 maternal serum samples at 20 weeks gestation. To assess viral replication, we measured an immunosuppressive viral cytokine, cmvIL-10, produced late in infection (Kotenko et al., 2000) (Spencer et al., 2002) (Yamamoto-Tabata et al., 2004). FIG. 14 summarizes the key biomarkers of congenital CMV infection with placental dysfunction and adverse fetal outcome.

Figure 13:
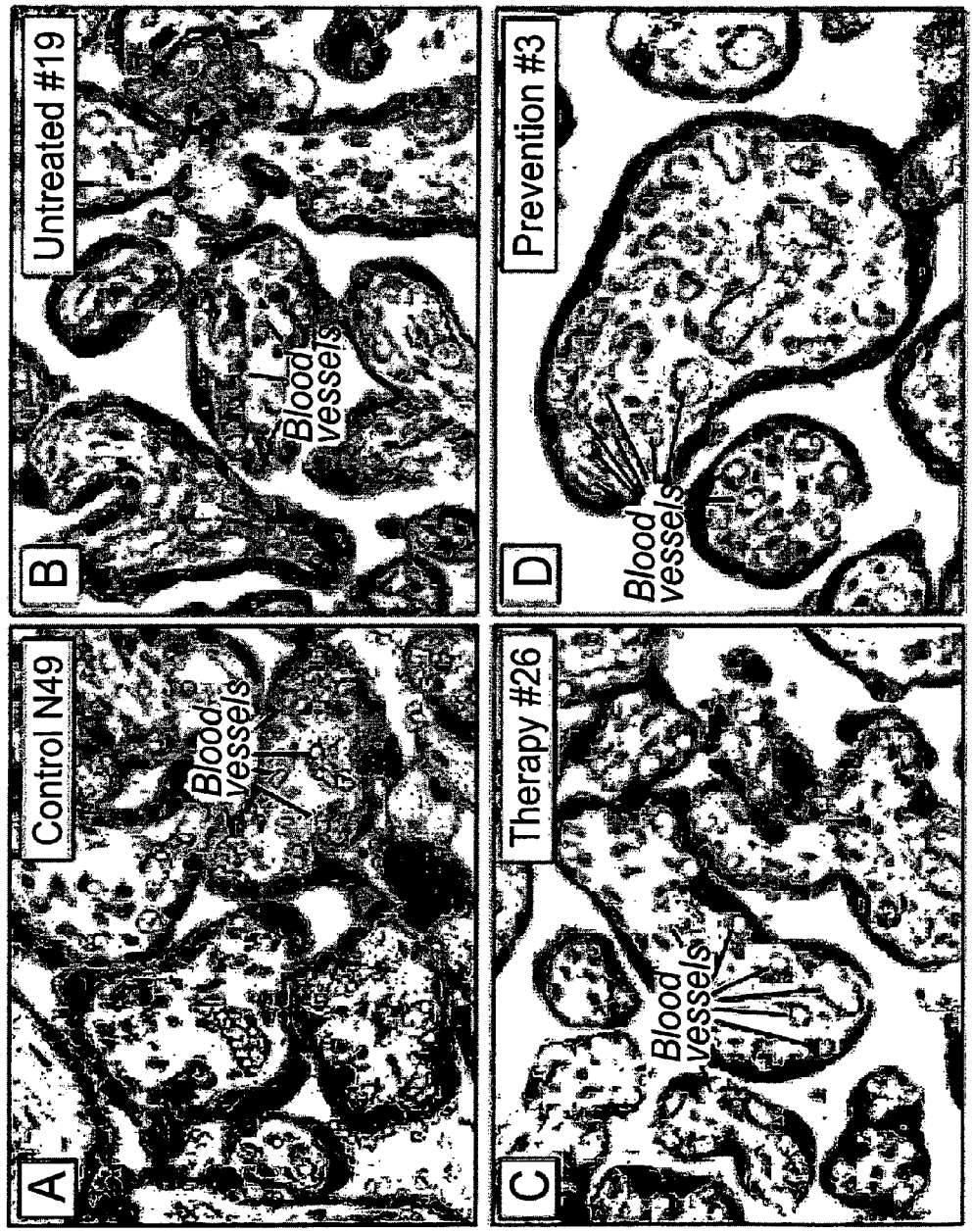
FIG. 13: Increased villi and fetal blood vessels in HIG-treated placentas. Tissue biopsy samples from placentas from control (A) (healthy), (B) untreated, (C) therapy and (D) prevention groups were formalin fixed, paraffin embedded, sectioned, and double immunostained for vWF and CTB marker cytokeratin. Nuclei were counterstained with hematoxylin. Number of villi per mm$^2$ (brown) and blood vessels per villus (pink) were counted. The relationship between blood vessels and villus numbers is shown on the (E) double y axis bar graph. Data are presented as mean±SEM.
Figure 13:
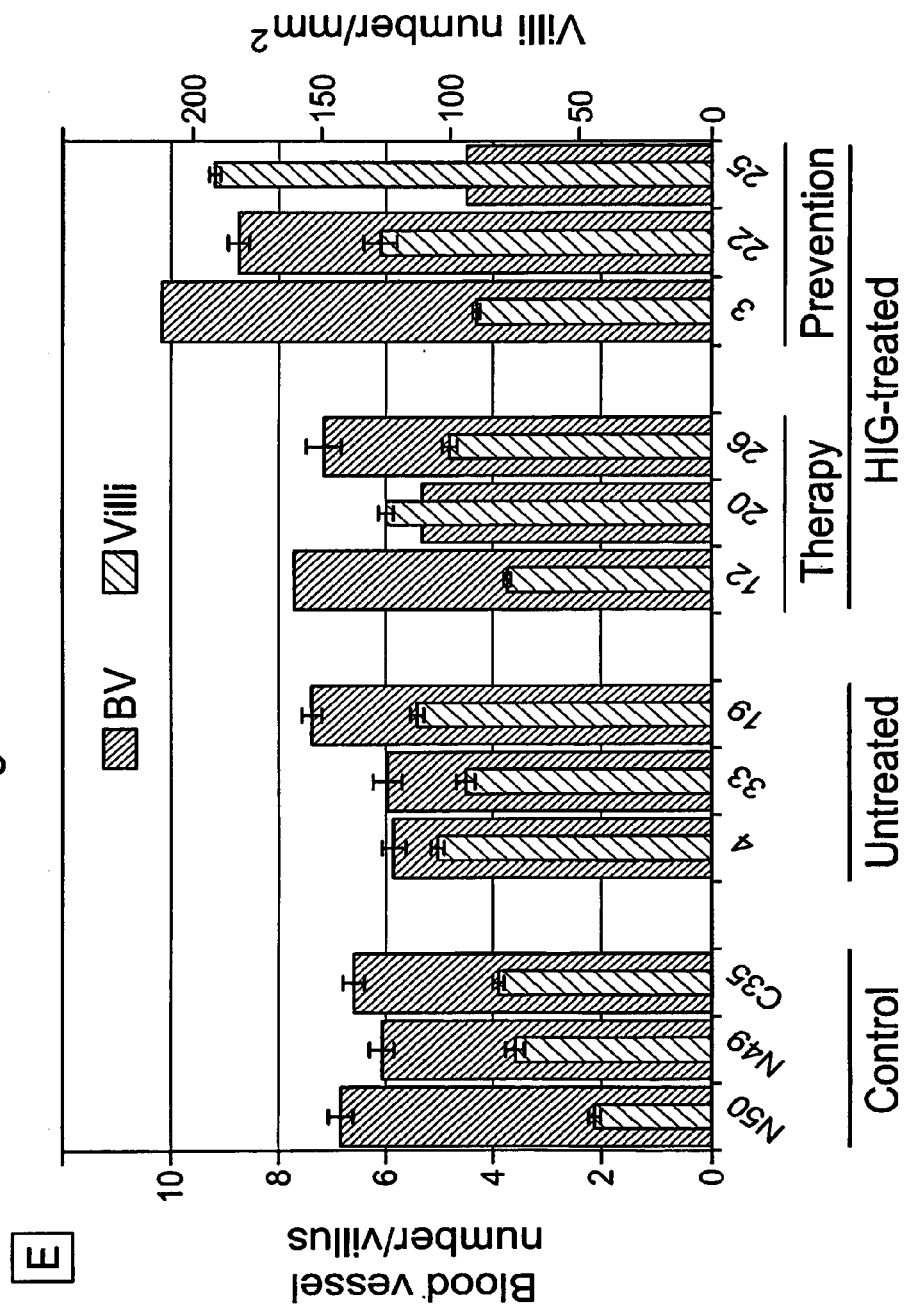

Adverse fetal-neonatal outcome predicted by placental damage and dysregulated growth. Morphological features of placentas that predicted an adverse outcome included extensive areas with large fibrinoids, villous necrosis, calcification and high levels of syncytial knotting (FIGS. 11-13). In untreated placentas, the number of villi was slightly higher than that in uninfected normoxic controls, suggesting that there was some increase in surface area as adaptation for hypoxia. Placentomegaly, enlarged vertical thickness from fibrosis, edema and inflammation, developed in all infected placentas and increased in untreated symptomatic fetuses.

Biochemical markers included intense immunostaining for VEGF and its receptor Flt-1, which are strongly upregulated in hypoxic tissues. Quantification of these proteins (i.e., biomarkers) in AF and sera showed that sFlt-1 and bound VEGF were dramatically increased in symptomatic disease (FIG. 14). In contrast, PlGF was reduced and free VEGF was undetectable (data not shown). In general, sEng levels in AF were low. After HIG therapy and prevention, placentomegaly decreased in direct relation to reduced levels of antiangiogenic proteins. Very high viral loads in AF quantified by PCR as genome equivalents ($>10^5$ CMV genomes/ml), which predict symptomatic disease (Lazzarotto, 1999) (Guerra, 2000), were present in some untreated placentas and before HIG therapy.

The immunological feature central to placental and fetal infection was persistent, low-avidity maternal antibody (i.e., recent maternal seroconversion). A chemokine, SDF-1, downregulated by hypoxia and in PE (S. Fisher, in preparation), was absent in congenital infection. In contrast, the receptor CXCR4 was expressed. We determined that the viral cytokine, cmvIL-10, increased in AF and was directly related to ongoing infection in the placental-fetal unit, as indicated by viral load.

Favorable fetal-neonatal outcome predicted by placental development that compensated for hypoxia and restored function. Morphological features of placentas that predicted a favorable outcome included moderate to low injury (i.e. small fibrinoids and moderate syncytial knotting). Placentomegaly was uniformly reduced in some untreated asymptomatic fetuses and in all placentas receiving HIG treatment, but did not reach normal controls (La Torre, 2006). In a remarkable example of adaptive plasticity, the number of chorionic villi increased dramatically after therapy, and more so after prevention, as compared with most untreated placentas (FIG. 13). With earlier treatment (prevention), there was an appreciable increase in fetal capillaries indirectly related to villous number (i.e., more blood vessels formed in fewer villi). In any case, both treatment protocols increased the total number of blood vessels as compared with that in untreated infected placentas and normoxic controls.

Biochemical markers of favorable outcome included moderate immunostaining for VEGF and its receptor Flt-1, indicating continued hypoxia. Quantification of these biomarkers in AF and in sera showed that sFlt-1 and bound VEGF values were higher in uninfected and asymptomatic infected fetuses, with or without HIG treatment, as compared with uninfected control placentas (FIG. 14). Levels of sEng appeared somewhat higher after HIG treatment. AF contained few or no CMV genome copies.

Immunological markers included continued development of moderate-to-high-avidity CMV antibodies. SDF-1 was absent and its receptor CXCR4 was expressed. With one exception, cmvIL-10 was not detected in AF from uninfected fetuses.

These results suggest that congenital infection occurs in three stages: (1) infection in the uterus and placenta, (2) transplacental spread with asymptomatic infection, and (3) virus replication in fetal organs and symptomatic congenital disease. The extent of infection can be quantified at midgestation by the levels of dysregulated growth factors produced by the hypoxic placenta, the infected fetus, and increasingly in the symptomatic diseased fetus. In accord with placentomegaly, frequent indicators of placental dysfunction that resolved after birth included intrauterine growth restriction and oligohydramnios (i.e., reduced amniotic fluid composed of fetal urine). The latter could result from hypoxemia-induced redistribution of fetal cardiac output that shunts blood away from kidneys to vital organs, decreasing renal perfusion. Symptomatic diseased neonates had brain disease, microcephaly and calcification.

Placentas from the untreated, therapy and prevention groups showed morphological evidence of early viral damage, overall injury from long-term hypoxia (FIG. 11) and compensation by increasing formation of vascularized villi (FIGS. 12 and 13). Notably, concentrations of the key biomarkers of unfavorable outcome—sFlt-1 and bound VEGF— were extremely high in both untreated and therapy groups (before treatment) (FIG. 14). The only difference between these groups was HIG administration that improved fetal outcome. It was recently reported that untreated congenital CMV infection can cause mirror syndrome, which is fetal hydrops in maternal PE with an extremely high sFlt-1 level in maternal blood (Rana, 2007). Hydrops, a manifestation of fetal cardiac failure, is associated with villous edema. Compression of villous blood vessels by edema and encased fibrotic villi can reduce intervillous space and bloodflow thereby reducing the fetal oxygen supply. Our results suggest that congenital infection could contribute to PE by inducing anti-angiogenic conditions in the placental-fetal unit that range from mild to severe and can be diagnosed early by measuring anti-angiogenic factors in the maternal and fetal compartment.

The pivotal feature of placental compensation that predicted a favorable outcome was the presence of small vascularized villi in response to a hypoxic environment. Villi and blood vessels developed on a continuum: low numbers in untreated placentas, moderate after therapy, and high with early prevention. De novo formation of chorionic villi could improve placental perfusion and supply the increasing demands of the developing fetus as gestation progresses. Increased surface area for exchange of substances with maternal blood could explain an improved fetal outcome independent of treatment. Nonetheless, transport of high-avidity IgG from maternal circulation, generated naturally or by HIG administration, could suppress viral replication in both placenta and fetus, accounting for the many asymptomatic and uninfected neonates after treatment.

TABLE 2

| Group | Placenta/ No. | Outcome§ Placenta/ Fetus-Neonate | sFlt-1 AF* | sFlt-1 sera | bVEGF AF* | bVEGF sera PLGF[a] AF | (sEng)[b] pg/ml | Placmeg# (sFlt-1) | Placenta Pathology/ Compensation¥ |
|---|---|---|---|---|---|---|---|---|---|
| Control | P-21 | Seronegative | 3,091** | 941** | 9,727** | 281[a] | (81)[b] | Normal | 35-40 villi/mm²; 6 BV |
|  | GN495 | Seronegative | 3,915** |  |  |  |  | Normal | — |
|  | GN502 | Seronegative | 7,136** |  |  |  |  | Normal | — |
|  | GN516 | Seronegative | 4,934** |  |  |  |  | Normal | — |
|  | GN522 | Seronegative | 1,067** |  |  |  |  | Normal | — |
|  | GN528 | Seronegative | 3,798** |  |  |  |  | Normal | — |
|  | P-7 | Neonate Uninfected | 2,494** |  | 8,477** |  |  | ND |  |
|  | P-6 | Neonate Uninfected Placentomeg/Symp: TOP | 17,407†† |  | 23,219†† |  |  |  |  |
|  | P-2 | Oligohydramnios, brain inclusions, intravent hemo | 10,103†† |  | 78,396*** | 166[a] |  |  | 12,460 CMV ge/ml AF |
|  | P-27 | Neonate Uninfected |  | 4,009*** |  |  |  | Increased | Minimal fibrosis |
|  | GN536 | Neonate Uninfected | 35,055†† |  |  |  |  | Increased | — |
|  | P-23 | Placentomeg/Symp: IUGR, Oligohydr, esoph atresia | 43,701†† | 3,557*** | 133,025*** |  |  | Increased | 302,340 CMV ge/ml AF |
|  | P-1 | Placentomeg/Symp: IUGR, microcephaly, calcifications, thrombocytopen, purpura | 171,350*** |  | 179,949*** | 150[a] |  | Increased | Minimal fibrosis/ Minimal compensation |
| Un-Treated | P-4 | Symptomatic/oligohydramnios IUGR, cardiomeg, splenomeg, paralysis, mental retardation |  |  |  |  |  | ND | 219,710 CMV ge/ml AF |
|  | P-25 | Neonate Uninfected | 89,985*** | 4,075*** | 89,212*** | 58[a] | (524)[b] | ND | Moderate damage/ 50 villi/mm² §AF: 604 pg/ml cmvIL-10 |

TABLE 2-continued

| Group | Plac/ No. | Outcome§ Placenta/ Fetus-Neonate | sFlt-1 AF* pg/ml | sFlt-1 serum pg/ml | bVEGF AF | bVEGF s PLGF$^a$ | Placemeg# (sFlt-1) (sEng) | Placental Pathology†/ Compensation |
|---|---|---|---|---|---|---|---|---|
| | P-5 | Placentomeg/Symp: IUGR, thrombocytopenia | ND | ND | | | ND | High fibrosis & knotting, necrosis, calcification/ 30.8 villi/mm$^2$; 4.8 BV |
| | P-24 | Asymptomatic infected | | 2,676†† | | 15,232 | Increased | — |
| | GN656 | Asymptomatic infected | 77,078*** | | | | (363)$^b$ ND | — |
| | GN546 | Asymptomatic infected | 40,000†† | | | | Increased | — |
| | GN394 | Placentomeg/Asymp infected | 16,623 | | | | Reduced | — |

| Group | Plac/ No. | Outcome§ Placenta/ Fetus-Neonate | sFlt-1 AF* pg/ml | sFlt-1 serum pg/ml | bVEGF AF | bVEGF s PLGF$^a$ | Placemeg# (sFlt-1) | Placental Pathology†/ Compensation |
|---|---|---|---|---|---|---|---|---|
| HIG Therapy | P-15 | Placentomegaly/ Symptomatic: IUGR, Oligohydramnios, fetal microcephaly, ventriculomeg, hepatosplenomeg, calcificat, lissencephaly/ polymicrogyria | 62,912*** | 32,927*** | | 91$^a$ | Reduced AF factors: sFlt-1 21,421 bVEGF 4,095 | Moderate fibrosis & knotting, calcification§/38.2 villi/mm$^2$; 7.7 BV §AF: 146 pg/ml cmvIL-10 308,150 CMV ge/ml AF |
| | P-13 | Placentomeg/IUGR, Neonate (uninfected?) | 83,822*** | 10,603*** | 90,361 | 79$^a$ (900)$^b$ | Reduced Serum factors: sFlt-1 118 | §AF: 85 pg/ml cmvIL-10 4,310 CMV ge/ml AF |
| | | Placentomegaly/IUGR Asymptomatic infected | 85,858G*** | | 112,167G*** | 64,188 (9,000)G$^b$ | | Moderate fibrosis, High knotting, necrosis/ 60 villi/mm$^2$ |
| | P-9 | (Twin pregnancy) Girl infected | | 7,960*** | | 49G$^a$ | Reduced | |
| | | Boy uninfected | 34,462B*** | | 53,392B*** | 13B$^a$ (462)B$^b$ | | §AF: 313 pg/ml cmvIL-10 378,240 CMV ge/ml AF |
| | P-11 | Placentomeg/ Asymptomatic | 4,058 | | ND | 130$^a$ (80)$^b$ | | 272,750 CMV ge/ml AF |
| | P-12 | Placentomeg/ Asymptomatic infected | 78,327*** | 3,802*** | | 127$^a$ | Reduced | High fibrosis, mod. knots necrosis, calcification, leuk infiltrat/mod. # villi CMV DNA + AF |
| | GN400 | Placentomeg/ Asymptomatic | 86,585*** | | | (173)$^b$ | Reduced | — |
| | P-14 | Placentomeg/ Asymptomatic Oligohydramnios | 63,448*** | 4,259*** | 161,387*** | 27$^a$ (6,500)$^b$ | Reduced Serum factors: sFlt-1 278 | Moderate fibrosis/ 49.6 villi/mm$^2$; 7.1 BV 647,000 CMV ge/ml AF |
| | GN426 | Placentomeg/ Asymptomatic | 61,099*** | | | | Reduced | — |
| | GN452 | Placentomeg/ Asymptomatic | 51,708*** | | | (120)$^b$ | Reduced | — |
| | GN465 | Placentomeg/ Asymptomatic | 45,117†† | | | (80)$^b$ | Reduced | — |
| | P-10 | Placentomegaly/ Oligohydramnios, Neonate infected | 49,592*** | | 50,821 | 119$^a$ (94)$^b$ | Reduced AF factors: sFlt-1 7,909 bVEGF 3,827 | High fibrosis necrosis & calcification/ 62 villi/mm$^2$; 5.2 BV §AF: 55 pg/ml cmvIL-10 1,770 CMV ge/ml AF |

| Group | Placenta/ No. | Outcome§ Placenta/Fetus-Neonate | sFlt-1 AF* pg/ml | sFlt-1 sera pg/ml | bVEGF AF | bVEGF sera PLGF$^a$ AF | sEng$^b$ (pg/ml) | Placmeg# (sFlt-1) | Placental Pathology†/ Compensation |
|---|---|---|---|---|---|---|---|---|---|
| HIG Prevent | P-16 | Placentomegaly/ Neonate Uninfected | 1,118** | 4,204*** | 24,005†† | 60$^a$ | | Reduced | Minimal fibrosis High knotting/ 95.3 villi/mm$^2$; 4.4 BV |
| | P-18 | Neonate Uninfected | 6,765** | 1,071** | 4,803** | 231$^a$ | (9,100)$^b$ | ND | ND |
| | P-17 | Placentomegaly/ Neonate Uninfected | 35,274††¶ | 651** | 44,537††¶ | 58,232 53$^a$ | (6,200)$^b$ | Normal | Minimal fibrosis Moderate knotting/ 47.4 villi/mm$^2$; 8.7 BV |
| | P-19 | Placentomegaly/ Neonate Uninfected | 36,170††¶ | 11,386*** | 48,405††¶ | 17,583 | (1,223)$^b$ | Reduced | Minimal fibrosis/ 44 villi/mm$^2$; 10 BV |

TABLE 2-continued

| | | | | | | | |
|---|---|---|---|---|---|---|---|
| GN306 | Neonate Uninfected | 27,757 | | 68[a] | (425)[b] | ND | — |
| GN318 | Neonate Uninfected | 35,302 | | | (560)[b] | ND | — |

Abbreviations:
Plac, placenta,; GA, gestational Age; AF, amniotic fluid; sFlt-1, soluble Fms-like tyrosine kinase-1, i.e., soluble VEGF receptor 1; VEGF, vascular endothelial growth factor; bVEGF, bound VEGF (competitive ELISA measures bound and free VEGF); column labeled bVEGF, level in serum), Serum, maternal; Symp, Symptomatic; ge, CMV genome equivalents; TOP, termination of pregnancy; esoph, esophageal; —, placental biopsy specimen unavailable.
*See Graph 3. Level of sFlt-1 and bVEGF pg/ml in AF (20 wks GA) quantified before administration of treatment. Mean sFlt-1 pg/ml: Seronegative controls: 3,739; Untreated: 54,237; HIG-treated: 21,117. Mean bound VEGF pg/ml in AF of seronegative controls: 6,173.
Mean PLGF pg/ml in AF of seronegative controls, normal values about 142 pg/ml; PE <90 pg/ml [Levine, 2004 #850].
[a]PLGP levels in AF.
[b]sEng, soluble endoglin (pg/ml) measured in AF were low as compared with material sera in PE [Venkatesha, 2006 #934].
§Quantitative ELISA for cmvIL-10 (detection limit approximately 50 pg/ml) [Yamamoto-Tabata, 2004 #6079].
¶Factors in amniotic fluid quantified following 2 or 3 HIG treatments (P-17, P-19).
Placentomeg, placentomegaly: increased vertical thickness associated with fibrosis, inflammation and edema [La Torre, 2006 #1062].
†See FIG. 11. Quantification of fibrinoids/mm2 and fields with large fibrinoids (%).
¥See FIGS. 12 and 13. Quantification of villi and blood vessels per villus.
**Green: seronegative controls, normal levels.
***Red: exceptionally high levels, symptomatic disease.
††Blue: moderate levels, with or without fetal infection.

Example 8

Indicators of placental dysfunction associated with congenital CMV Infection

Altered levels of angiogenic factors VEGF and PlGF and their antagonist sFlt-1 in amniotic fluid reflect pathological conditions in the placental-fetal unit. Additionally, it has been shown that the ratio of sFlt-1 to PlGF can be measured in order to evaluate the balance of angiogenic factors in amniotic fluid (Levine et al. (2006) *N Engl J Med* 355:992-1005). Therefore, we evaluated whether sFlt-1/PlGF ratios correlated with congenital CMV infection.

Figure 15:
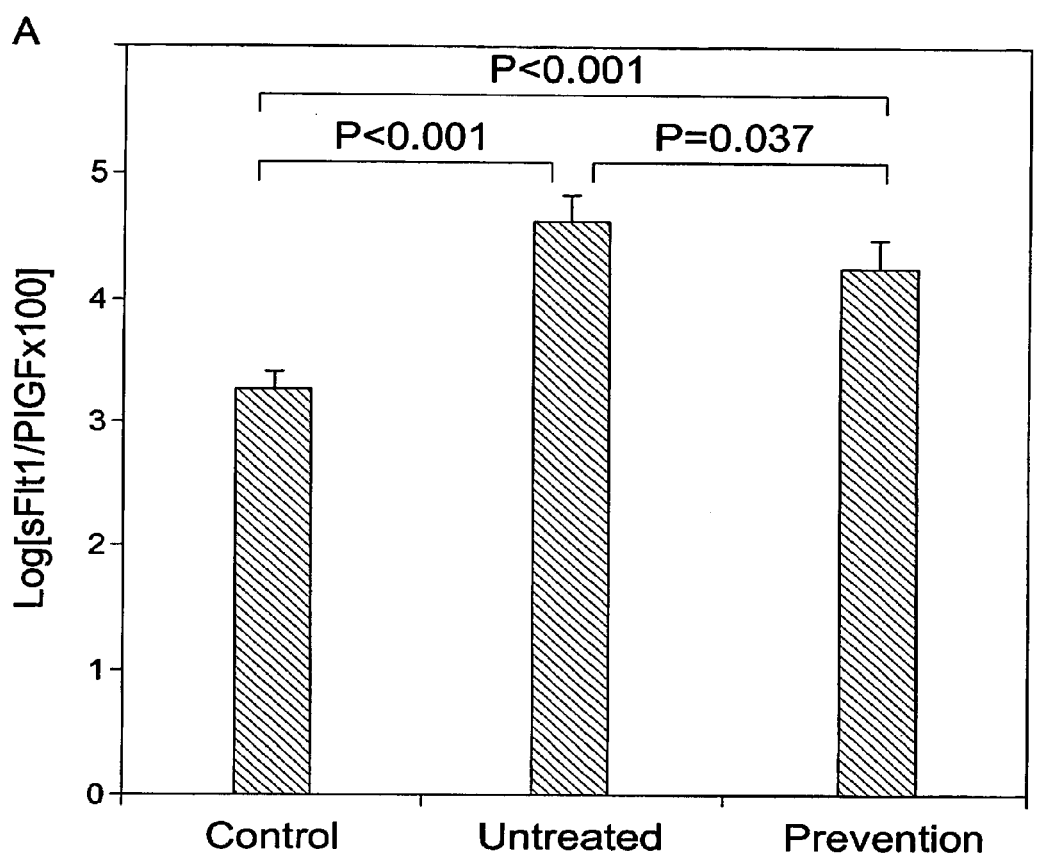
FIG. 15A-B: Increased sFlt-1 to PlGF ratios in amniotic fluid from congenital CMV infection suggest altered homeostasis of angiogenic factors that correlates with fetal outcome. A (top panel): The mean ratio of sFlt-1-to-PlGF after logarithmic transformation in healthy control group (n=7), infected untreated (n=38), and early HIG treated prevention group (n=9). The results are represented as mean±SEM and compared between the groups using Student t=test for independent samples. The differences were significant between the control and untreated groups (P<0.001), control and prevention groups (P<0.001), and untreated and prevention groups (P=0.037). B (bottom panel): Fetal outcome in healthy control, infected untreated, and early HIG-treated prevention groups was evaluated for the symptoms of placentomegaly, oligohydramnios, IUGR, CMV DNA, and brain disease. Scoring was 0 for no symptoms and 1 for presence of symptoms. Outcome score was expressed as mean±SEM.
Figure 15:
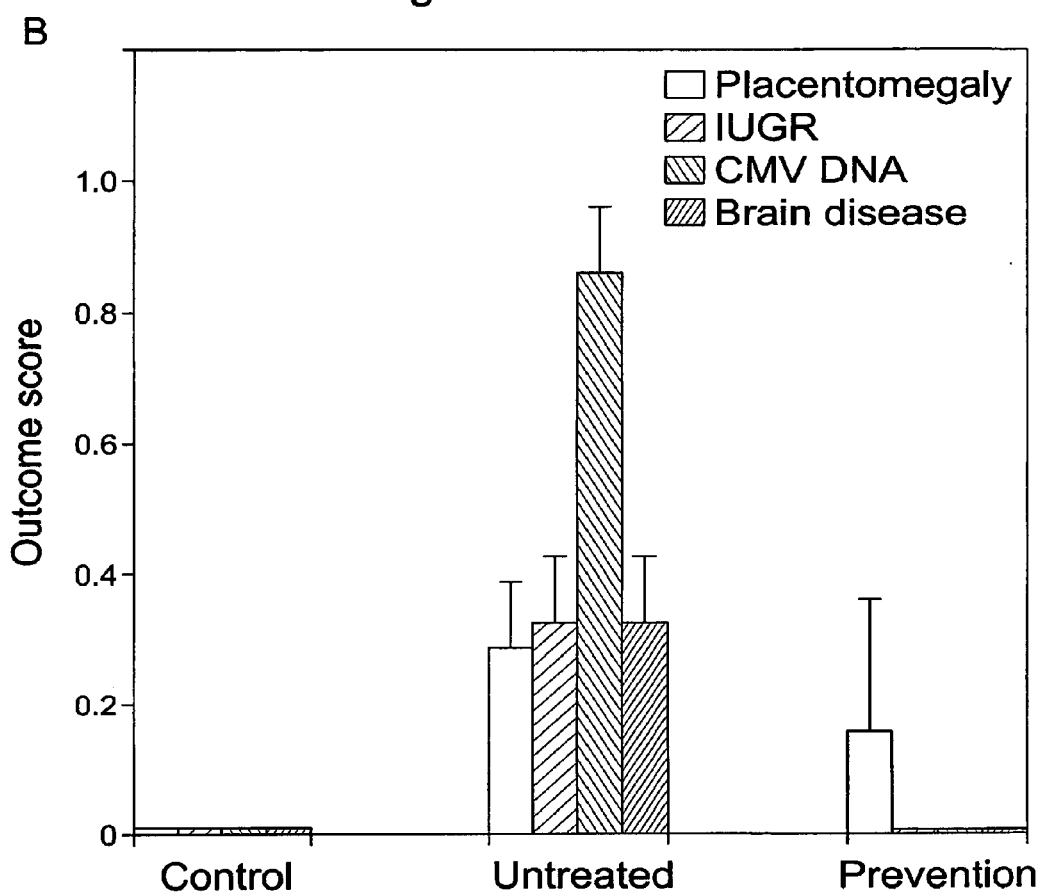

Fifty-four amniotic fluid samples from control, untreated CMV, and HIG-prevention groups were tested for concentrations of sFlt-1 and PlGF using ELISA. FIG. 15A shows the mean sFlt-1/PlGF ratios after logarithmic transformation for the control, untreated CMV, and HIG-prevention groups. We found that the sFlt-1/PlGF ratio was significantly elevated in amniotic fluid from untreated CMV infection as compared with the control group (P<0.001) and from HIG-prevention group as compared with the control group (P<0.001). These analyses revealed the sFlt-1/PlGF ratio was significantly lower after HIG treatment as compared with untreated CMV infection (P=0.037).

Our results suggest that the levels of sFlt-1 induced in congenital CMV infection exceed the amounts of VEGF produced, resulting in a net anti-angiogenic state. In contrast, HIG treatment reduces viral replication and inflammation, resulting in a net angiogenic state.

Next we evaluated whether sFlt-1/PlGF ratios correlated with fetal symptoms at delivery. Symptoms of congenital infection at birth can be temporary and resolve soon after birth (e.g. IUGR, hepatomegaly, and splenomegaly), or alternatively, can be permanent birth defects (e.g. brain disease and mental retardation). We evaluated and scored clinical manifestations associated with congenital infection (placentomegaly, IUGR, fetal infection—CMV DNA positive, and brain disease) in control, untreated CMV, and HIG-prevention groups. Each present symptom was scored with a value of 1, and absence of a symptom was scored as 0. Data were expressed as outcome scores and represented as a graph (FIG. 15B). With the exception of placentomegaly, fetal symptoms clustered in the untreated CMV infected group with the highest sFlt-1/PlGF ratio (FIG. 15A). In dramatic contrast, the HIG-prevention group were completely asymptomatic of congenital infection symptoms, in accord with significantly lower sFlt-1/PlGF ratios.

Our results indicate that amniotic fluid from untreated congenital CMV infection contains significantly elevated sFlt-1/PlGF ratios that correlate with placental dysfunction (e.g. placentomegaly and IUGR), viral replication in the placenta, and transplacental fetal infection (e.g. CMV DNA in circulation and brain disease). In the prevention group, early HIG treatment significantly reduced sFlt-1/PlGF ratios and significantly prevented fetal infection as compared with the untreated group. We anticipate that sFlt-1/PlGF ratios could be used to diagnose CMV infection, and that efficacy of treatment for CMV infection could be measured by evaluating the change in sFlt-1/PlGF ratios in a subject at different timepoints.

Example 9

Indicators of Maternal Endothelial Cell Dysfunction Associated with Congenital CMV Infection As noted above, severe congenital CMV infection has been cited as a cause of Mirror syndrome with a preeclampsia phenotype in the mother (Rana et al., 2007). Rana et al. found that before delivery, maternal serum from a CMV infected patient contained extremely high levels of sFlt-1 (116.5 ng/mL) in contrast to normal pregnancy (19.3 ng/mL) and preeclampsia (66.0 ng/mL). Likewise, soluble endoglin was elevated (107.4 ng/mL) in contrast to normal pregnancy (18.7 ng/mL) and preeclampsia (52.6 ng/mL). The values of sFlt-1 and soluble endoglin in cord blood were relatively low at 2.1 ng/mL and 8.2 ng/mL, respectively.

Endoglin, a homodimeric transmembrane glycoprotein, is expressed on the surface of endothelial cells and is a part of a TGF-beta receptor complex (Barbara et al. (1999) *J Biol Chem* 274:584-594; Gougos and Letarte (1990)*J Biol Chem* 265:8361-8364). Tissue expression of endoglin is increased during angiogenesis, wound healing, inflammation, and hypoxia (Duff et al. (2003) *Faseb J* 17:984-992; Fonsatti and Maio (2004) *J Transl Med* 2:18; Sanchez-Elsner et al. (2002) *J Biol Chem* 277:43799-43808), and its soluble form (sEng) has an anti-angiogenic effect that may contribute to preeclampsia (Levine et al. (2004) *N Engl J Med* 350:672-683). In addition, we recently reported that CMV induces expression of integrin beta 6 that activates TGF-beta in infected endothelial cells and was observed at focal sites of injury in the vasculature of placentas infected in utero (Tabata et al. (2008) *Am J Pathol* 172:1127-1140).

Figure 16:
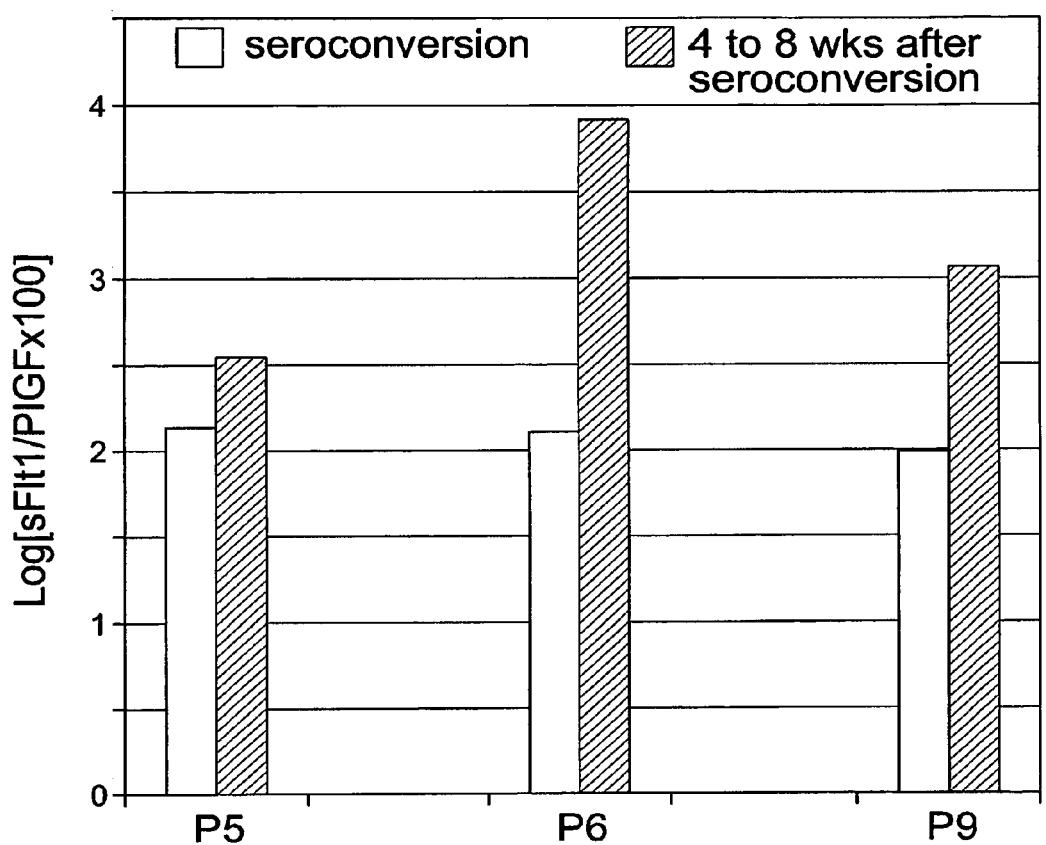
FIG. 16: Increased sFlt-1/PlGF ratios in maternal sera indicate altered homeostasis of angiogenic factors associated with congenital CMV infection. The ratio of sFlt-1-to-PlGF after logarithmic transformation in maternal sera from three patients (P5, P6, and P9) at the time of seroconversion (blue) and 4 to 8 weeks later (red).

We evaluated the expression of anti-angiogenic factors in maternal blood from congenital CMV infection. We quantified the sFlt-1/PlGF ratio in sequential maternal sera from control (P5), congenital CMV infection (P6), and HIG prevention (P9) groups. Although few samples were studied, the sFlt-1/PlGF ratio increased from 4 to 8 weeks after seroconversion (FIG. 16). At a time near seroconversion, the sFlt-1/PlGF ratios for the CMV infection group were comparable to the healthy control (2.5) and a few prevention samples (1.9); several samples in the HIG-prevention group showed higher ratios (3.3-3.4) that might suggest active homeostasis.

Next we measured sEng in 22 paired maternal and cord blood sera from placentas at delivery. Dramatically elevated levels of sEng (40-200 ng/mL) in maternal sera were found associated with several CMV DNA positive samples and viral replication in affected placenta, detected by PCR analysis and immunoblot analysis using recomBlot kit (Mikrogen). In contrast, cord blood sera showed very low levels of sEng (2-3 ng/mL). Maternal serum from a known case of diagnosed primary placental CMV infection at 19 weeks' gestational age showed viral replication in the placenta and had enormously high levels of sEng (<250 ng/mL) at delivery. We plan to correlate the levels of sEng and sFlt-1/PlGF ratios with the serological evaluation and PCR analysis.

Our results suggest that detection of elevated anti-angiogenic factors (sFlt-1/PlGF ratio and sEng) in maternal blood, along with serological analysis, may be a sensitive early indicator of congenital CMV infection. Importantly, the detection of these elevated anti-angiogenic factors could be used to diagnose CMV infection.

Example 10

CMV-infected HUVECs Express $\alpha v \beta 6$

The present example demonstrates that CMV-infected endothelial cells from pulmonary, uterine, and placental blood vessels activate TGF-$\beta$1 through the induction of the epithelial integrin $\alpha v \beta 6$, promoting signaling through ALK5 and Smad3. This signaling pathway plays a fundamental role in mediating profibrotic responses at later times after infection. In this example, immunohistochemical analysis of CMV-infected tissues showed integrin $\alpha v \beta 6$ expression in both epithelial and endothelial cells proximal to infected foci and sites of injury. These results suggest that integrin $\alpha v \beta 6$-mediated TGF-$\beta$1 activation could be relevant to the development of fibrosis in persistent infection (See also, Tabata et al., Am J Pathol. 2008 April; 172(4):1127-40).

Figure 17:
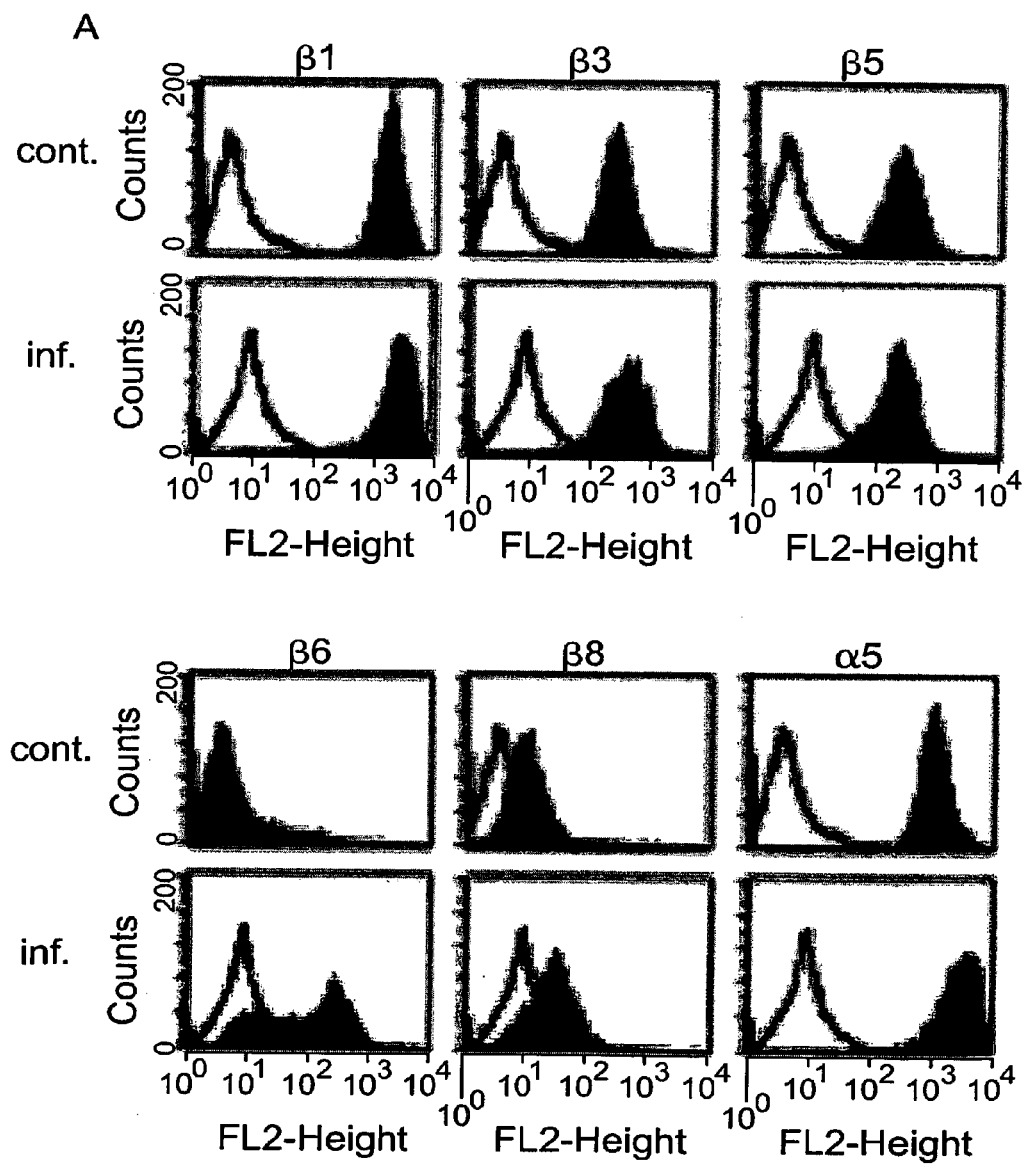
FIG. 17: CMV strain VR1814-infected HUVECs induce integrin αvβ6 expression at late times. A: Flow cytometric analysis of integrin subunits β1, β3, β5, β6, β8, and α5 in HUVECs at 10 days after infection. Experiments were repeated at least five times. Typical histograms from control (cont.) and infected (inf.) HUVECs are shown. Shaded areas represent expression of specific proteins. Lines represent isotype control. B: Flow cytometric analysis of integrin αvβ6 in HUVECs at 3, 5, 7, and 10 days after infection (dpi) and control (cont). Typical histograms are shown. Shaded areas represent expression of specific proteins. Lines represent isotype control. Experiments were repeated at least four times. C: Cell lysates (100 μg) from control or infected HUVECs at 10 days after infection were immunoblotted with an anti-integrin βvβ6 (2A1) and anti-actin antibodies as a loading control. Molecular mass (kDa) is shown on the left.
Figure 17:
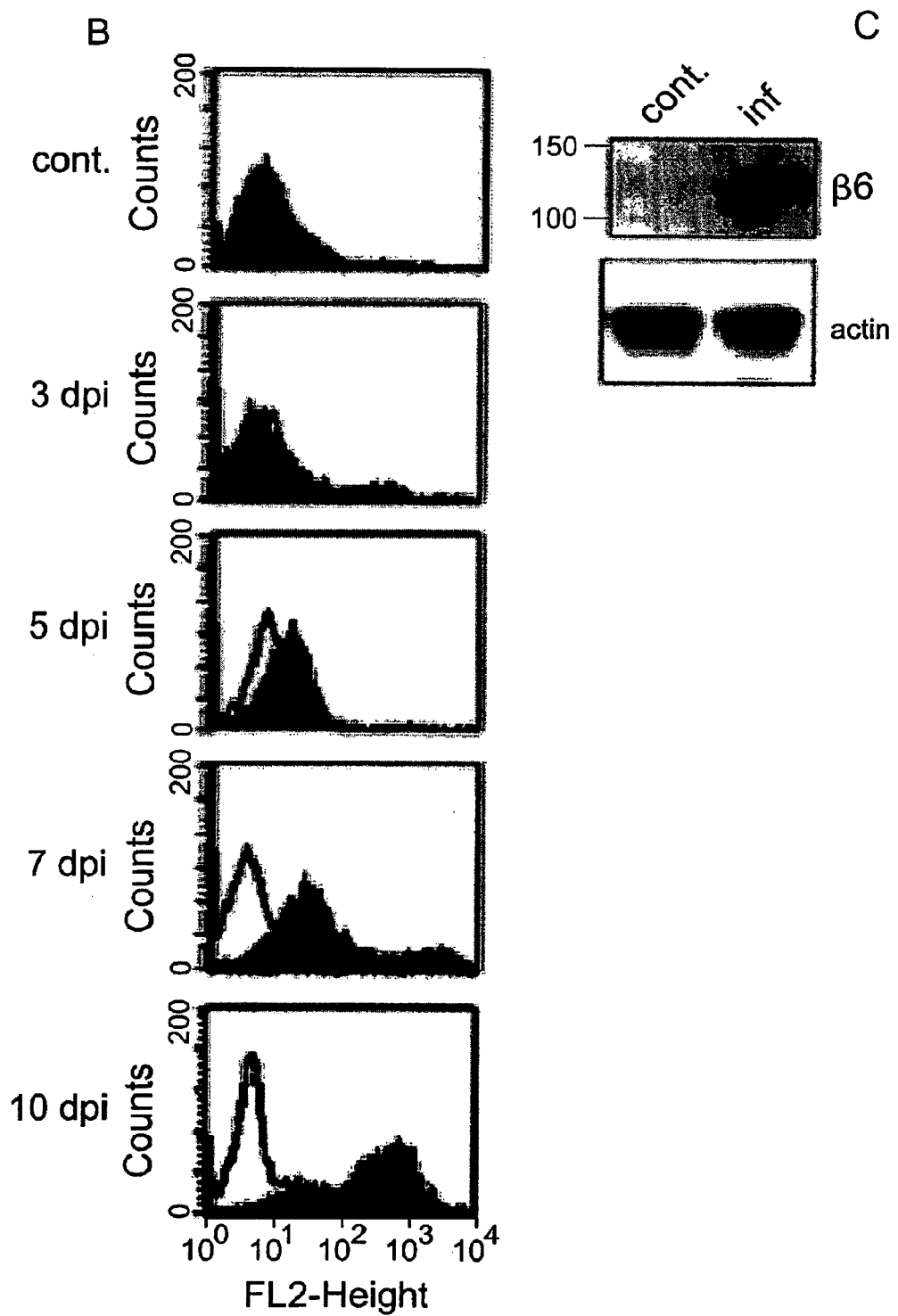

Previous investigators reported that human fibroblasts infected with a laboratory CMV strain expressed TGF-$\beta$1 transcripts and protein, but they did not examine activation of the latent protein (Michelson et al, J Virol, 68:5730-5737 (1994); Yoo et al., J Virol, 70:7062-7070 (1996)). The propeptide of TGF-$\beta$1, latency-associated peptide-$\beta$1, contains an Arg-Gly-Asp (RGD) motif that is recognized by a subset of integrins having in common the integrin $\alpha v$ subunit (Munger et al., Cell, 96:319-328 (1999); Mu et al., J Cell Biol, 157: 493-507 (2002); Munger et al., Mol Biol Cell, 9:2627-2638 (1998); Lu et al., J Cell Sci, 115:4641-4648 (2002); Ludbrook et al., Biochem J, 369:311-318 (2003)) and $\alpha 5 \beta 1$ (Asano et al., Arthritis Rheum, 52:2897-2905 (2005)). Furthermore, the integrins $\alpha v \beta 6$ and $\alpha v \beta 8$ have been shown to activate TGF-$\beta$1 in vivo (Munger et al., Cell, 96:319-328 (1999); Mu et al., J Cell Biol, 157:493-507 (2002)). To examine whether CMV infection alters the expression level of $\alpha v$ integrin $\beta$ subunit partners and integrin $\alpha 5$, HUVECs were infected with VR1814, a pathogenic clinical CMV strain, and quantified the surface expression of integrins $\beta 1$, $\beta 3$, $\beta 5$, $\beta 6$, $\beta 8$, and $\alpha 5$ by flow cytometry at 10 days after infection. Level of infectivity was evaluated by immunofluorescence staining and flow cytometric analysis of CMV gB expression at the cell surface. The results showed nuclear immunofluorescence of CMV IE1 and IE2 proteins and cytoplasmic gB staining in >90% of infected cells. Flow cytometry detected surface expression of gB in 60.8±6.3% of infected cells. In control uninfected HUVECs, integrin subunits $\beta 1$, $\beta 3$, $\beta 5$, and $\alpha 5$ were expressed abundantly, but there was no expression of $\beta 6$ and only minimal expression of integrin $\beta 8$ (FIG. 17A). Integrin $\beta 6$, whose expression is considered restricted to epithelial cells, was strongly induced in CMV-infected HUVECs, whereas levels of integrins $\beta 1$, $\beta 3$, $\beta 5$, $\beta 8$, and $\alpha 5$, as well as $\alpha v$ (data not shown), were unchanged. An analysis of the kinetics of integrin $\beta 6$ induction in infected HUVECs showed that the protein was increasingly detected from 5 to 10 days after infection (FIG. 17B). Expression of integrin $\beta 6$ was confirmed at 10 days by immunoblot analysis (FIG. 17C). These data suggested that integrin $\alpha v \beta 6$, aberrantly expressed in infected HUVECs, participates in TGF-$\beta$1 activation. Subsequent investigations focused on assessing integrin $\alpha v \beta 6$ function in infected HUVECs.

Example 11

CMV Induces Integrin $\beta$6-Dependent TGF-$\beta$1 Activation

Figure 18:
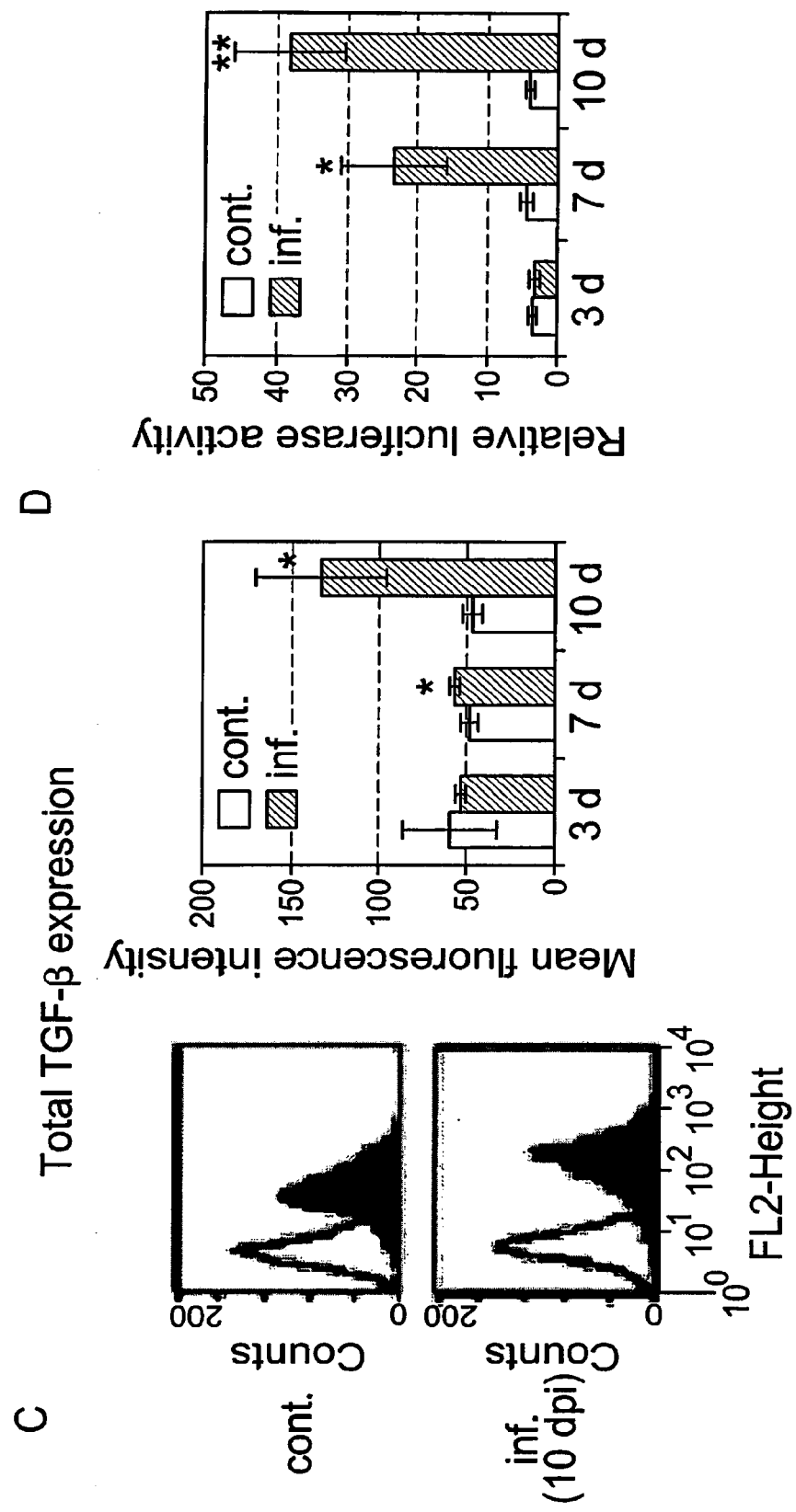
FIG. 18: Integrin βvβ6-dependent TGF-β1 activation in CMV-infected HUVECs. A: TGF-β1 production by infected HUVECs. Conditioned medium was collected from control (open circles) and infected (filled circles) HUVECs at 1 to 9 days, and TGF-β1 was quantified by enzyme-linked immunosorbent assay. Results are the mean (±SE) of three experiments done in duplicate. Asterisks indicate the amount of TGF-β1 in infected HUVECs as compared with uninfected controls (*P<0.05, **P<0.01). B: Surface expression of TGF-β1 in HUVECs was analyzed by flow cytometry at 3, 7, and 10 days after infection and controls (cont). Typical histograms are shown. Shaded areas represent expression of specific proteins. Lines represent isotype control. Experiments were repeated at least three times. C: Total TGF-β1 was analyzed by flow cytometry using permeabilized cells at 3, 7, and 10 days after infection (inf.) and controls (cont). Left: Typical histograms at 10 days are shown. Shaded areas represent expression of specific proteins. Lines represent isotype control. Right: Results are the mean fluorescence intensity (±SE) of three experiments. Asterisks indicate expression in infected HUVECs as compared with uninfected controls (*P<0.05). D: TGF-β bioassay of active TGF-β produced by infected HUVECs. Equal numbers of TMLC TGF-β reporter cells, and control (cont.) or infected HUVECs (inf.) were cultured for 1.6 to 24 hours at 3, 7, and 10 days after infection. Relative luciferase activity in cell lysates was defined as the measured activity divided by TMLC baseline activity. Results are the mean (±SE) from 6 to 11 experiments done in duplicate. Asterisks indicate the TGF-β1 activity in infected HUVECs as compared with uninfected controls (*P<0.05, **P<0.001). E: Inhibition of luciferase activity in TGF-β bioassay by anti-integrin αvβ6. HUVECs infected for 10 days were co-cultured with TMLCs with anti-TGF-β neutralizing antibody (1D11); function-blocking anti-αvβ6 antibody (3G9); isotype-matched, non-function-blocking anti-αvβ6 antibody (CSβ6); or mouse IgG1 isotype control antibody (control Ab). Results are the mean (±SE) from three to five experiments done in duplicate. Asterisks indicate inhibition of TGF-β1 activation relative to untreated infected HUVECs (*P<0.05, P<0.01, *P<0.001).
Figure 18:
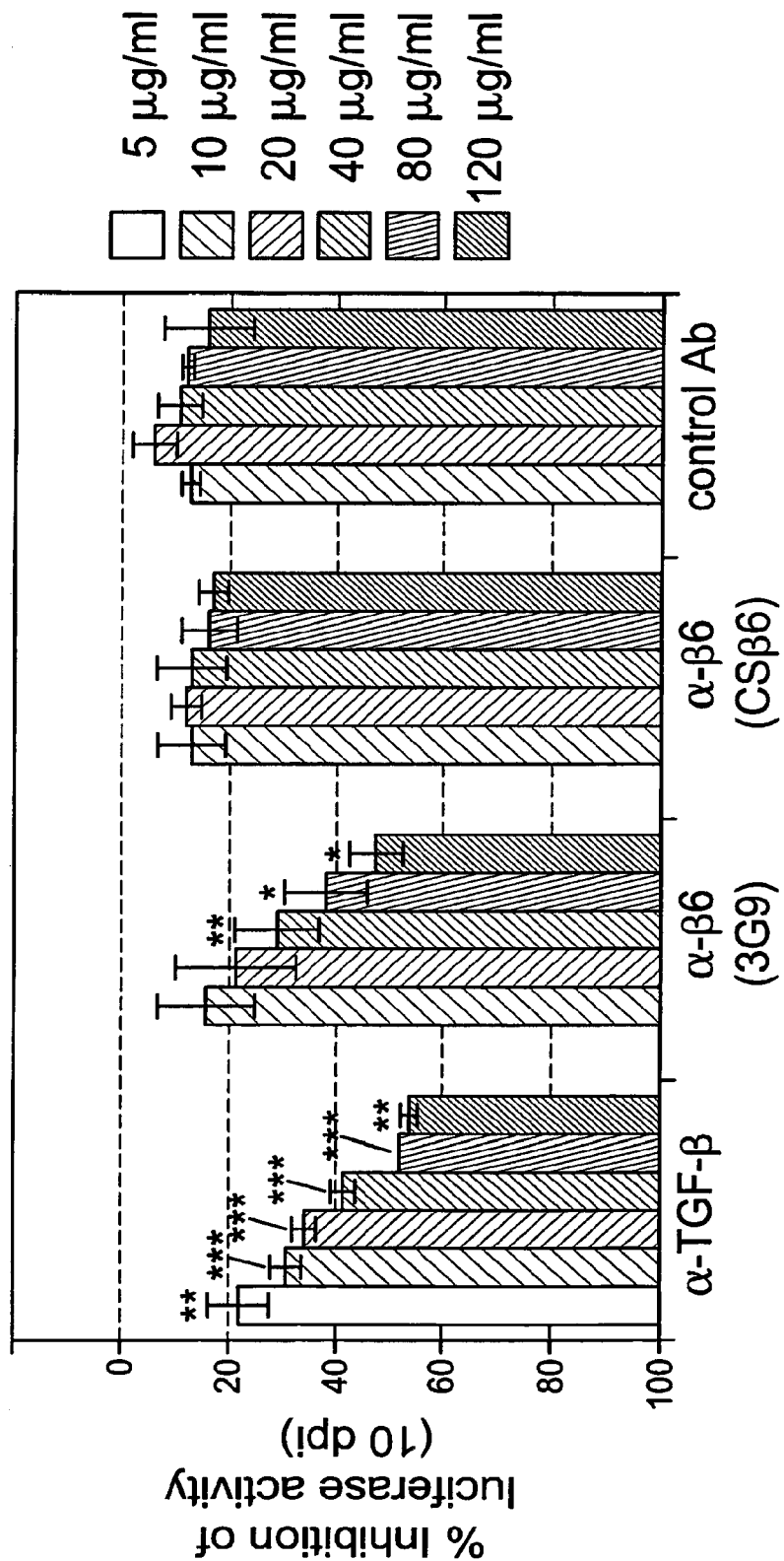

In the present example, it was assessed whether integrin $\alpha v \beta 6$ in HUVECs induced by CMV activates TGF-$\beta$1. First, the level of TGF-$\beta$1 released into the medium from CMV-infected HUVECs and uninfected control cells was quantified. After day 1, conditioned medium from infected and control cells was collected on alternate days and frozen. To quantify TGF-$\beta$1 by enzyme-linked immunosorbent assay, conditioned medium was acid-treated to convert the latent TGF-$\beta$1 to the immunoreactive form. Increasing amounts of TGF-$\beta$1 were secreted from HUVECs as early as 3 days after infection (FIG. 18A). Significantly more TGF-$\beta$1 was released from cells at 5 to 7 days after infection. In contrast, control cells did not show any increase in the amounts of soluble TGF-$\beta$1 in a comparable culture period (FIG. 18A).

Because secretion of TGF-$\beta$1 is increased by infection, it was then asked how much surface (ie, bound) and total cellular TGF-$\beta$1 was present by flow cytometry. Surface expression of TGF-$\beta$1 on infected cells was increased at 7 to 10 days after infection, whereas no change was observed in uninfected control cells (FIG. 18B). Expression of total TGF-$\beta$1 in infected cells was significantly increased at 10 days after infection (FIG. 18C).

To determine whether CMV activates TGF-$\beta$1, HUVECs were co-cultured with TMLCs. At 3, 7, and 10 days after infection, control HUVECs or infected cells were trypsinized and then co-cultured with TMLCs for 16 to 24 hours before measurement of luciferase activity in cell lysates. We found a dramatic increase in luciferase activity, indicating TGF-$\beta$1 activation, in 7- to 10-day-infected HUVECs co-cultured with TMLCs (FIG. 18D). Little luciferase activity was observed in control HUVECs co-cultured with TMLCs (FIG. 18D). We then tested whether the increased luciferase activity is dependent on TGF-$\beta$1 or integrin $\alpha v \beta 6$. HUVECs infected for 10 days were co-cultured with TMLCs, with or without function—blocking antibodies against either TGF-$\beta$ (1D11) or $\alpha v \beta 6$ (3G9). Negative controls included isotype-matched, non-function-blocking antibodies with either unrelated specificity or non-function-blocking specificity against $\alpha v \beta 6$ (CS$\beta$6). The increase in luciferase activity was partly abrogated by function-blocking anti-TGF-$\beta$ (1D11) and anti-$\beta$6

(3G9) but not by control antibodies (CSβ6 or isotype control) (FIG. 18E), indicating that TGF-β1 activation after CMV infection is at least integrin αvβ6-dependent. Although the inhibition of luciferase activity by neutralizing antibodies was dose-dependent, even very high concentrations of anti-TGF-β were able to reduce luciferase activity by only about 50% compared with untreated cells, suggesting that CMV may also activate the plasminogen activator-1 promoter through a mechanism not dependent on TGF-β1.

Example 12

CMV-Infected HUVECs Undergo ALK5/Smad3 Signaling

Figure 19:
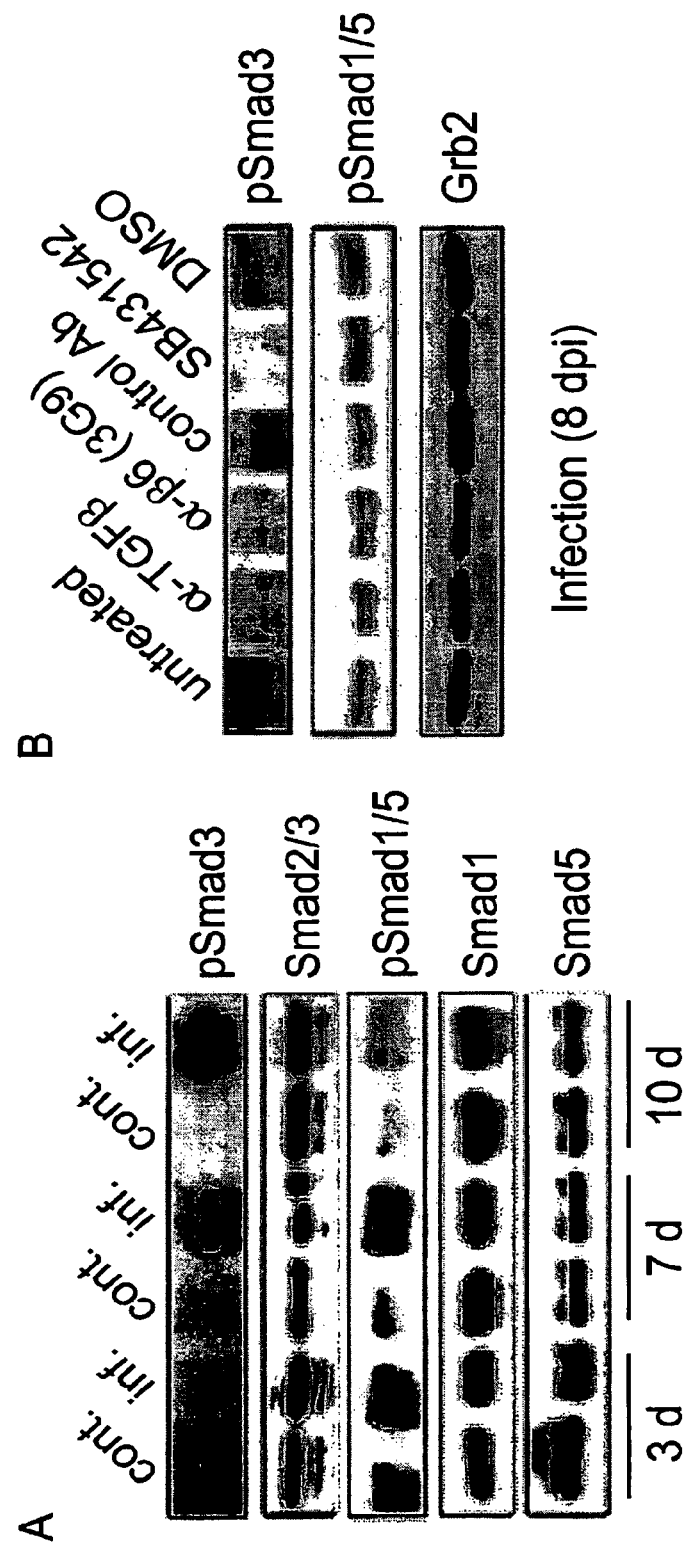
FIG. 19: CMV-infected HLTVECs induce Smad3 phosphorylation. A: Cell lysates from control (cont.) or infected (inf.) HUVECs at 3, 7, and 10 days after infection were fractionated by 10% SDS-PAGE and blotted on nitrocellulose. Phosphorylation of Smad3 (pSmad3) and Smad1/5 (pSmad1/5) was analyzed by immunoblotting using phospho-specific Smad3 and Smad1/5/8 (pSmad1/5) antibodies. Equal loading of the gels was confirmed using Smad2/3, Smad1, and Smad5 protein levels. B: Effects of anti-TOE-0 antibody, anti-αvβ6 antibody (3G9), and ALK5 kinase inhibitor on Smad3 phosphorylation. Infected HUVECs were cultured without antibody (untreated) or with anti-TGF-1 neutralizing antibody (1D 11, 40 µg/ml), function-blocking anti-αvβ6 antibody (309, 80 µg/ml), mouse IgG1 isotype control antibody (control Ab, 80 µg/ml), the ALK5 kinase inhibitor 513431542 (2.5 µmol/L), or the vehicle DMSO for 8 days. Lysates were fractionated by 10% SDS-PAGE and blotted. Filters were incubated with antibodies to phosphorylated Smad3 (pSmad3), phosphorylated Smad1/5/8 (pSmad1/5), and Grb2 (loading control). Results are representative of at least four independent experiments.

Activated TGF-β1 can bind the type I receptors ALK1 and ALK5, which then phosphorylate the transcriptional activators Smad1/5 and Smad2/3, respectively (ten Dijke, P. and Hill, C. S., *Trends Biochem Sci*, 29:265-273 (2004)). To determine which of these TGF-β1 signaling pathways is activated in CMV-infected HUVECs, Smad1/5 and Smad3 phosphorylation was analyzed by immunoblotting with antibodies specific to Smads and their phosphorylated forms (FIG. 19A). Smad3 phosphorylation was strongly detected in 7- and 10-day-infected cells. In contrast, only weak staining for phosphorylated Smad1/5 was observed, and this level either did not change or was decreased at 10 days after infection. Phosphorylated Smad1/5 was also weakly detected in the control. Protein levels of Smad1, Smad5, and Smad2/3 were the same in both infected and control cells.

To determine the relative contributions of TGF-β1 and αvβ6 to the observed ALK5 and Smad3 signaling, we performed function-blocking experiments using anti-TGF-β (1D11) and anti-αvβ6 (3G9) antibodies in 8-day infected HUVECs. Both neutralizing antibodies blocked Smad3 phosphorylation, whereas the isotype control antibody had little effect (FIG. 19B). Treatment of infected cells with the ALK5 kinase inhibitor SB431542 also prevented Smad3 phosphorylation (FIG. 19B). Phosphorylation of Smad1/5 was not blocked by treatment with these neutralizing antibodies, suggesting that the activation of Smad1/5 depends on a separate pathway. Together the results of these experiments show that CMV-infected HUVECs release increasing amounts of TGF-β1 and activate TGF-β1 through an integrin αvβ6-mediated mechanism that stimulates ALK5 signaling and downstream Smad3 phosphorylation.

Example 13

Figure 20:
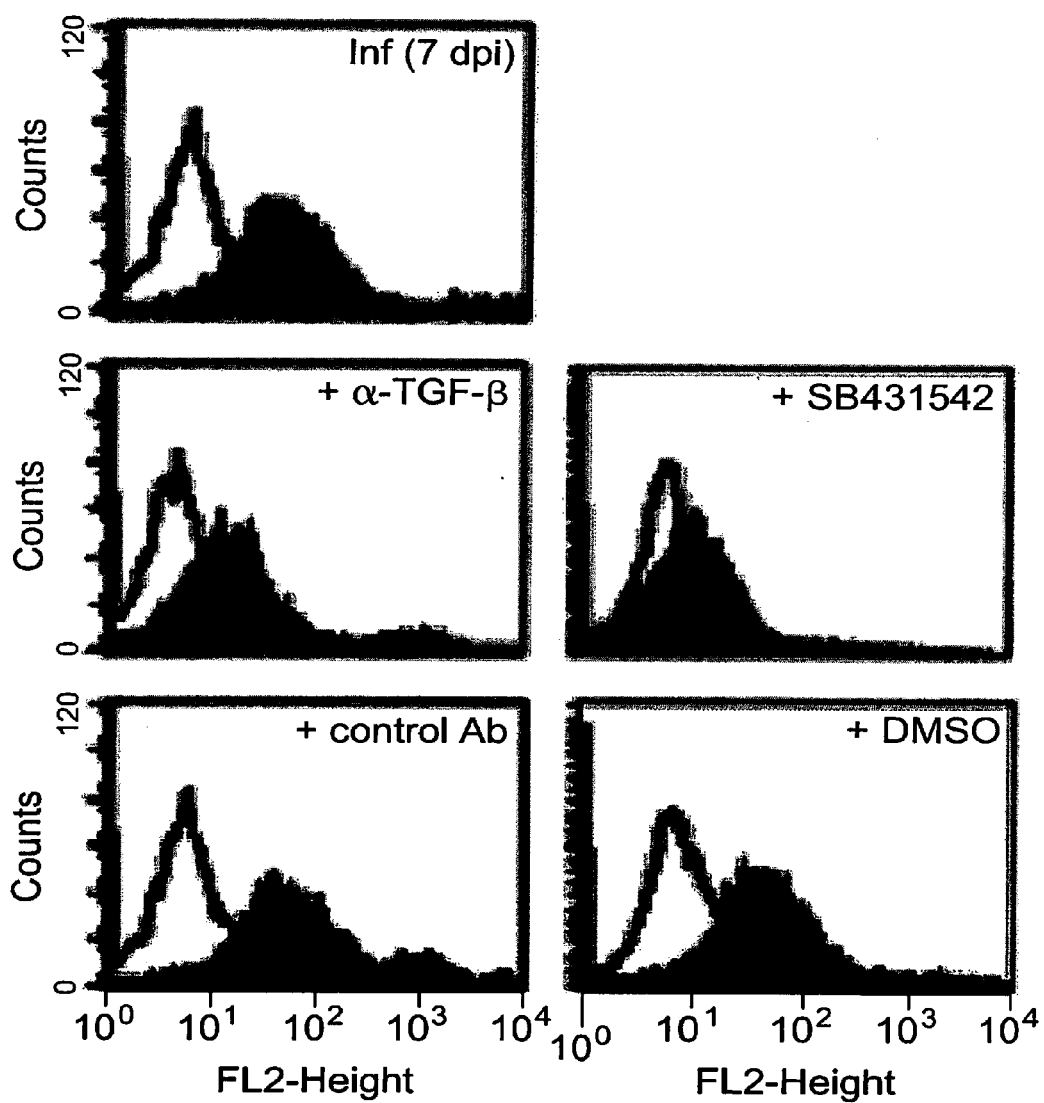
FIG. 20: Induction of integrin αvβ6 expression requires TGF-β signaling and viral DNA replication A: Infected HUVECs were cultured with or without chicken anti-TGF-β polyclonal antibody (20 µg/ml), chicken IgY isotype control antibody (control Ab, 20 µg/ml), the ALK5 kinase inhibitor SB431542 (0.5 µmol/L), or the vehicle DMSO for 7 days, and surface expression of integrin αvβ6 was analyzed by flow cytometric analysis. Typical histograms are shown. Shaded areas represent expression of specific proteins. Lines represent isotype control. Experiments were repeated at least two times. B: Surface expression of integrin αvβ6 was analyzed by flow cytometric analysis at 7 days after infection with or without viral DNA polymerase inhibitors, Foscarnet, and phosphonoacetic acid (PAA). Typical histograms are shown. Shaded areas represent expression of specific proteins. Lines represent isotype control. Experiments were repeated six times. C: Active TGF-β was not produced by infected HUVECs in the presence of viral DNA polymerase inhibitors. Equal numbers of TMLC TGF-β reporter cells and control (cont.) or infected HUVECs were cultured for 16 to 24 hours at 7 days after infection. Relative luciferase activity in cell lysates was defined as the measured activity divided by TMLC baseline activity. Representative data (mean±SE) are from four experiments done in triplicate.
Figure 20:
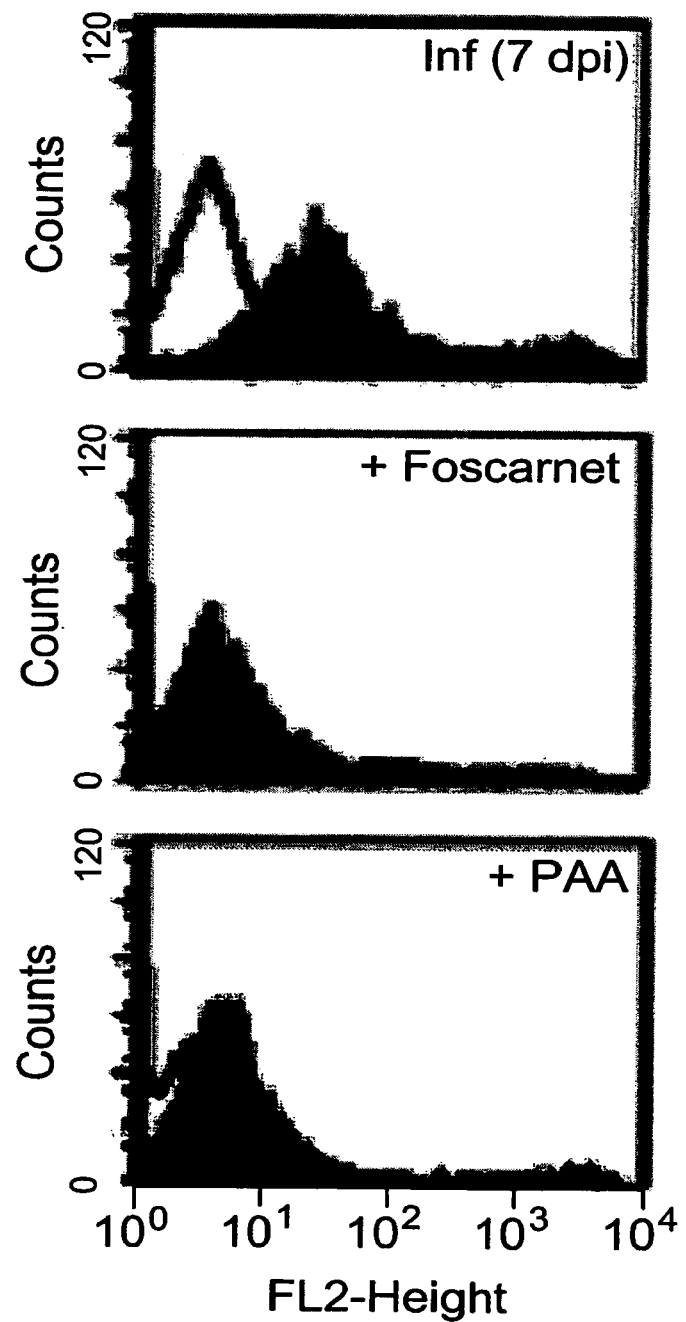
Figure 20:
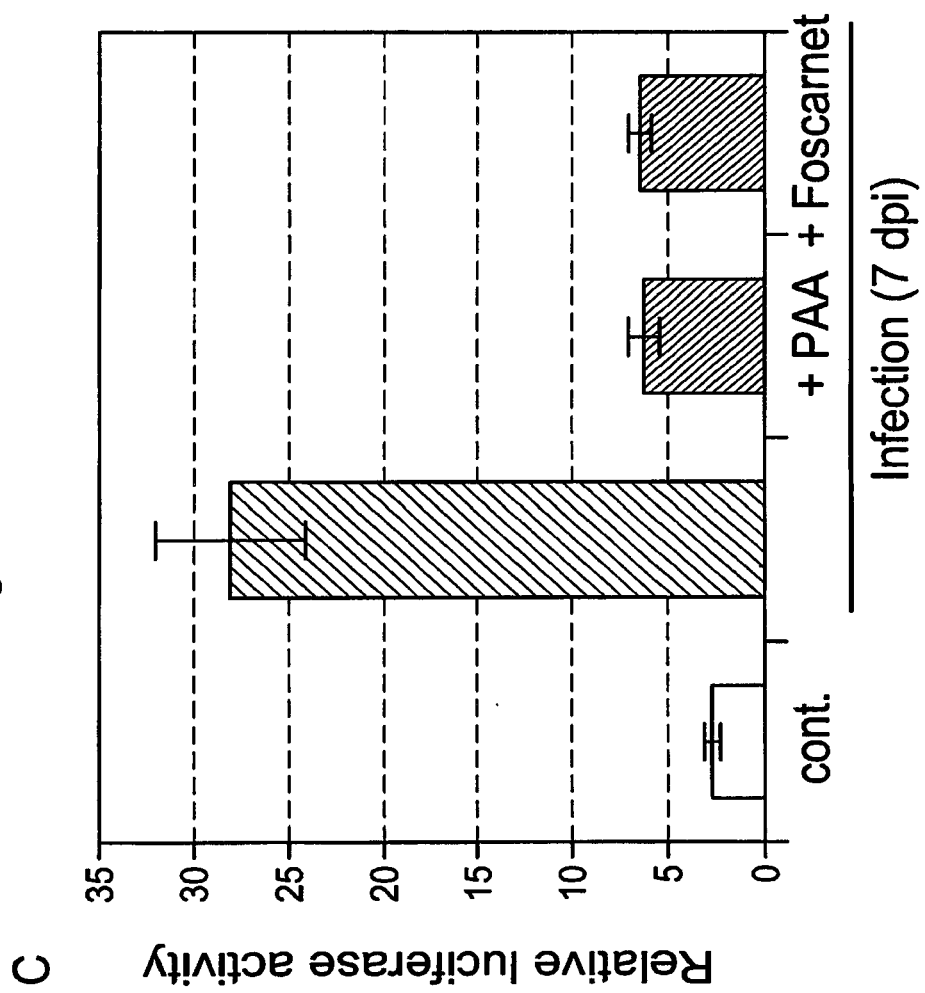

Induction of Integrin β6 Requires TGF-β/ALK5 Signaling and Viral DNA Replication The present example assesses how integrin β6 is induced on CMV infection in HUVECs. It has been reported that TGF-β1 induces de novo synthesis of integrin β6 in normal human keratinocytes (Zambruno et al., *J Cell Biol*, 129:853-865 (1995)) and strongly up-regulates its expression in primary cultures of human airway epithelial cells (Wang et al., *Am J Respir Cell Mol Biol*, 15:664-672 (1996)). Having found increased secretion of TGF-β1 in infected cells as early as 3 days after infection (FIG. 18A), it was then investigated the effect of TGF-β1 on induction of integrin β6. As expected, expression of integrin β6 was greatly reduced (by about 70%) by treatment with the anti-TGF-β neutralizing antibody (FIG. 20A). In addition, the ALK5 kinase inhibitor SB431542 (0.1 μmol/L to 1 μmol/L) was able to increasingly block the induction of integrin β6 with increasing inhibitor concentrations and nearly abolish it at high concentrations, whereas the control solution, containing the same concentration of the solvent dimethyl sulfoxide had no effect (FIG. 20A). Next, we investigated whether soluble factors participate in the induction of integrin β6. After day 1, conditioned medium from infected cells was collected on alternate days and frozen. HUVECs were cultured with the filtered conditioned medium for 8 days, and expression of integrin β6 was analyzed. No integrin β6 expression was observed in cells cultured with conditioned medium from any time point, even though the secretion of TGF-β1, which could be mostly present in an inactive form, from infected cells increased throughout time. It was then determined whether viral late gene expression is required for the up-regulation of integrin β6 in infected cells because the expression was observed only at late times after infection. HUVECs were infected and cultured in the presence of the viral polymerase inhibitors Foscarnet (400 μmol/L) or phosphonoacetic acid (100 μg/ml). Both viral polymerase inhibitors blocked induction of integrin β6 (FIG. 20B) and strongly suppressed induction of TMLC luciferase activity (FIG. 20C). The remaining luciferase activity was further reduced by the addition of an anti-TGF-β antibody, but not by an anti-integrin β6 neutralizing antibody (3G9), indicating that increased luciferase activity was not attributable to integrin αvβ6-mediated TGF-β1 activation. Together, these results indicate that TGF-β1/ALK5 signaling and viral DNA replication are important factors for the induction of integrin β6 in HUVECs.

Example 14

CMV-Infected HUVECs Dysregulate ALK1 and ALK5 Protein Levels

Figure 21:
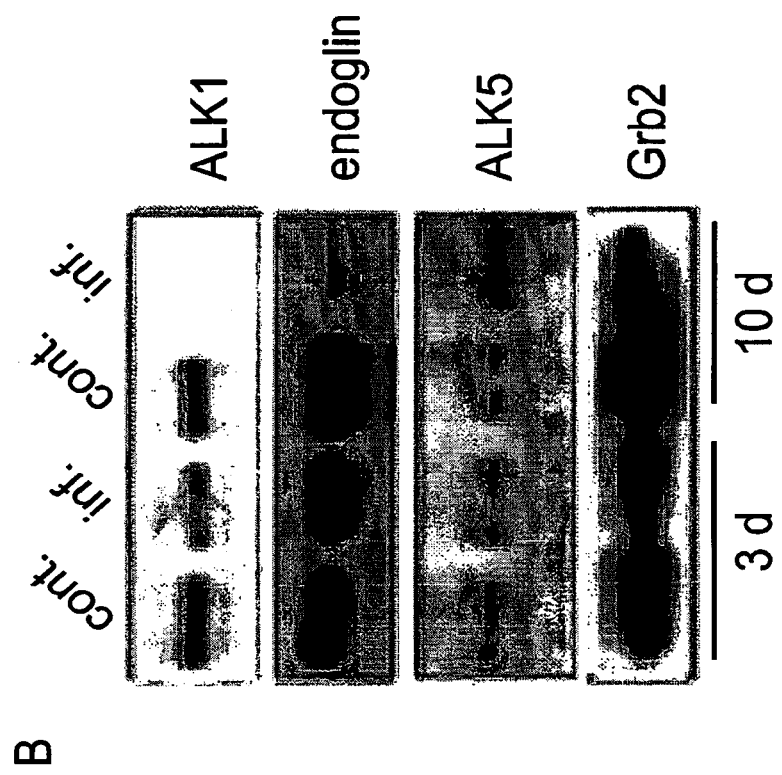
FIG. 21: CMV-infected HUVECs increase expression of ALK5 and reduce ALK1. A: Surface expression of ALK1, endoglin, and ALK5 was analyzed by flow cytometric analysis at 7 days after infection in the absence or presence of viral DNA polymerase inhibitors. Typical histograms from control (cont.) and infected (inf.) HUVECs are shown. Shaded areas represent expression of specific proteins. Lines represent isotype control. Numbers represent mean fluorescence intensity. The experiments were repeated at least four times. B: Cell lysates from control (cont.) or infected (inf.) HUVECs at 3 and 10 days after infection were fractionated by 10% SDS-PAGE and blotted on nitrocellulose. Filters were incubated with antibodies to ALK1, endoglin, ALK5, and Grb2 (loading control). C: Surface expression of ALK1, endoglin, and ALK5 was analyzed by flow cytometric analysis at 7 days of culture with conditioned medium (CM) from infected HUVECs. Relative surface expression as expressed by mean fluorescence intensity was normalized for control HUVECs in the same experiment. Results are the mean (±SE) from three to seven experiments. Asterisks indicate relative expression level of receptors in HUVECs cultured with conditioned medium as compared with controls (*P<0.05, **P<0.01).
Figure 21:
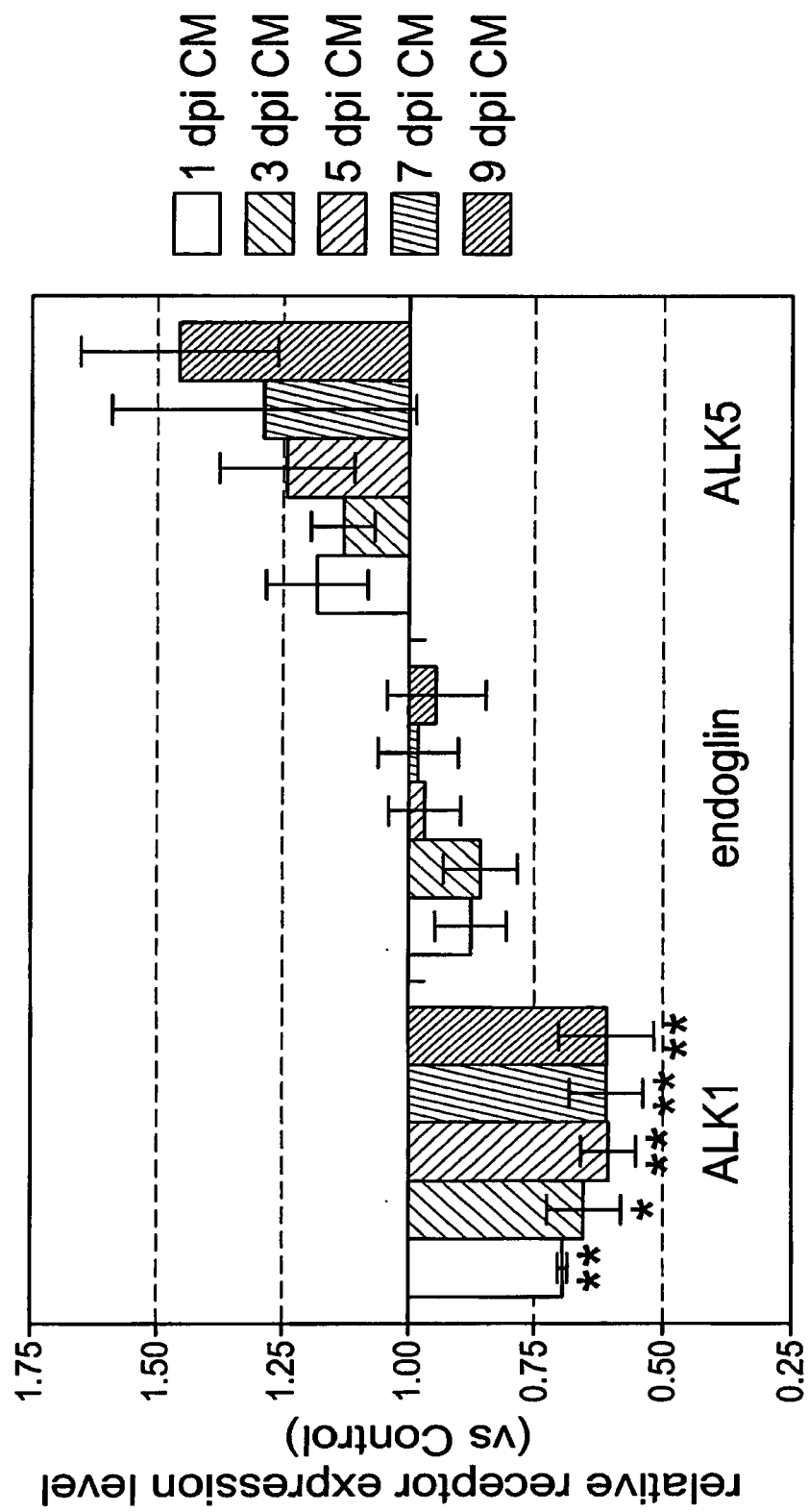

Endothelial cells express ALK1, which stimulates Smad1/5 phosphorylation during angiogenesis and counterbalances TGF-β1/ALK5 signaling (Oh et al., *Proc Natl Acad Sci USA*, 97:2626-2631 (2000); Lebrin et al., *EMBO J* 2004, 23:4018-4028). The ALK1 signaling pathway involves an accessory receptor, endoglin, which is highly expressed in endothelial cells, and indirectly inhibits TGF-β1/ALK5 signaling. Preferential phosphorylation of Smad3 in CMV-infected HUVECs suggested that the ratio of ALK1 and ALK5 receptors on the cell surface might be altered. By flow cytometry, the present example demonstrates that uninfected HUVECs expressed ALK1, endoglin, and ALK5 (FIG. 21A). Intensities of both ALK1 and ALK5 changed appreciably in infected HUVECs at late time points, with a significant decrease in ALK1 and endoglin expression and a significant increase in ALK5 expression as compared with uninfected cells (FIG. 21A, Table 3). Immunoblot analysis revealed the same pattern of changes in expression levels (FIG. 21B). Interestingly, the shift in receptor expression occurred even when cells were treated with anti-integrin αvβ6, anti-TGF-β neutralizing antibody, or the ALK5 kinase inhibitor, indicating that this change was independent of αvβ6-mediated TGF-β1 activation. Subsequently, the possibility that soluble factors mediate the observed changes in the expression of ALK1, endoglin, and ALK5, was investigated. After day 1, conditioned medium from infected cells was collected on alternate days and frozen. HUVECs were cultured with the filtered conditioned medium for 8 days, and the surface expression of the receptors was analyzed by flow cytometry. Expression of ALK1 was decreased in cells cultured with conditioned medium from all time points. Expression of ALK5 increased in cells cultured with the conditioned medium from 5, 7, and 9 days after infection. Expression of endoglin was not much affected by conditioned medium from any time point (FIG. 21C).

effect on uninfected control cells (FIG. 22E). Furthermore, the ALK5 kinase inhibitor SB431542 had an inhibitory effect on surface expression of type IV collagen in infected cells in

TABLE 3

|  | ALK1 | | Endoglin | | ALK5 | |
| --- | --- | --- | --- | --- | --- | --- |
|  | Control | Infected | Control | Infected | Control | Infected |
| HMVEC-L | 84.6 ± 21.6 | 14.9 ± 13.9* | 2399.0 ± 376.3 | 1190.7 ± 137.8† | 23.7 ± 9.4 | 180.5 ± 83.1* |
| UtMVECs | 516.9 ± 76.1 | 297.0 ± 61.5* | 4640.9 ± 465.0 | 2564.3 ± 523.2† | 216.4 ± 56.3 | 338.9 ± 90.8 |
| HUVECs | 138.8 ± 20.0 | 49.2 ± 9.2‡ | 2479.9 ± 355.2 | 426.8 ± 87.2‡ | 81.8 ± 23.7 | 547.0 ± 107.5‡ |

Surface expression of ALK1, endoglin, and ALK5 was analyzed by flow cytometry late in infection. Numbers represent mean fluorescence intensity (MFI) (mean ± SE) of 3 to 11 experiments. Asterisks and symbols indicate significantly changed MFI in infected cells compared with uninfected control cells (*P < 0.05; †P < 0.01; ‡P < 0.001). HMVEC-L: ALK1 (n = 3), endoglin (n ◆ 5), ALK5 (n = 4); UtMVECs: ALK1 (n = 3), endoglin (n = 5), ALK5 (n = 6); HUVECs: ALK1 (n = 10), endoglin (n = 5), ALK5 (n = 11).

Finally, viral polymerase inhibitors were able to partially block the change in ALK1 and ALK5 expression (FIG. 21A), suggesting that a part of those changes may be mediated through immediate-early or early genes. In contrast, expression of endoglin was not changed by infection while in the presence of a viral DNA polymerase inhibitor (FIG. 21A), indicating that viral replication is required for change in endoglin expression. Together, these results indicate that there are both direct effects of viral infection on receptor expression and indirect effects that depend on secreted molecules. These results confirmed that CMV-infected HUVECs reduce ALK1 and endoglin expression, whereas they increase ALK5 expression. Increased availability of ALK5 for TGF-β1 binding, in conjunction with reduced levels of ALK1 and endoglin in infected HUVECs, could explain preferential Smad3 phosphorylation and possible downstream signaling events.

Example 15

Figure 22:
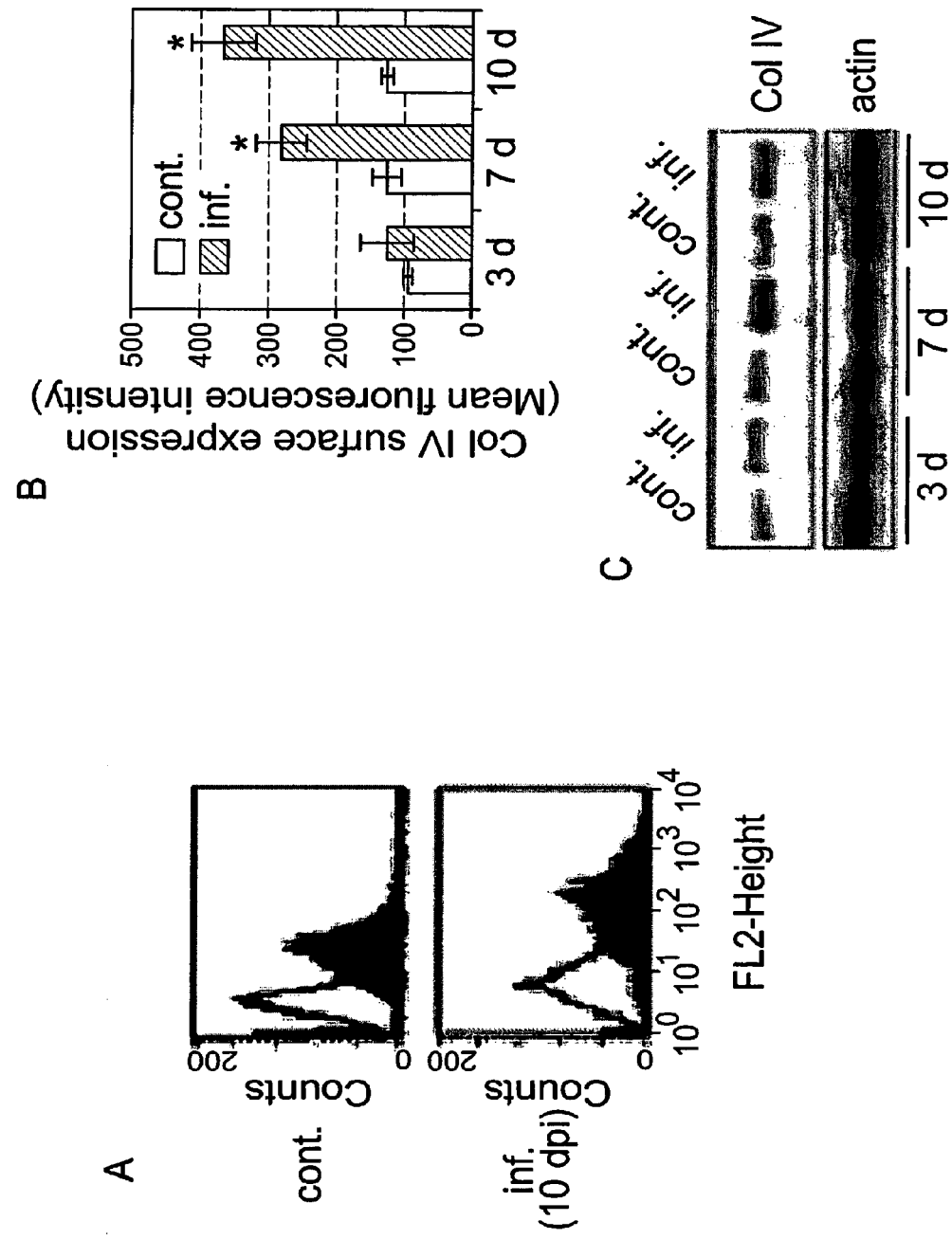
FIG. 22: Increased type IV collagen synthesis by CMV infection was blocked by anti-TGF-β and anti-αvβ6 neutralizing antibodies. A: Surface expression of type IV collagen was analyzed by flow cytometric analysis at 10 days after infection. Typical histograms from control (cont.) and infected (inf.) HUVECs are shown. Shaded areas represent expression of specific proteins. Lines represent isotype control. B: The results represent the mean fluorescence intensity of type IV collagen (mean±SE) from three to seven experiments. Asterisks indicate surface expression in infected HUVECs as compared with uninfected controls (*P<0.01). C: Cell lysates from control (cont.) or infected (inf.) HUVECs at 3, 7, and 10 days after infection were fractionated by 8% SDS-PAGE and blotted on nitrocellulose. Filters were incubated with anti-type IV collagen (Col IV) and anti-actin (loading control) antibodies. D: Surface expression of type IV collagen was analyzed by flow cytometric analysis at 7 days without antibody (untreated) or with anti-TGF-β neutralizing antibody (1D11), function-blocking anti-αvβ6 antibody (3G9), or mouse IgG1 isotype control antibody (control Ab). Relative surface expression as expressed by mean fluorescence intensity was normalized for control HUVECs in the same experiment. Results are the mean (±SE) from three experiments. Treatment with neutralizing antibodies significantly decreased surface expression of type IV collagen compared with infected cells (*P<0.01). E: Effects of anti-TGF-β antibody and anti-αvβ6 antibody on type IV collagen production. Control and infected HUVECs were cultured without antibody (untreated) or with anti-TGF-β neutralizing antibody (1D11, 40 µg/ml), function-blocking anti-αvβ6 antibody (3G9, 40 µg/ml), or mouse IgG1 isotype control antibody (control Ab, 40 µg/ml) for 7 days. Lysates were fractionated by 8% SDS-PAGE and blotted. Filters were incubated with specific antibodies. Results are representative of at least four independent experiments.
Figure 22:
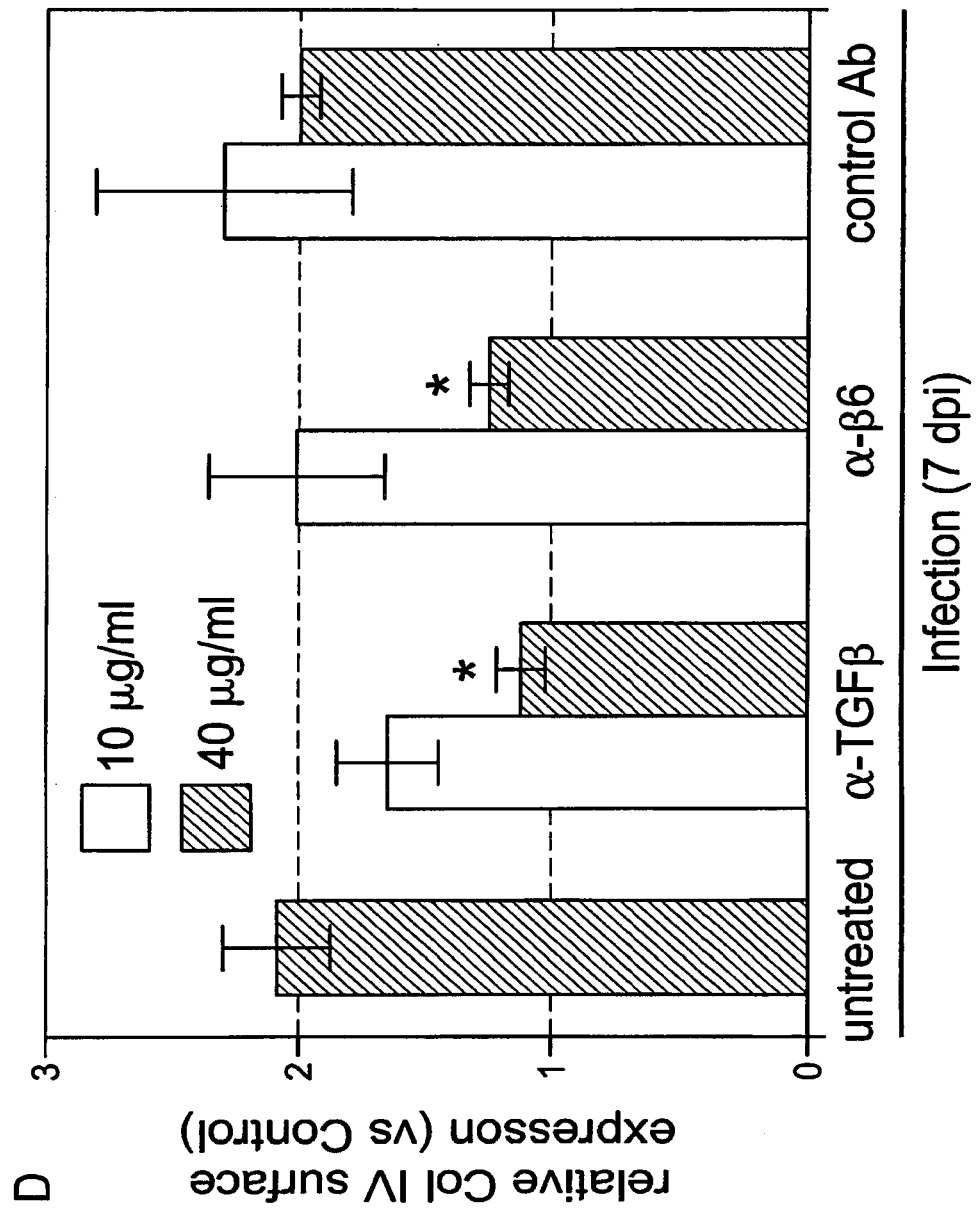
Figure 22:
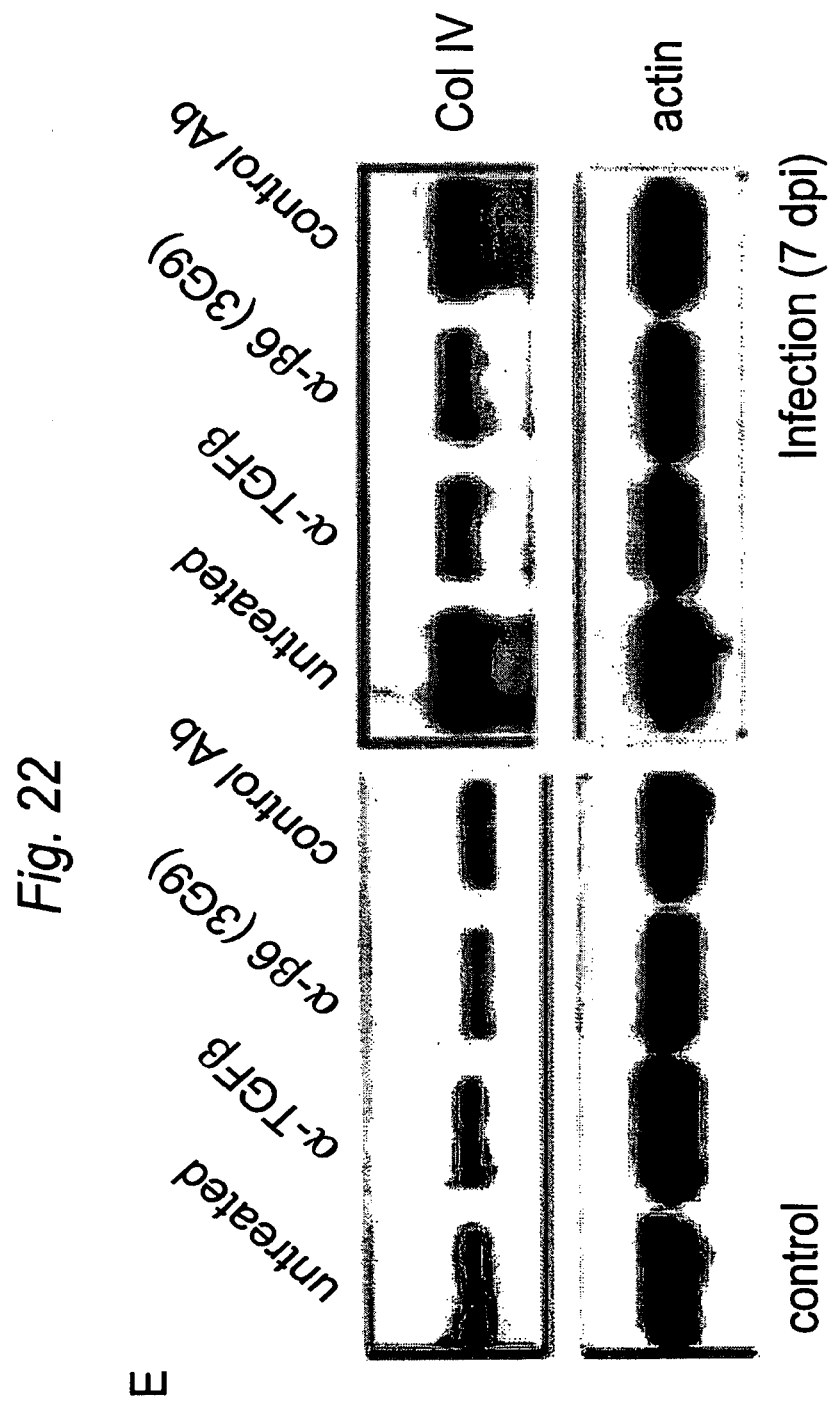

Integrin αvβ6-Mediated TGF-β Activation Increases ECM Production in CMV-Infected Cell Cultures TGF-β1 is a potent fibrotic factor responsible for the synthesis of ECM, and profibrotic TGF-β1 responses are induced primarily via ALK5/Smad3 signal transduction in normal fibroblasts (Ishida et al., *J Invest Dermatol*, 126:1733-1744 (2006)). TGF-β1 also potently promotes the synthesis and deposition of ECM in endothelial cells (Pepper, M. S., *Cytokine Growth Factor Rev*, 8:21-43 (1997)). In microarray analysis, HUVECs infected with recombinant adenovirus carrying a constitutively active form of ALK5 up-regulate ECM genes, whereas ALK1 either does not exhibit a significant effect or causes down-regulation of these genes (Ota et al., *J Cell Physiol*, 193:299-318 (2002)). Therefore, it was investigated in the present example whether CMV-activated TGF-β1 could increase ECM production and whether blocking TGF-β3 activation could prevent the effect. Surface expression of type IV collagen, analyzed by flow cytometry, was significantly increased in infected HUVECs at late time points (FIG. 22, A and B). Immunoblot analysis also showed an increased production of type IV collagen in infected cells (FIG. 22C). To evaluate the effect of inhibition of activation of TGF-β1 on CMV-induced profibrotic response, infected cells were treated with anti-TGF-β (1D11) and anti-αvβ6 (3G9) antibodies for 7 days. The results showed that these neutralizing antibodies prevented CMV-induced elevation of type IV collagen expression and that 40 µg/ml of either antibody almost completely abolished the effect (FIG. 22D). Immunoblot analysis revealed that neutralizing antibodies reduced the production of type IV collagen in infected cells and had no effect on uninfected control cells (FIG. 22E). Furthermore, the ALK5 kinase inhibitor SB431542 had an inhibitory effect on surface expression of type IV collagen in infected cells in a dose-dependent manner. A similar effect was seen in control cells, indicating that the ALK5 kinase inhibitor blocked the basal level of TGF-β more efficiently than blocking antibodies and had a greater effect on inhibition of type IV collagen synthesis. In addition, surface expression of fibronectin was increased at late times after infection, and was reduced by the ALK5 kinase inhibitor. Taken together, these results indicate that ECM production is increased by integrin αvβ6-mediated TGF-β1 activation in infected HUVECs.

Example 16

Figure 23:
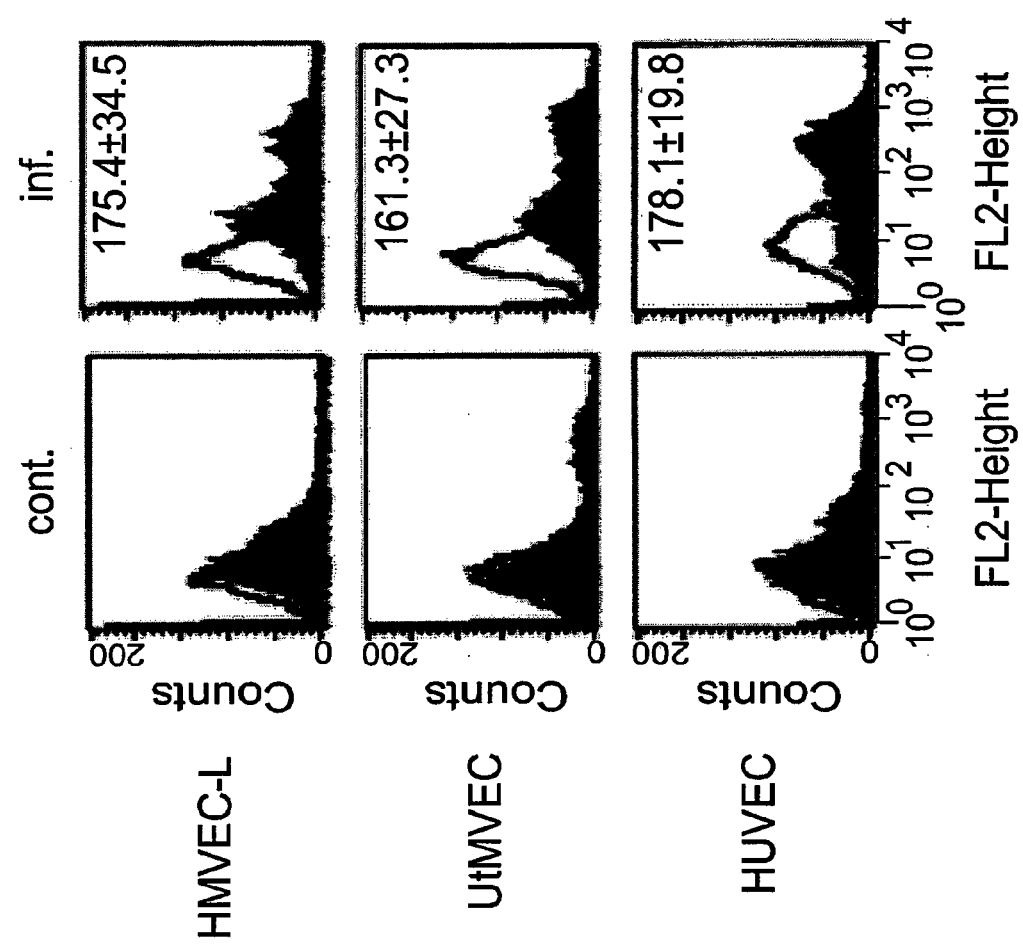
FIG. 23: Different CMV-infected endothelial cell types induce different levels of integrin αvβ6. Flow cytometric analysis of integrin αvβ6 in HMVEC-L, UtMVECs, and HUVECs at 10 days after infection with VR1814. Typical histograms from control (cont.) and infected (inf.) cells are shown. Shaded areas represent expression of specific proteins. Lines represent isotype control. Numbers represent mean fluorescence intensity (mean±SE). The experiments were repeated at least three times.

CMV-Infected Microvascular Endothelial Cell Types Induce Integrin αvβ6 and Switch TGF-β Receptor Expression To determine whether CMV infection altered integrin αvβ6 expression in other endothelial cell types, VR1814-infected HMVEC-L and UtMVECs were analyzed for surface expression of integrin αvβ6 at 10 days after infection and compared it with surface expression in infected HUVECs. Integrin αvβ6 was induced in both microvascular endothelial cell types after infection (FIG. 23). Interestingly, integrin αvβ6 was present in uninfected UtMVECs, but the induction level at late times after infection was not different from that of infected HUVECs. In addition, we compared the levels of the repertoire of TGF-β receptors expressed by HUVEC-L and UtMVECs (Table 3). All endothelial cells expressed high levels of ALK1 and endoglin and lower levels of ALK5. After infection, ALK1 and endoglin expression were significantly decreased, and ALK5 was significantly increased, as was observed in infected HUVECs. Interestingly, levels of TGF-β receptor expression on the surface of infected cells differed according to the vascular beds from which the endothelial cells were obtained.

Example 17

Up-Regulated Integrin αvβ6 in Blood Vessels of CMV-Infected Organs

Figure 24:
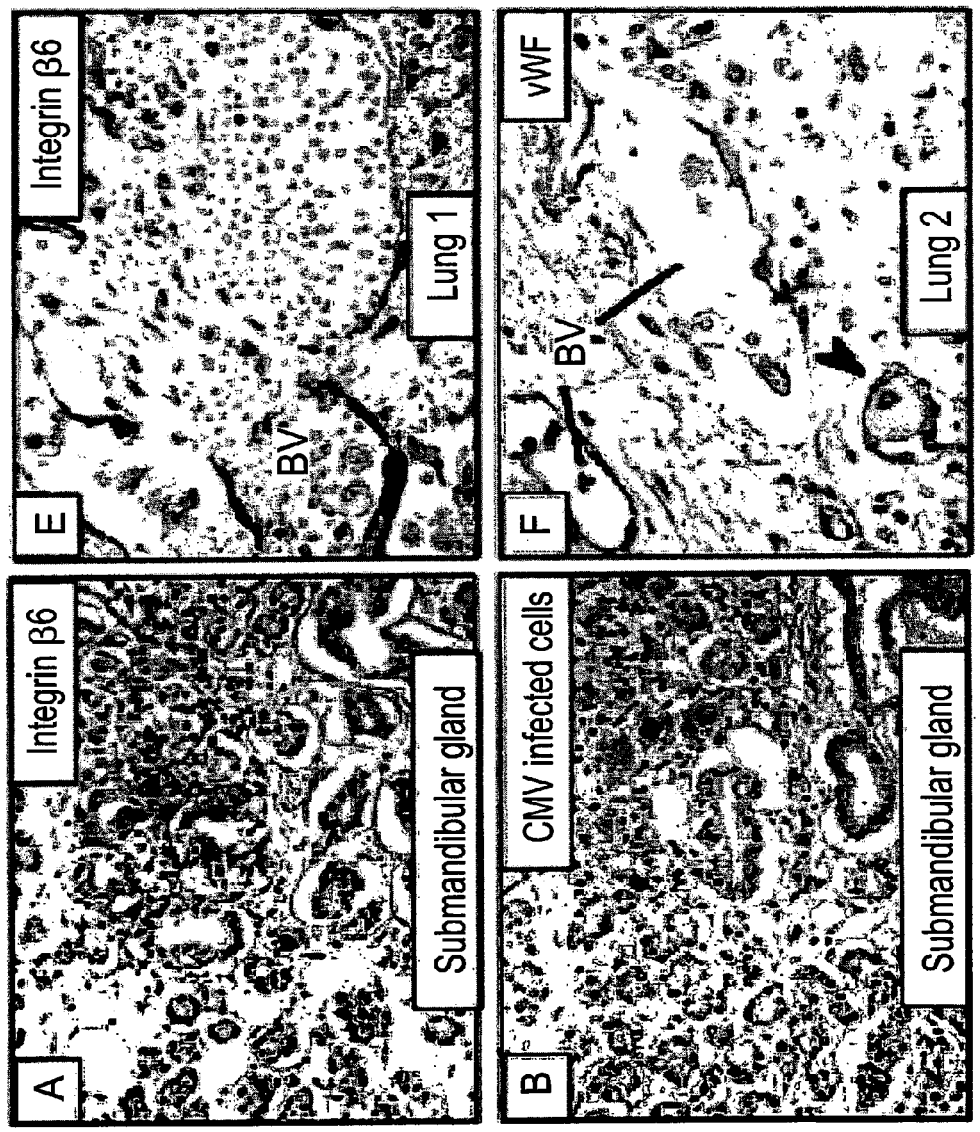
FIG. 24: CMV-infected tissues induce integrin αvβ6 expression in epithelium and vascular endothelium in vivo. Samples (1 submandibular gland and 11 lung) obtained from 12 patients with CMV infection with histological evidence of nuclear inclusion bodies were evaluated for integrin β6 expression A-D: Integrin αvβ6 immunostaining in CMV-infected cells and gland epithelium in submandibular gland. A and B: Serial sections of infected submandibular gland immunostained with antibodies to integrin αvβ6 (A) and CMV replication proteins in infected cells (B). C and D: Integrin αvβ6 was strongly up-regulated in epithelial cells of submandibular glands proximal to cytomegalic cells (foci of viral replication). E: Integrin αvβ6 immunostaining in vascular endothelium of CMV-infected lung. Expression of integrin αvβ6 in blood vessels was found in two samples. F-H: Serial sections of infected lung immunostained with antibodies to von Willebrand factor (vWF) (F), CMV replication proteins in infected cells (G), and integrin αvβ6 induction (H). Black arrowheads, integrin αvβ6-positive cytomegalic cells; white arrowheads, glandular epithelium; black arrows, integrin αvβ6-positive endothelial cells. BV, blood vessels. Original magnifications: 20× (A, B); 40× (C—H).
Figure 24:
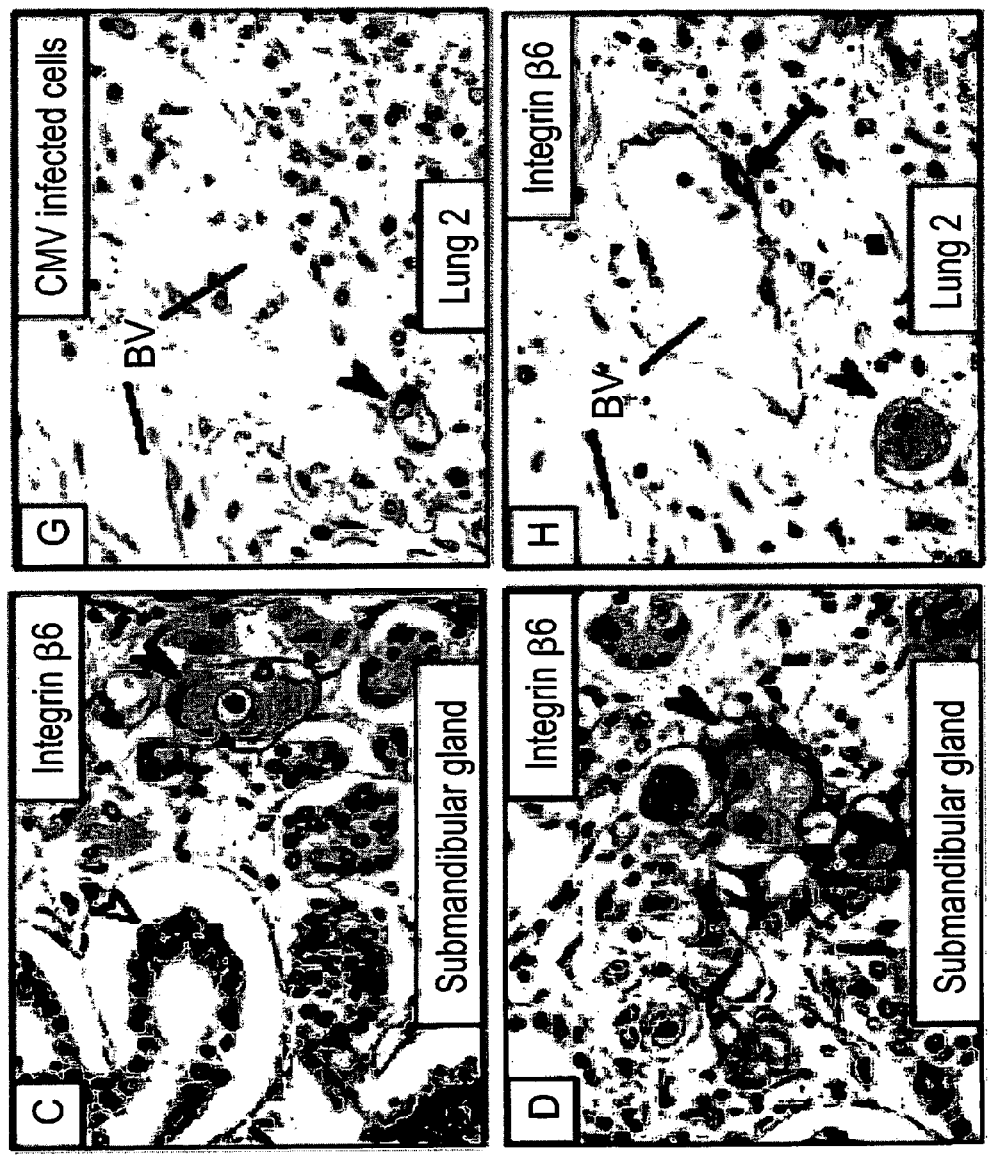

Having found that the pathogenic CMV strain VR1814 induces integrin αvβ6, which initiates TGF-β1/ALK5 signaling in infected endothelial cells in vitro, specimens from salivary gland, lung, uterus, and placenta with natural infection were inspected to ascertain whether expression occurs in vivo. Immunohistochemical analysis was performed on tissues with confirmed histological evidence of cytomegalic cells (ie, sites of viral replication and active infection). In submandibular glands, islands of integrin αvβ6-positive cells were detected among much larger areas of nonexpressing cells (FIG. 24, A, C, and D). Expression of integrin αvβ6 was found in infected cytomegalic cells (owl's eye appearance) (FIG. 24, B and C) and was up-regulated in nearby epithelium (FIG. 24D). In infected lungs, strong integrin αvβ6 induction was seen in endothelial cells (FIG. 24E). However, induction was infrequent (2 of 11 lung samples), and only focal expression of integrin αvβ6 was found. Analysis of serial sections from infected lungs showed a vascular staining pattern for von Willebrand factor (FIG. 24F) proximal to infected endothelial cells (FIG. 24G) that induced integrin αvβ36 expression (FIG. 24H). Interestingly, integrin αvβ6-specific antibodies showed that the protein was present in blood vessels immediately adjacent to CMV-infected cells, but no staining was observed in distal capillaries (FIG. 24F).

Figure 25:
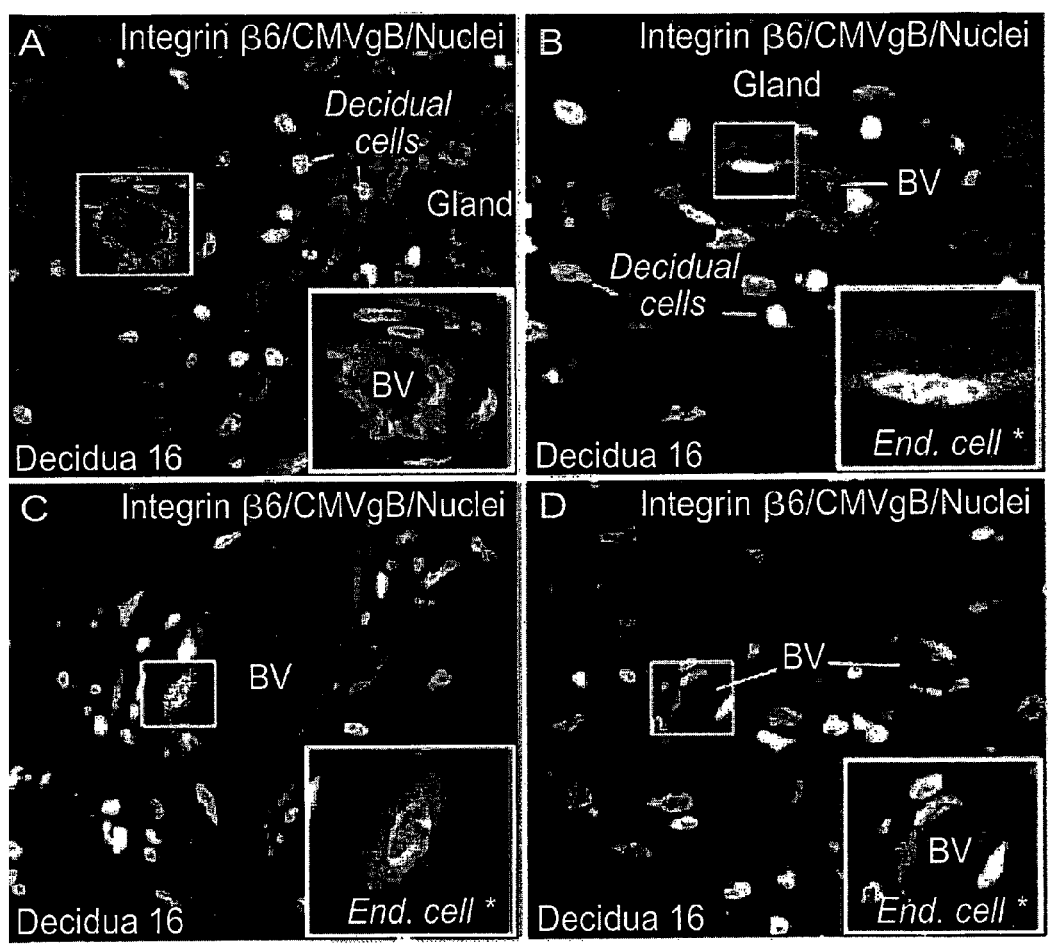
FIG. 25: Integrin αvβ6 induction in blood vessels of CMV-infected decidua in early gestation. A: Immunostaining of integrin αvβ6 expression (green) in infected blood vessel (BV) proximal to infected decidual cells immunostained for CMV glycoprotein B (gB) (red). B: Integrin αvβ6 expression (green) in blood vessel proximal to infected glandular epithelium (red). C: Integrin αvβ6 expressed in blood vessel of the same tissue (decidua 16) in an area without viral proteins. D: Integrin αvβ6-negative BV. Expression of integrin αvβ6 was found in two of three decidual biopsy specimens. Original magnifications, 400×.
Figure 26:
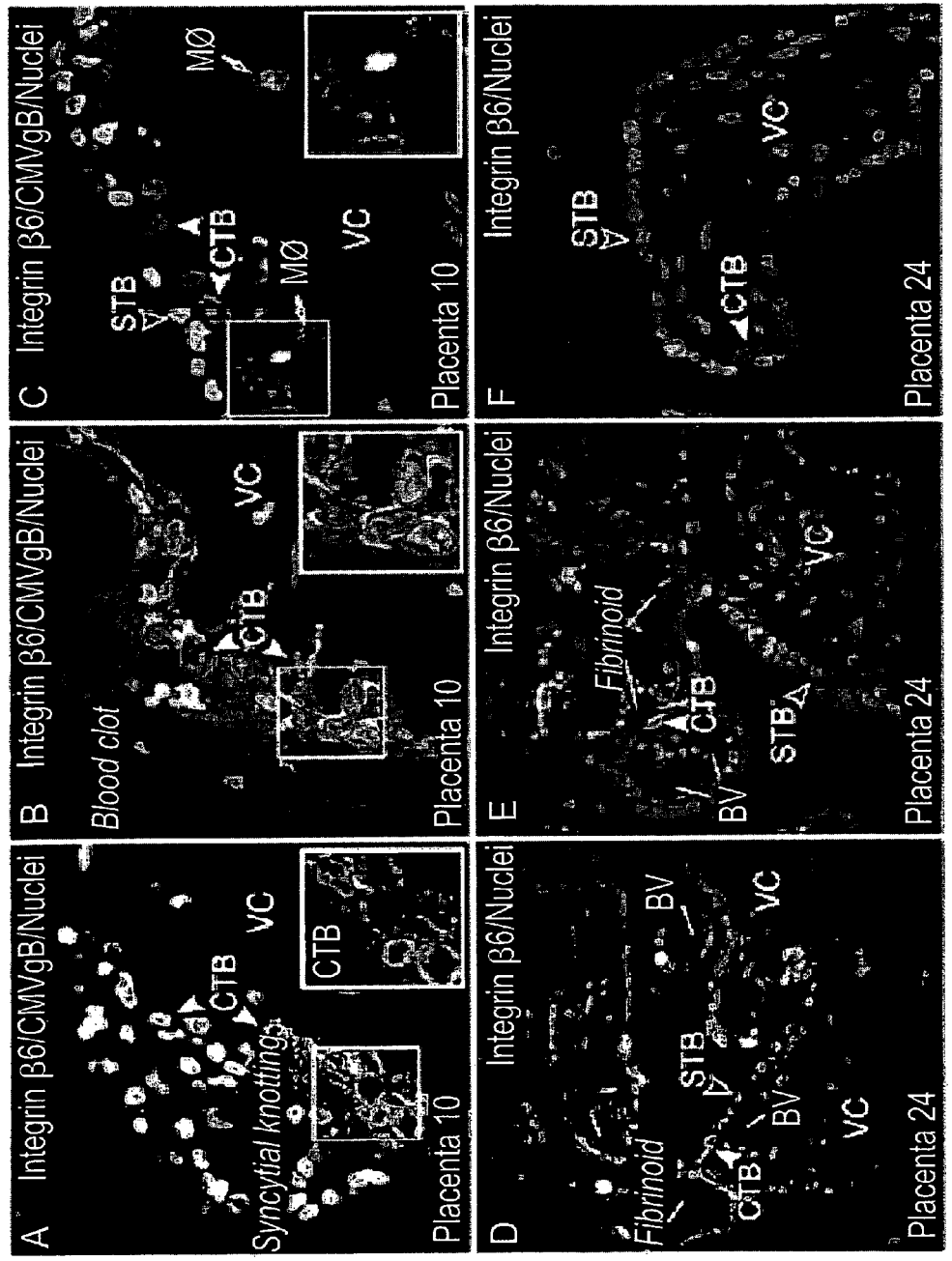
FIG. 26: Up-regulated integrin αvβ6 expression in villus cytotrophoblast progenitor cells, epithelial cells of the placenta. A-C: CMV-infected early gestation placenta. D-F: Uninfected placenta at term. Cytotrophoblasts broadly induced integrin αvβ6 (green) proximal to sites of damage, syncytial knotting (A), and adherent blood clots (B), but not in healthy chorionic villi with macrophage (Mφ) uptake of CMV virion gB proteins (C) of the same tissue (placenta 10). Expression of integrin αvβ6 in cytotrophoblasts was found in two of three placental biopsy specimens. D and E: Cytotrophoblasts contiguous with fibrinotic deposits (ECM accumulation) on the villous surface strongly up-regulate integrin αvβ6 (green). F: Integrin αvβ6-negative villus in healthy villus in the same tissue (placenta 24). Similar patterns were found in five of eight term placenta. CTB, cytotrophoblast; STB, syncytiotrophoblast; VC, villus core; BV, blood vessel. Original magnifications, 400×.

Previously, it was reported that CMV replicates at the uterine-placental interface, transmitting virus from infected capillaries to decidual cells and cytotrophoblast progenitor cells of epithelial origin in the adjacent placenta (Pereira et al., *J Virol*, 77:13301-13314 (2003); McDonagh et al., *J Infect Dis*, 190:826-834 (2004)). In the present example, it was found that infected UtMVECs induce integrin αvβ36 expression, suggesting that the same induction could occur in utero. Three paired decidual and adjacent placental biopsy specimens naturally infected with CMV in early gestation, and eight placentas from healthy deliveries at term were then examined. In the decidua, immunostaining for CMV virion gB revealed areas with infected decidual cells (FIG. 25A). Nearby, an infected capillary showed up-regulated integrin αvβ6 expression in an overall diffuse staining pattern (FIG. 25A). When glandular epithelia were infected, integrin αvβ6 was induced in proximal blood vessels (FIG. 25B). At times, marked expression was found in endothelial cells without evidence of viral proteins in surrounding tissue (FIG. 25C). Occasionally, endothelial cells were infected, but capillaries showed little or no integrin αvβ6 staining (FIG. 25D). In the placenta, immunostaining revealed clusters of cytotrophoblast progenitor cells with intense membrane expression of integrin αvβ6 in chorionic villi, where syncytiotrophoblasts had signs of local damage (FIG. 26). For example, intense surface membrane staining was found on cytotrophoblast progenitors underneath syncytial knotting (FIG. 26A) and in the vicinity of blood clots adhering to villi in contact with maternal blood (FIG. 26B). Occasional cytotrophoblasts contained scattered cytoplasmic vesicles with CMV gB, a pattern suggesting virion uptake in caveolar vesicles without replication (Maidji et al., *Am J Pathol*, 168:1210-1226 (2006); Maidji et al, *J Virol*, 81:4701-4712 (2007)). In contrast, integrin αvβ6 was not expressed by cytotrophoblasts when CMV virion gB accumulated in villus core macrophages, and syncytiotrophoblasts were undamaged (FIG. 26C). Similar patterns of expression were seen in the other placenta.

Immunostaining of a placenta at term (five of eight) revealed high integrin αvβ6 induction in cytotrophoblast progenitor cells located next to fibrinoids, which are large ECM deposits formed on the surface of chorionic villi in contact with maternal blood (FIG. 26, D and E). In areas with undamaged chorionic villi, cytotrophoblasts showed little or no detectable integrin αvβ6 expression (FIG. 26F). Together these results confirm and extend our in vitro findings and show that integrin αvβ6 is up-regulated in diverse infected tissues. However, not all endothelial cells adjacent to the infected cells expressed integrin αvβ6, suggesting a requirement for additional cellular factors or a special environment.

In the present examples, it is shown that CMV-infected endothelial cells express epithelial integrin αvβ6 in vitro (FIGS. 17 and 23) and in vivo (FIGS. 24 and 25), switch expression levels of TGF-β receptors (FIG. 21, Table 3), and down-regulate endothelial-specific proteins, including VE-cadherin, von Willebrand factor, and PECAM-1. Taken together, these results suggest that CMV-infected endothelial cells undergo a phenotypic change to a nonendothelial cell type, a transition that could be associated with CMV pathogenesis.

In pregnancies affected by congenital CMV infection, substantial evidence of virus-initiated pathology is provided by inflammation, leukocytic infiltration, edema, and fibrinotic deposits that occlude blood vessels in the villus core (Garcia et al., *Placenta*, 10:1-18 (1989); Benirschke, K., Kaufmann, P., *Pathology of the Human Placenta*, New York, Springer (2000)). Except in cases of severe symptomatic CMV disease, evidence of ongoing viral replication in the placenta is seldom detected. Here it is shown in the present examples that integrin αvβ6 is up-regulated in blood vessels in early gestation decidua with focal sites of viral replication and in villus cytotrophoblasts in placentas containing viral DNA (FIGS. 25 and 26). Remarkably strong induction was observed in cytotrophoblasts near blood clots adhering to damaged chorionic villi and in cells contiguous with fibrinoids composed of fibronectin, laminin, and collagen IV, suggesting that integrin-mediated TGF-β1 activation contributes to pathology in the uterine and fetal compartment. Purified villus cytotrophoblasts isolated from placentas at term that contain CMV DNA, and virion proteins without active replication express integrin αvβ6 that activates TGF-β1 (Tabata et al., *Placenta*, 28:527-537 (2007)). Deposition of ECM protein by integrin P-mediated activation of TGF-β1 (FIG. 22), impairment of ECM degradation by down-regulation of matrix metalloproteinase 2 activity by CMV-encoded viral interleukin-10 (Yamamoto-Tabata et al., *J Virol*, 78:2831-2840 (2004)), and increased production of the tissue inhibitor of metalloproteinases 1, which is independent of TGF-β1 activation, could explain the marked pathology at the uterine-placental interface in congenital infection.

Example 18

Evaluation of Maternal Immunity to CMV, Passive Antibody in Fetal Circulation, Viral Replication in the Placenta and Selected Biomarkers of Congenital Infection In the present example, placentas and sera were examined from uncomplicated deliveries. Maternal and Fetal CMV Immune Status: Immunity to CMV was evaluated by quantifying virus-specific IgG and neutralizing functions in maternal and fetal circulation in 40 paired samples of placental and cord blood sera (obtained at delivery). The avidity of CMV-specific antibodies was determined using ELISA (Radim, Rome, Italy). Cases of very early primary CMV infection were identified by immunofluorescence assays of virus-specific IgG to CMV-infected coils. Plaque-reduction assays were performed to quantify neutralizing functions of CMV-specific IgG in maternal and fetal sera. CMV glycoprotein B-specific IgG was quantified using a specialized ELISA in a collaboration with Sanofi. IgG1 levels in maternal and fetal circulation were quantified (Human IgG1 subclass profile ELISA, Zymed Laboratories). Late primary CMV infection was distinguished from recurrent infection by IgG immunoblot profiles against recombinant viral proteins (recomBlot, Mikrogen, Germany).

Placental Infection: CMV replication in the placenta, gB genotype analysis and quantification of soluble endoglin (sEng), a potential cellular biomarker was quantified in maternal circulation. Results of serological analysis and assays for CMV infection in placentas are summarized (Table 4).

TABLE 4

Humoral CMV Immune Status in Maternal and Fetal Blood Samples from Placentas at Delivery

| Placenta number | Avidity (%) | Avidity result | CMV IFA | Neut | gB ELISA | IgG1 (mg/ml) | RecomBlot CMV protein profile | Placental Infection Placenta PCR | CMV gB Genotype | sEndoglin sEng (ng/ml) |
|---|---|---|---|---|---|---|---|---|---|---|
| UCSF #1 | 10 | Low | +++ | Neg | 3287 | | IE1$^{low}$, gB1$^{low}$, gB2$^{low}$ | 5/5 | type 3 | 447 |
| 92 | Neg | Neg | | | <15 | 2988 | Neg | 4/5 | type 3 | 47 |
| 92 cord | Neg | Neg | | | <15 | 3100 | Neg | | | 3 |
| 103 | Neg | Neg | +++ | | <15 | 2738 | Neg | 2/5 | | 3 |
| 103 Cord | Neg | Neg | +++ | | <15 | 6313 | | | | 2 |
| 104 | 71.7 | High | +++ | | 1252 | 5000 | IE1$^{low}$, P150, gB1, gB2 | 2/5 | type 2, 3 | 30 |
| 104 Cord | 67.7 | High | +++ | | 1545* | 10125 | IE1$^{low}$, P150, gB1, gB2 | | | 2 |
| 105 | Neg | Neg | +++ | | <15 | 3325 | Neg | 2/5 | type 3 | 9 |
| 105 Cord | Neg | Neg | +++ | | <15 | 9075 | Neg | | | 2 |
| 106 | 49.5 | High | +++ | | 855 | 4000 | P150, gB1, gB2 | Neg | | 182 |
| 106 Cord | 46.8 | High | +++ | | 1762* | 9375 | P150, gB1, gB2 | | | 2 |
| 107 | 53.5 | High | ++ | | 818 | 4250 | IE1$^{low}$, P150, CM2, P65, gB1$^{low}$ | 2/5 | type 3 | 28 |
| 107 Cord | 67.2 | High | ++ | | 2534* | 6500 | IE1$^{low}$, P150, CM2, P65, gB1$^{low}$ | | | 2 |
| 108 | Neg | Neg | ++ | | <15 | | Neg | 2/5 | | |
| 108 Cord | Neg | Neg | ++ | | <15 | | Neg | | | |
| 113 | | High | | | 2134 | | | 5/5 | | |
| 113 Cord | | | | | 2046 | | | | | |
| 117 | 52 | High | +++ | 1:8 | 926 | 4825 | P150, gB1, gB2$^{low}$ | 1/5 | type 3 | |
| 117 Cord | 70.8 | High | +++ | 1:16 | 2208* | 8500 | P150, gB1, gB2$^{low}$ | | | |
| 120 | 56 | High | +++ | 1:64 | 2352 | 1250 | P150, gB1, gB2 | Neg | | |
| 120 Cord | 59.8 | High | +++ | 1:64 | 4155* | 3950 | P150, IE1, gB1, gB2 | | | |
| 121 | Neg | Neg | +++ | | <15 | 2950 | Neg | Neg | | |
| 121 Cord | 2.2 | Low | +++ | | <15 | 6250 | | | | |
| 122 | Neg | Neg | +++ | | <15 | 1800 | Neg | 3/5 | | ~42.3 |
| 122 Cord | Neg | Neg | +++ | | <15 | 2625 | | | | 2 |
| 123 | 49 | High | +++ | 1:16 | 444 | 2625 | P150, gB1, gB2 | 1/5 | | |
| 123 Cord | 55 | High | +++ | 1:16 | 609* | 7750 | P150, gB1, gB2 | | | |
| 124 | 55.5 | High | +++ | 1:16 | 1986 | | P150, CM2$^{low}$, gB1$^{low}$, gB2$^{low}$ | 2/5 | type 3 | |
| 124 Cord | 44 | Mean | +++ | 1:16 | 2690* | | P150, CM2$^{low}$, gB1$^{low}$, gB2$^{low}$ | | | |
| 125 | 64.3 | High | +++ | 1:64 | 871 | 2500 | P150, IE1$^{low}$, gB1 | 3/5 | type 3 | |
| 125 Cord | 66.9 | High | +++ | 1:64 | 2625* | 9750 | P150, IE1$^{low}$, gB1 | | | |
| 126 | Neg | Neg | +++ | | <15 | 3675 | Neg | Neg | | 227 |
| 126 Cord | Neg | Neg | +++ | | <15 | 14500 | Neg | | | 2 |
| 127 | 66.5 | High | +++ | 1:32 | 1067 | 2875 | P150, CM2$^{low}$ | 3/5 | type 3 | 238 |
| 127 Cord | 69.7 | High | +++ | 1:32 | 2414* | 9500 | IE1, P150, CM2, P65, gB1 | | | 2 |
| 128 | Neg | Neg | +++ | | <15 | 2250 | Negative | 2/5 | type 2, 3 | 223 |
| 128 Cord | Neg | Neg | +++ | | <15 | 4875 | Negative | | | 2.4 |
| 129 | 54.9 | High | | 1:32 | 1278 | | IE1, P150, CM2, gB1, P65$^{low}$, gB2 | Neg | | 195 |
| 129 Cord | 57.4 | High | | 1:32 | 1585* | | IE1, P150, CM2, gB1, P65$^{low}$, gB2 | | | 2 |
| 130 | 68 | High | ++ | 1:64 | 9712 | 5213 | IE1$^{low}$, P150, CM2, P65, gB1, gB2 | Neg | | 147 |
| 130 Cord | 67 | High | ++ | 1:64 | 18195* | 7125 | IE1$^{low}$, P150, CM2, P65, gB1, gB2 | | | 1.9 |
| 131 | 69.3 | High | +++ | 1:16 | 1632 | 2338 | P150, CM2$^{low}$, gB1 | Neg | | |
| 131 Cord | 83.4 | High | +++ | 1:16 | 3298* | 3538 | P150, CM2$^{low}$, gB1 | | | |
| 132 | Neg | Neg | +++ | | | 1925 | | Neg | | 80 |
| 132 Cord | Neg | Neg | +++ | | | 5700 | | | | 3 |
| 133 | 50 | High | +++ | 1:32 | | 3875 | P150, gB1, gB2 | Neg | | 79 |
| 133 Cord | 52 | High | +++ | 1:32 | | 5375 | P150, gB1, gB2 | | | 2 |
| 134 | Neg | Neg | ++ | | | 2925 | | Neg | | |
| 134 Cord | Neg | Neg | ++ | | | 7875 | | | | |
| 135 | 49.6 | High | +++ | 1:32 | | | P150, P65$^{low}$, gB1$^{low}$, gB2$^{low}$ | Neg | | |
| 135 Cord | 71.3 | High | +++ | 1:32 | | | P150, P65$^{low}$, gB1$^{low}$, gB2$^{low}$ | | | |
| 136 | Neg | Neg | ++ | | | 5125 | | 1/5 | | 70 |
| 136 Cord | Neg | Neg | ++ | | | 8375 | | | | 2 |
| 137 | Neg | Neg | +++ | | | 6750 | | 2/5 | | 101 |
| 137 Cord | Neg | Neg | +++ | | | 9000 | | | | 2 |
| 138 | Neg | Neg | +++ | | | 4225 | | Neg | | 24 |
| 138 Cord | Neg | Neg | +++ | | | 5000 | | | | 3 |
| 139 | 84.5 | High | | 1:256 | | | IE1, P150, CM2, P65$^{low}$, gB1, gB2 | Neg | | |
| 139 Cord | 88.3 | High | | 1:256 | | | IE1, P150, CM2, P65$^{low}$, gB1, gB2 | | | |
| 140 | 40.6 | Mean | +++ | 1:16 | 4500 | | P150$^{low}$, gB1, gB2$^{low}$ | Neg | | 206 |
| 140 Cord | 51.3 | High | +++ | 1:16 | 8500 | | P150$^{low}$, gB1, gB2$^{low}$ | | | 2 |
| 141 | Neg | Neg | +++ | | | 1750 | | 2/5 | type 3 | 570 |
| 141 Cord | Neg | Neg | +++ | | | 2888 | | | | 2 |
| 142 | Neg | Neg | +++ | | | 2875 | | Neg | | |
| 142 Cord | Neg | Neg | +++ | | | 6550 | | | | |

TABLE 4-continued

Humoral CMV Immune Status in Maternal and Fetal Blood Samples from Placentas at Delivery

| Placenta number | Avidity (%) | Avidity result | CMV IFA | Neut | gB ELISA | IgG1 (mg/ml) | RecomBlot CMV protein profile | Placental Infection Placenta PCR | CMV gB Genotype | sEndoglin sEng (ng/ml) |
|---|---|---|---|---|---|---|---|---|---|---|
| 143 | Neg | Neg | ++ | | | 6500 | | Neg | | |
| 143 Cord | Neg | Neg | +++ | | | 5625 | | | | |
| 144 | 60 | High | +++ | 1:64 | | 3450 | IE1, P150, CM2$^{low}$, P65$^{low}$, gB1, gB2 | Neg | | 81 |
| 144 Cord | 67.5 | High | +++ | 1:64 | | 9500 | IE1, P150, CM2$^{low}$, P65$^{low}$, gB1, gB2 | | | 3 |
| 145 | Neg | Neg | | | | | | Neg | | |
| 145 Cord | Neg | Neg | | | | | | | | |
| 146 | 58.3 | High | +++ | 1:64 | | 3000 | P150, CM2$^{low}$, P65$^{low}$, gB1 | Neg | | |
| 146 Cord | 66.8 | High | +++ | 1:64 | | 3875 | P150, CM2$^{low}$, P65$^{low}$, gB1 | | | |
| 147 | 35 | Mean | +++ | 1:16 | | 6000 | P150, gB1, gB2 | Neg | | 8 |
| 147 Cord | 32.6 | Low | +++ | 1:16 | | 7500 | P150, gB1, gB2 | | | 2 |
| 148 | Neg | Neg | +++ | | | | Neg | Neg | | |
| 148 Cord | Neg | Neg | +++ | | | | Neg | | | |
| 150 | 44.2 | Mean | +++ | 1:64 | | 4875 | P150, CM2, gB1, gB2 | Neg | | 8 |
| 150 Cord | Neg | High | +++ | 1:64 | | 1625 | P150, CM2, gB1, gB2 | | | 3 |
| 151 | Neg | Neg | | | | | | Neg | | |
| 151 Cord | Neg | Neg | | | | | | | | |
| Immune non-pregnant | 58.3 | High | | 1:128 | | | | | | 2 |

CMV-specific High-Avidity IgG: In strongly immune paired sera, the presence of CMV-specific, high-avidity IgG indicates a threshold of protection was reached in pregnant woman that could suppress viral replication should reactivation and uterine infection occur. IgG1, the predominant subclass of antibodies in human blood and first to develop against viral proteins, reaches high avidity through affinity maturation. Several cases of early-stage maternal infection were detected by immunofluorescence reactions agains CMV-infected cells and viral DNA in several biopsy specimens (#105, #108, #128, #141).

CMV Neutralization assays: IgG avidity was evaluated for antiviral function by performing plaque reduction assays (i.e., neutralization). Higher neutralization values closely paralleled development of high avidity. In most instances, titers ranged from 1:8 to 1:256. Low avidity IgG did not contain any neutralizing titer.

CMV gB avidity assays: In collaboration with Sanofi, selected sera were analyzed by a specific ELISA for titers of CMV gB-specific IgG. Surprisingly, titers of antibody to gB were from 10 percent higher to 4-fold higher in fetal circulation than maternal blood except for paired sera #113 from a placenta with 5/5 placental DNA positive biopsy specimens positive indicating virus transmission and congenital infection.

Selective IgG1 transport from maternal circulation to the fetal bloodstream: Binding of IgG1 to the neonatal Fc receptor (FcRn) in syncytiotrophoblasts and transcytosis into the fetal bloodstream, the process of passive immunity, insures that higher levels of protective, virus-specific IgG reach the fetus (Maidji, E., S. McDonagh, O. Genbacev, T. Tabata, and L. Pereira. 2006. Maternal antibodies enhance or prevent cytomegalovirus infection in the placenta by neonatal fc receptor-mediated transcytosis (Maidji et al., *Am J Pathol* 168:1210-26 (2006); Malek et al, *Am J Reprod Immunol* 36:248-55 (1996); Simister et al., *Eur. J. Immunol.*, 26:1527-1531 (1996)). Additional analysis performed with quantitative assays for IgG1 confirmed that fetal circulation contained 2 to 3 times more IgG1 than maternal blood except for paired sera #150.

Immunoblot analysis: Recomblot reactions showed IgG patterns consistent with long past and recurrent infections in paired sera from strongly immune women who suppressed viral replication in the placenta. These results extend our published studies indicating that CMV frequently reactivates in seropositive women in accord with the presence of viral DNA and proteins in placental specimens (McDonagh et al., *J. Infect. Dis.* 190:826-834 (2004); Pereira et al., *J. Virol.* 77:13301-13314 (2003)). Nonetheless, maternal immunity reduces viral replication and injury in the placenta thereby limiting possible transmission. In contrast, sera of women with very recent infection (i.e., immunofluorescence positive) or very low-avidity IgG failed to react with any CMV proteins.

CMV DNA and Replication Proteins in Placentas from Congenital Infection: In quantitative studies of CMV DNA in placentas, when several biopsy specimens contained DNA in the presence of low CMV neutralizing IgG titers suggested fetal transmission (McDonagh, S., E. Maidji, H.-T. Chang, and L. Pereira. 2006. Patterns of human cytomegalovirus infection in term placentas: a preliminary analysis (McDonagh et al., *J. Clin. Virol.*, 35:210-215 (2006)). Accordingly, placentas with low-avidity IgG and low neutralizing titers containing 2 to 5 CMV DNA positive biopsy specimens suggested fetal infection transmission. Immunostaining confirmed UCSF#1, a case of primary maternal infection at midgestation with CMV-specific IgM led to virus transmission. The neonate was congenitally infected and viral DNA was detected in urine at birth. We found the predominant CMV gB genotype in infected placentas we studied was type 3. Interestingly, a placenta from a mother with apparent primary infection contained both genotypes 2 and 3.

sEndoglin: One potential cellular biomarker, soluble Endoglin, was measured in a small number of maternal and fetal sera (Table 4). High values were found in sera of CMV seropositive mothers in accord with virus replication in the placenta. Elevated levels were detected at very early stage primary infection in the absence of neutralizing antibodies. Notably, the highest values appeared to be associated with placental infection and possibly fetal transmission (UCSF#1, #127, #128). In addition, UCSF#1 contained extremely high sFlt1 levels (data not shown). All fetal sera contained low sEng values in the normal range.

These results suggest that passive immunity to CMV in the fetus could rise to levels that exceed IgG1 avidity in circulation in immune women. When high-avidity CMV-specific IgG1 predominates, antibodies are continually transcytosed across the placenta to the fetal circulation throughout gestation. These findings provide strong rationale for the efficacy of early hyperimmune globulin treatment for women with primary CMV infection and low-avidity IgG that could prevent fetal infection and disseminated congenital disease (Nigro et al., *N Engl J Med* 353:1350-62 (2005)). These results suggested that elevated sEng levels are associated with CMV replication in the placenta and eventual virus transmission to the fetus and could be used as a biomarker in the presence of low-avidity CMV-specific IgG.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. All references cited herein are incorporated by reference in their entireties as though each were incorporated by reference individually.

The invention claimed is:

1. A method of diagnosing congenital cytomegalovirus (CMV) infection, the method comprising the steps of:
   (a) obtaining umbilical cord blood or fetal blood from a subject;
   (b) contacting said umbilical cord blood or fetal blood with monoclonal antibodies that specifically bind a panel of selected markers that comprise the group sFlt-1 and cmvIL-10; and;
   (c) determining whether the markers are differentially expressed in said umbilical cord blood or fetal blood compared to umbilical cord blood or fetal blood from a non-infected subject; thereby providing a diagnosis for congenital CMV infection.

2. The method of claim 1, wherein the determining step comprises an enzyme-linked immunosorbant assay (ELISA) or a mass spectroscopy.

3. The method of claim 1, wherein the monoclonal antibodies are detectably labeled.

4. A method of predicting congenital cytomegalovirus (CMV) disease, the method comprising the steps of:
   (a) obtaining umbilical cord blood or fetal blood from a subject;
   (b) contacting said umbilical cord blood or fetal blood with monoclonal antibodies that specifically bind to a panel of selected markers that comprise the group sFlt-1 and cmvIL-10; and;
   (c) determining whether the markers are differentially expressed in said umbilical cord blood or fetal blood compared to umbilical cord blood or fetal blood from a non-infected subject; thereby predicting congenital CMV disease.

5. A method of determining the efficacy of therapy for congenital cytomegalovirus (CMV) infection, the method comprising the steps of:
   (a) obtaining umbilical cord blood or fetal blood from a subject;
   (b) contacting said umbilical cord blood or fetal blood with antibodies that specifically bind a panel of selected markers that comprise the group sFlt-1 and cmvIL-10; and;
   (c) determining whether the markers are differentially expressed in said umbilical cord blood or fetal blood compared to umbilical cord blood or fetal blood obtained from the subject at an earlier time; thereby determining the efficacy of therapy.

6. The method of claim 5, further comprising adjusting the therapy based on the determination of efficacy.

* * * * *